(12) United States Patent
Kasmiri et al.

(10) Patent No.: US 7,855,276 B2
(45) Date of Patent: Dec. 21, 2010

(54) FRAMEWORK RESIDUE SUBSTITUTED HUMANIZED COL-1 ANTIBODIES AND THEIR USE

(75) Inventors: Syed Kasmiri, North Potomac, MD (US); Rafia Mehdi Kashmiri, legal representative, North Potomac, MD (US); Jeffrey Schlom, Potomac, MD (US); Eduardo A. Padlan, Kensington, MD (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 141 days.

(21) Appl. No.: 11/813,092

(22) PCT Filed: Dec. 30, 2005

(86) PCT No.: PCT/US2005/047431
§ 371 (c)(1),
(2), (4) Date: May 7, 2008

(87) PCT Pub. No.: WO2006/074071

PCT Pub. Date: Jul. 13, 2006

(65) Prior Publication Data
US 2008/0274055 A1 Nov. 6, 2008

Related U.S. Application Data

(60) Provisional application No. 60/640,672, filed on Dec. 30, 2004.

(51) Int. Cl.
| | | |
|---|---|---|
| C12P 21/08 | (2006.01) | |
| C07K 16/00 | (2006.01) | |
| A61K 39/395 | (2006.01) | |
| A61K 39/00 | (2006.01) | |
| G01N 33/53 | (2006.01) | |

(52) U.S. Cl. .............. 530/387.3; 530/387.1; 530/387.7; 530/388.1; 530/388.8; 424/130.1; 424/133.1; 424/134.1; 424/138.1; 435/7.1

(58) Field of Classification Search .................. None
See application file for complete search history.

(56) References Cited

U.S. PATENT DOCUMENTS

| | | | |
|---|---|---|---|
| 5,472,693 | A | 12/1995 | Gourlie et al. |
| 5,851,526 | A | 12/1998 | Welt et al. |
| 6,020,153 | A | 2/2000 | Hardman et al. |
| 6,333,405 | B1 | 12/2001 | Anderson et al. |
| 6,417,337 | B1 | 7/2002 | Anderson et al. |
| 7,355,008 | B2 * | 4/2008 | Stavenhagen et al. .... 530/387.1 |
| 2002/0052479 | A1 * | 5/2002 | Anderson et al. ...... 530/388.85 |
| 2003/0039649 | A1 | 2/2003 | Foote |

FOREIGN PATENT DOCUMENTS

| | | |
|---|---|---|
| WO | WO00/26394 | 5/2000 |
| WO | WO03/002607 | 1/2003 |
| WO | WO2004/006955 | 1/2004 |
| WO | WO2004/022717 | 3/2004 |

OTHER PUBLICATIONS

Adams et al., "Generating improved single-chain Fv molecules tumor targeting," *Journal of Immunological Methods*, 231:249-260 (1999).

Osbourn et al., "Generation of a panel of related human scFv antibodies with high affinities for human CEA," *Immunotechnology*, 2:181-196 (1996).

Caldas et al., "Design and synthesis of germline-based hemi-humanized single-chain Fv against the CD18 surface antigen," *Protein Eng.*, 13(5):353-360, 2000.

Caldas et al., "Humanization of the anti-CD18 antibody 6.7: an unexpected effect of a framework residue in binding to antigen," *Mol. Immunol.*, 39(15):941-952, 2003.

De Pascalis et al., "Grafting of "abbreviated" complementarity-determining regions containing specificity-determining residues essential for ligand contact to engineer a less immunogenic humanized monoclonal antibody," *J. Immunol.*, 169(6):3076-3084, 2002.

Folli et al., "Immunophotodiagnosis of colon carcinomas in patients injected with fluoresceinated chimeric antibodies against carcinoembryonic antigen," *Proc. Natl. Acad. Sci. USA*, 89(17):7973-7977, 1992.

Gonzales et al., "Minimizing immunogenicity of the SDR-grafted humanized antibody CC49 by genetic manipulation of the framework residues," *Mol. Immunol.*, 40(6):337-349, 2003.

Gonzales et al., "SDR grafting of a murine antibody using multiple human germline templates to minimize its immunogenicity," *Mol. Immunol.*, 41(9):863-872, 2004.

Kashmiri et al., "Generation, characterization, and in vivo studies of humanized anticarcinoma antibody CC49," *Hybridoma*, 14(5):461-473, 1995.

Kashmiri et al., "Development of a minimally immunogenic variant of humanized anti-carcinoma monoclonal antibody CC49," *Crit. Rev. Oncol. Hematol.*, 38:3-16, 2001.

Kashmiri et al., Chapter 21, pp. 361-376, *Methods in Molecular Biology*, vol. 248: *Antibody Engineering: Methods and Protocols*, Ed.: B.K.C. Lo, Humana Press, Tolowa, NJ, 2004.

(Continued)

*Primary Examiner*—Anne M. Gussow
(74) *Attorney, Agent, or Firm*—Klarquist Sparkman, LLP

(57) ABSTRACT

The present disclosure provides humanized COL-1 monoclonal antibodies that retain CEA binding affinity, compared to a parent antibody. Also disclosed herein are humanized COL-1 monoclonal antibodies that have reduced immunogenicity, compared to a parent antibody. The disclosed humanized COL-1 antibodies include substitution of framework residues with residues from the corresponding positions of a homologous human sequence. In several embodiments, methods are disclosed for the use of a humanized COL-1 antibody in the detection or treatment of a CEA-expressing tumor or cell in a subject. Also disclosed is a kit including the humanized COL-1 antibodies described herein.

47 Claims, 13 Drawing Sheets

OTHER PUBLICATIONS

Kass et al., "Carcinoembryonic antigen as a target for specific anti-tumor immunotherapy of head and neck cancer," *Cancer Res.*, 62(17):5049-5057, 2002.

Muraro et al., "Definition by monoclonal antibodies of a repertoire of epitopes on carcinoembryonic antigen differentially expressed in human colon carcinomas versus normal adult tissues," *Cancer Res.*, 45(11 Pt 2):5769-5780, 1985.

Ohuchi et al., "Differential expression of carcinoembryonic antigen in early gastric adenocarcinomas versus benign gastric lesions defined by monoclonal antibodies reactive with restricted antigen epitopes," *Cancer Res.*, 47(13):3565-3571, 1987.

Padlan et al., "Identification of specificity-determining residues in antibodies," *FASEB J.*, 9(1):133-139, 1995.

Raben et al., "Enhancement of radiolabeled antibody binding and tumor localization through adenoviral transduction of the human carcinoembryonic antigen gene," *Gene Ther.*, 3(7):567-580, 1996.

Ravindranath et al., "Does human melanoma express carcinoembryonic antigen," 20(5A):3083-3092, 2000 (abstract only).

Raynor et al., "Optimisation of the RT-PCR detection of immunomagnetically enriched carcinoma cells," *BMC Cancer*, 2:14, 2002.

Robbins et al., "Definition of the expression of the human carcinoembryonic antigen and non-specific cross-reacting antigen in human breast and lung carcinomas," *Int. J. Cancer*, 53(6):892-897, 1993 (abstract only).

Rosok et al., "A combinatorial library strategy for the rapid humanization of anticarcinoma BR96 Fab," *J. Biol. Chem.*, 271(37):22611-22618, 1996.

Siler et al., "Therapeutic efficacy of a high-affinity anticarcinoembryonic antigen monoclonal antibody (COL-1)," *Biotechnol. Ther.*, 4(3-4):163-181, 1993 (abstract only).

Tamura et al., "Structural correlates of an anticarcinoma antibody: identification of specificity-determining residues (SDRs) and development of a minimally immunogenic antibody variant by retention of SDRs only," *J. Immunol.*, 164(3):1432-1441, 2000.

Tan et al., "'SuperhumanizedΔ antibodies: reduction of immunogenic potential by complementarity-determining region grafting with human germline sequences: application to an anti-CD28," *J. Immunol.*, 169(2):1119-1125, 2002.

Wilkinson et al., "Antibody targeting studies in a transgenic murine model of spontaneous colorectal tumors," *Proc. Natl. Acad. Sci. USA*, 98(18):10256-10260, 2001.

Yan et al., "Oncogenic c-Ki-ras but not oncogenic c-Ha-ras up-regulates CEA expression and disrupts basolateral polarity in colon epithelial cells," *J. Biol. Chem.*, 272(44):27902-27907, 1997.

Yu et al., "Phase I trial of iodine 131-labeled COL-1 in patients with gastrointestinal malignancies: influence of serum carcinoembryonic antigen and tumor bulk on pharmacokinetics," *J. Clin. Oncol.*, 14(6):1798-1809, 1996.

\* cited by examiner

FIG. 1A

|  | FR1 | CDR1 | FR2 | CDR2 |
|---|---|---|---|---|
| mCOL-1 (SEQ ID NO:1) | DIVLTQSPASLTVSLGLRATISC | RASKSVSASGYSYMH | WYQQRPGQPPKLLIY | LASNLQS |
| VJI'CL (SEQ ID NO:2) | ----M------A-------- | ---KS-Q--LYNNKN-LA | ---------K------- | W---TRE- |
| HuCOL-1 (SEQ ID NO:3) | ----L------A-------- | ---RA--K--SASGYS-MH | ---------K------- | L---NLQ- |
| AbrCDR (SEQ ID NO:4) | ----L------A-------- | ---KS-Q--SASGYS-MH | ---------K------- | L---NLQ- |

|  | FR3 | CDR3 | FR4 |
|---|---|---|---|
| mCOL-1 | GVPARFSGSGSGTDFTLNIHPVEEEDAATYYC | QHSRELPT | FGGGTKLEIK |
| VJI'CL | ---D------T--SSLQA--V-V--- | -QYDTI-- | ----------- |
| HuCOL-1 | ---A------T--SSVQA--V-T--- | -HSREL-- | -----V---- |
| AbrCDR | ---A------T--SSVQA--V-T--- | -HSREL-- | -----L---- |

FIG. 1B

|  | FR1 | CDR1 | FR2 | CDR2 |
|---|---|---|---|---|
| mCOL-1 (SEQ ID NO:5) | EVQLQQSGAELVRSGASVKMSCTASGFNIK | DYYMH | WVKQRPEQGLEWIG | WIDPENGDTEYAP |
| MO30 (SEQ ID NO:6) | Q----------VKKP------V--K--YTFT | N---- | ---R--A-G---M- | I--N-SGNS-N--Q |
| HuCOL-1 (SEQ ID NO:7) | E----------VVKP------M--K-FNIK | D---- | ---K--A-G----I- | W-D--ENGD-E--P |
| AbrCDR (SEQ ID NO:8) | E----------VVKP------M--K-FNIK | D---- | ---K--R-E----I- | W-D--ENGD-E--Q |

|  | FR3 | CDR3 | FR4 |
|---|---|---|---|
| mCOL-1 | KFQG KATMTTDTSSNTAYLQLSSLTSEDTAVYYCNT | RGLSTMITTRWFFDV | WGAGTTVAVSS |
| MO30 | ---- RV---R----TS-V-ME------R- | -AR EK-A-T-FIITGM-Y | ---Q-L-T--- |
| HuCOL-1 | ---- KA---T----TS-A-LE------R- | -NT RG-S-M-TTRWFF-V | ---A-L-T--- |
| AbrCDR | ---- KA---T----TS-A-LE------R- | -NT RG-S-M-TTRWFF-V | ---A-L-T--- |

FIG. 2A

```
                                    FR1                                            CDR1
                          *       *       *       *       *       *       *       *
VJ'CL  (SEQ ID NO: 2)   D I V M T Q S P A S L A V S L G E R A T I N C   K S S Q S V L Y N N K N Y L A
AbrCDR (SEQ ID NO: 4)   D I V L T Q S P A S L A V S L G E R A T I N C   K S S Q S V S A S G Y S Y M H
FRV4   (SEQ ID NO: 9)   - - - L - - - - - - - - - - - - - - - - - - -   - - - - - - S A S G Y S - M H
FRV7   (SEQ ID NO: 10)  - - - L - - - - - - - - - - - - - - - - - - -   - - - - - - S A S G Y S - M H
FRV10  (SEQ ID NO: 11)  - - - L - - - - - - - - - - - - - - - - - - -   - - - - - - S A S G Y S - M H

FR2                                CDR2
                          *       *       *       *       *       *
VJ'CL                   W Y Q Q K P G Q P P K L L I Y   W A S T R E S
AbrCDR                  W Y Q Q K P G Q P P K L L I Y   L A S N L Q S
FRV4                    - - - - - - - - - - - - - - -   L - - N L Q -
FRV7                    - - - - - - - - - - - - - - -   L - - N L Q -
FRV10                   - - - - - - - - - - - - - - -   L - - N L Q -

FR3                                           CDR3
                          *       *       *       *       *       *       *       *
VJ'CL                   G V P D R F S G S G S G T D F T L T I S S L Q A E D V A V Y Y C   Q Q Y D T I P T
AbrCDR                  G V P A R F S G S G S G T D F T L T I S S V Q A E D V A T Y Y C   Q H S R E L P T
FRV4                    - - - A - - - - - - - - - - - - - - - - V - - - - - - T - - -     - H S R E L - -
FRV7                    - - - A - - - - - - - - - - - - - - - - V - - - - - - T - - -     - H S R E L - -
FRV10                   - - - A - - - - - - - - - - - - - - - - V - - - - - - T - - -     - H S R E L - -

FR4
                          *       *
VJ'CL                   F G G G T K V E I K
AbrCDR                  F G G G T K L E I K
FRV4                    - - - - - - L - - -
FRV7                    - - - - - - L - - -
FRV10                   - - - - - - L - - -
```

FIG. 2B

```
                                      FR1                                          CDR1
                          *       *       *       *       *       *       *       *
MO30   (SEQ ID NO: 6)   Q V Q L V Q S G A E V K K P G A S V K V S C K A S G Y T F T   N Y Y M H
AbrCDR (SEQ ID NO: 8)   E V Q L V Q S G A E V V K P G A S V K M S C K A S G F N I K   D Y Y M H
FRV4   (SEQ ID NO: 12)  E - - - - - - - - - - V - - - - - - - - - - - - - F N I K   D - - - -
FRV7   (SEQ ID NO: 13)  E - - - - - - - - - - - - - - - - - - - - - - - - Y N I K   D - - - -
FRV10  (SEQ ID NO: 14)  Q - - - - - - - - - - - - - - - - - - - - - - - - Y N I K   D - - - -

FR2                              CDR2
                          *       *       *       *       *       *
MO30                    W V R Q A P G Q G L E W M G   I I N P S G N S T N Y A Q
AbrCDR                  W V K Q R P E Q G L E W I G   W I D P E N G D T E Y A Q
FRV4                    - - R - R - - E - - - - M -   - W - D - E N G D - E - -
FRV7                    - - R - R - - E - - - - M -   - W - D - E N G D - E - -
FRV10                   - - R - R - - E - - - - M -   - W - D - E N G D - E - -

FR3
                          *       *       *       *       *       *       *       *
MO30                    K F Q G   R V T M T R D T S T S T V Y M E L S S L R S E D T A V Y Y C A R
AbrCDR                  K F Q G   K A T M T T D T S T S T A Y L E L S S L R S E D T A V Y Y C N T
FRV4                    - - - -   R A - - T - - - - - - - - - V - M - - - - - - - - - - - - N T
FRV7                    - - - -   R V - - T - - - - - - - - - V - M - - - - - - - - - - - - N T
FRV10                   - - - -   R V - - T - - - - - - - - - V - M - - - - - - - - - - - - N T

CDR3                                       FR4
                          *       *       *       *       *       *       *
MO30                    E K L A T T I F I I T G M D Y   W G Q G T L V T V S S
AbrCDR                  R G L S T M I T T R W F F D V   W G A G T L V T V S S
FRV4                    R G - S - M - T T R W F F - V   - - - A - - - - - - -
FRV7                    R G - S - M - T T R W F F - V   - - - A - - - - - - -
FRV10                   R G - S - M - T T R W F F - V   - - - A - - - - - - -
```

FIG. 6A  Serum EM (149)
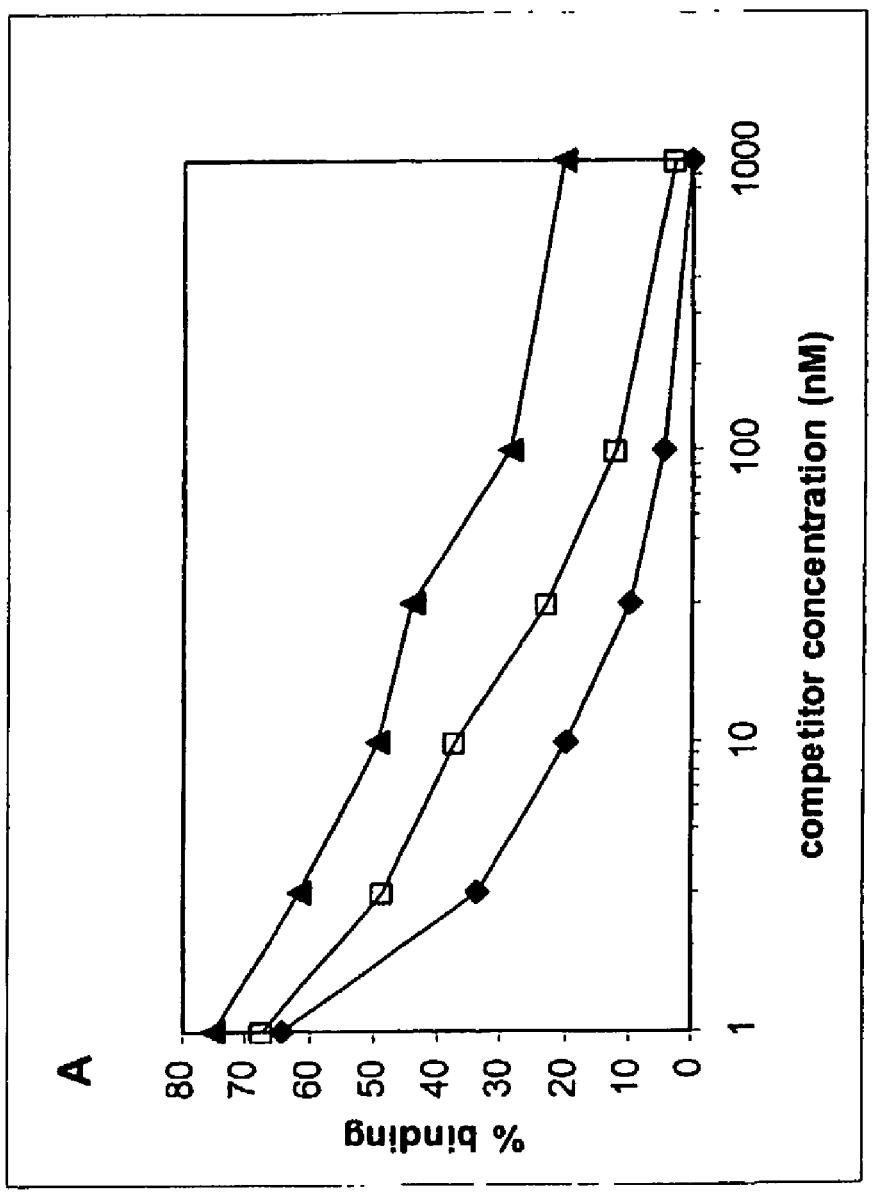
| | IC50 |
|---|---|
| HuCOL-1 | 1.9 |
| ABR | 2.9 |
| FR10 | 9.7 |

SEQUENCE LISTING

<160> NUMBER OF SEQ ID NOS: 29

<210> SEQ ID NO 1
<211> LENGTH: 110
<212> TYPE: PRT
<213> ORGANISM: Mus Musculus

<400> SEQUENCE: 1

Asp Ile Val Leu Thr Gln Ser Pro Ala Ser Leu Thr Val Ser Leu Gly
1               5                   10                  15

Leu Arg Ala Thr Ile Ser Cys Arg Ala Ser Lys Ser Val Ser Ala Ser
            20                  25                  30

Gly Tyr Ser Tyr Met His Trp Tyr Gln Gln Arg Pro Gly Gln Pro Pro
        35                  40                  45

Lys Leu Leu Ile Tyr Leu Ala Ser Asn Leu Gln Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln His Ser Arg
                85                  90                  95

Glu Leu Pro Thr Phe Gly Gly Gly Thr Lys Leu Glu Ile Lys
            100                 105                 110

<210> SEQ ID NO 2
<211> LENGTH: 110
<212> TYPE: PRT
<213> ORGANISM: Homo sapiens

```
<400> SEQUENCE: 2

Asp Ile Val Met Thr Gln Ser Pro Ala Ser Leu Ala Val Ser Leu Gly
1               5                   10                  15

Glu Arg Ala Thr Ile Asn Cys Lys Ser Ser Gln Ser Val Leu Tyr Asn
            20                  25                  30

Asn Lys Asn Tyr Leu Ala Trp Tyr Gln Gln Lys Pro Gly Gln Pro Pro
        35                  40                  45

Lys Leu Leu Ile Tyr Trp Ala Ser Thr Arg Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Tyr Asp
                85                  90                  95

Thr Ile Pro Thr Phe Gly Gly Gly Thr Lys Val Glu Ile Lys
            100                 105                 110

<210> SEQ ID NO 3
<211> LENGTH: 110
<212> TYPE: PRT
<213> ORGANISM: Artificial Sequence
<220> FEATURE:
<223> OTHER INFORMATION: Variable light chain of the HuCOL-1 antibody

<400> SEQUENCE: 3

Asp Ile Val Leu Thr Gln Ser Pro Ala Ser Leu Ala Val Ser Leu Gly
1               5                   10                  15

Glu Arg Ala Thr Ile Asn Cys Arg Ala Ser Lys Ser Val Ser Ala Ser
            20                  25                  30

Gly Tyr Ser Tyr Met His Trp Tyr Gln Gln Lys Pro Gly Gln Pro Pro
        35                  40                  45

Lys Leu Leu Ile Tyr Leu Ala Ser Asn Leu Gln Ser Gly Val Pro Ala
    50                  55                  60

Arg Phe Ser Gly Ser Gly Ser Gly Thr Asp Phe Thr Leu Thr Ile Ser
65                  70                  75                  80

Ser Val Gln Ala Glu Asp Val Ala Thr Tyr Tyr Cys Gln His Ser Arg
                85                  90                  95

Glu Leu Pro Thr Phe Gly Gly Gly Thr Lys Leu Glu Ile Lys
            100                 105                 110

<210> SEQ ID NO 4
<211> LENGTH: 110
<212> TYPE: PRT
<213> ORGANISM: Artificial Sequence
<220> FEATURE:
<223> OTHER INFORMATION: Variable light chain of the HuCOL-1AbrCDR
      antibody

<400> SEQUENCE: 4

Asp Ile Val Leu Thr Gln Ser Pro Ala Ser Leu Ala Val Ser Leu Gly
1               5                   10                  15

Glu Arg Ala Thr Ile Asn Cys Lys Ser Ser Gln Ser Val Ser Ala Ser
            20                  25                  30

Gly Tyr Ser Tyr Met His Trp Tyr Gln Gln Lys Pro Gly Gln Pro Pro
        35                  40                  45

Lys Leu Leu Ile Tyr Leu Ala Ser Asn Leu Gln Ser Gly Val Pro Ala
    50                  55                  60

Arg Phe Ser Gly Ser Gly Ser Gly Thr Asp Phe Thr Leu Thr Ile Ser
```

```
                65                  70                  75                  80
Ser Val Gln Ala Glu Asp Val Ala Thr Tyr Tyr Cys Gln His Ser Arg
                    85                  90                  95

Glu Leu Pro Thr Phe Gly Gly Gly Thr Lys Leu Glu Ile Lys
                100                 105                 110

<210> SEQ ID NO 5
<211> LENGTH: 124
<212> TYPE: PRT
<213> ORGANISM: Mus musculus

<400> SEQUENCE: 5

Glu Val Gln Leu Gln Gln Ser Gly Ala Glu Leu Val Arg Ser Gly Ala
1               5                   10                  15

Ser Val Lys Met Ser Cys Thr Ala Ser Gly Phe Asn Ile Lys Asp Tyr
                20                  25                  30

Tyr Met His Trp Val Lys Gln Arg Pro Glu Gln Gly Leu Glu Trp Ile
            35                  40                  45

Gly Trp Ile Asp Pro Glu Asn Gly Asp Thr Glu Tyr Ala Pro Lys Phe
        50                  55                  60

Gln Gly Lys Ala Thr Met Thr Thr Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Asn Thr Arg Gly Leu Ser Thr Met Ile Thr Thr Arg Trp Phe Phe Asp
                100                 105                 110

Val Trp Gly Ala Gly Thr Thr Val Ala Val Ser Ser
            115                 120

<210> SEQ ID NO 6
<211> LENGTH: 124
<212> TYPE: PRT
<213> ORGANISM: Homo sapiens

<400> SEQUENCE: 6

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
                20                  25                  30

Tyr Met His Trp Val Arg Gln Ala Pro Gly Gln Gly Leu Glu Trp Met
            35                  40                  45

Gly Ile Ile Asn Pro Ser Gly Asn Ser Thr Asn Tyr Ala Gln Lys Phe
        50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Glu Lys Leu Ala Thr Thr Ile Phe Ile Ile Thr Gly Met Asp
                100                 105                 110

Tyr Trp Gly Gln Gly Thr Leu Val Thr Val Ser Ser
            115                 120

<210> SEQ ID NO 7
<211> LENGTH: 124
<212> TYPE: PRT
<213> ORGANISM: Artificial Sequence
<220> FEATURE:
<223> OTHER INFORMATION: Variable heavy chain of the HuCOL-1 antibody
```

```
<400> SEQUENCE: 7

Glu Val Gln Leu Val Gln Ser Gly Ala Glu Val Val Lys Pro Gly Ala
1               5                   10                  15

Ser Val Lys Met Ser Cys Lys Ala Ser Gly Phe Asn Ile Lys Asp Tyr
            20                  25                  30

Tyr Met His Trp Val Lys Gln Ala Pro Gly Gln Gly Leu Glu Trp Ile
        35                  40                  45

Gly Trp Ile Asp Pro Glu Asn Gly Asp Thr Glu Tyr Ala Pro Lys Phe
    50                  55                  60

Gln Gly Lys Ala Thr Met Thr Thr Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Asn Thr Arg Gly Leu Ser Thr Met Ile Thr Thr Arg Trp Phe Phe Asp
            100                 105                 110

Val Trp Gly Ala Gly Thr Leu Val Thr Val Ser Ser
        115                 120

<210> SEQ ID NO 8
<211> LENGTH: 124
<212> TYPE: PRT
<213> ORGANISM: Artificial Sequence
<220> FEATURE:
<223> OTHER INFORMATION: Variable light chain of the HuCOL-1AbrCDR
      antibody

<400> SEQUENCE: 8

Glu Val Gln Leu Val Gln Ser Gly Ala Glu Val Val Lys Pro Gly Ala
1               5                   10                  15

Ser Val Lys Met Ser Cys Lys Ala Ser Gly Phe Asn Ile Lys Asp Tyr
            20                  25                  30

Tyr Met His Trp Val Lys Gln Arg Pro Glu Gln Gly Leu Glu Trp Ile
        35                  40                  45

Gly Trp Ile Asp Pro Glu Asn Gly Asp Thr Glu Tyr Ala Gln Lys Phe
    50                  55                  60

Gln Gly Lys Ala Thr Met Thr Thr Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Asn Thr Arg Gly Leu Ser Thr Met Ile Thr Thr Arg Trp Phe Phe Asp
            100                 105                 110

Val Trp Gly Ala Gly Thr Leu Val Thr Val Ser Ser
        115                 120

<210> SEQ ID NO 9
<211> LENGTH: 110
<212> TYPE: PRT
<213> ORGANISM: Artificial Sequence
<220> FEATURE:
<223> OTHER INFORMATION: Variable light chain of FRV4

<400> SEQUENCE: 9

Asp Ile Val Leu Thr Gln Ser Pro Ala Ser Leu Ala Val Ser Leu Gly
1               5                   10                  15

Glu Arg Ala Thr Ile Asn Cys Lys Ser Ser Gln Ser Val Ser Ala Ser
            20                  25                  30

Gly Tyr Ser Tyr Met His Trp Tyr Gln Gln Lys Pro Gly Gln Pro Pro
```

```
                35                  40                  45
Lys Leu Leu Ile Tyr Leu Ala Ser Asn Leu Gln Ser Gly Val Pro Ala
         50                  55                  60
Arg Phe Ser Gly Ser Gly Ser Gly Thr Asp Phe Thr Leu Thr Ile Ser
 65                  70                  75                  80
Ser Val Gln Ala Glu Asp Val Ala Thr Tyr Tyr Cys Gln His Ser Arg
                 85                  90                  95
Glu Leu Pro Thr Phe Gly Gly Gly Thr Lys Leu Glu Ile Lys
                100                 105                 110

<210> SEQ ID NO 10
<211> LENGTH: 110
<212> TYPE: PRT
<213> ORGANISM: Artificial Sequence
<220> FEATURE:
<223> OTHER INFORMATION: Variable light chain of FRV7

<400> SEQUENCE: 10

Asp Ile Val Leu Thr Gln Ser Pro Ala Ser Leu Ala Val Ser Leu Gly
 1               5                  10                  15
Glu Arg Ala Thr Ile Asn Cys Lys Ser Ser Gln Ser Val Ser Ala Ser
                20                  25                  30
Gly Tyr Ser Tyr Met His Trp Tyr Gln Gln Lys Pro Gly Gln Pro Pro
             35                  40                  45
Lys Leu Leu Ile Tyr Leu Ala Ser Asn Leu Gln Ser Gly Val Pro Ala
         50                  55                  60
Arg Phe Ser Gly Ser Gly Ser Gly Thr Asp Phe Thr Leu Thr Ile Ser
 65                  70                  75                  80
Ser Val Gln Ala Glu Asp Val Ala Thr Tyr Tyr Cys Gln His Ser Arg
                 85                  90                  95
Glu Leu Pro Thr Phe Gly Gly Gly Thr Lys Leu Glu Ile Lys
                100                 105                 110

<210> SEQ ID NO 11
<211> LENGTH: 110
<212> TYPE: PRT
<213> ORGANISM: Artificial Sequence
<220> FEATURE:
<223> OTHER INFORMATION: Variable light chain of FRV10

<400> SEQUENCE: 11

Asp Ile Val Leu Thr Gln Ser Pro Ala Ser Leu Ala Val Ser Leu Gly
 1               5                  10                  15
Glu Arg Ala Thr Ile Asn Cys Lys Ser Ser Gln Ser Val Ser Ala Ser
                20                  25                  30
Gly Tyr Ser Tyr Met His Trp Tyr Gln Gln Lys Pro Gly Gln Pro Pro
             35                  40                  45
Lys Leu Leu Ile Tyr Leu Ala Ser Asn Leu Gln Ser Gly Val Pro Ala
         50                  55                  60
Arg Phe Ser Gly Ser Gly Ser Gly Thr Asp Phe Thr Leu Thr Ile Ser
 65                  70                  75                  80
Ser Val Gln Ala Glu Asp Val Ala Thr Tyr Tyr Cys Gln His Ser Arg
                 85                  90                  95
Glu Leu Pro Thr Phe Gly Gly Gly Thr Lys Leu Glu Ile Lys
                100                 105                 110

<210> SEQ ID NO 12
<211> LENGTH: 124
```

```
<212> TYPE: PRT
<213> ORGANISM: Artificial Sequence
<220> FEATURE:
<223> OTHER INFORMATION: Variable heavy chain of FRV4

<400> SEQUENCE: 12

Glu Val Gln Leu Val Gln Ser Gly Ala Glu Val Val Lys Pro Gly Ala
1               5                   10                  15

Ser Val Lys Val Ser Cys Lys Ala Ser Gly Phe Asn Ile Lys Asp Tyr
            20                  25                  30

Tyr Met His Trp Val Arg Gln Arg Pro Glu Gln Gly Leu Glu Trp Met
        35                  40                  45

Gly Trp Ile Asp Pro Glu Asn Gly Asp Thr Glu Tyr Ala Gln Lys Phe
    50                  55                  60

Gln Gly Arg Ala Thr Met Thr Thr Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Asn Thr Arg Gly Leu Ser Thr Met Ile Thr Thr Arg Trp Phe Phe Asp
            100                 105                 110

Val Trp Gly Ala Gly Thr Leu Val Thr Val Ser Ser
        115                 120

<210> SEQ ID NO 13
<211> LENGTH: 124
<212> TYPE: PRT
<213> ORGANISM: Artificial Sequence
<220> FEATURE:
<223> OTHER INFORMATION: Variable heavy chain of FRV7

<400> SEQUENCE: 13

Glu Val Gln Leu Val Gln Ser Gly Ala Glu Val Val Lys Pro Gly Ala
1               5                   10                  15

Ser Val Lys Val Ser Cys Lys Ala Ser Gly Tyr Asn Ile Lys Asp Tyr
            20                  25                  30

Tyr Met His Trp Val Arg Gln Arg Pro Glu Gln Gly Leu Glu Trp Met
        35                  40                  45

Gly Trp Ile Asp Pro Glu Asn Gly Asp Thr Glu Tyr Ala Gln Lys Phe
    50                  55                  60

Gln Gly Arg Val Thr Met Thr Thr Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Asn Thr Arg Gly Leu Ser Thr Met Ile Thr Thr Arg Trp Phe Phe Asp
            100                 105                 110

Val Trp Gly Ala Gly Thr Leu Val Thr Val Ser Ser
        115                 120

<210> SEQ ID NO 14
<211> LENGTH: 124
<212> TYPE: PRT
<213> ORGANISM: Artificial Sequence
<220> FEATURE:
<223> OTHER INFORMATION: Variable heavy chain of FRV10

<400> SEQUENCE: 14

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Asn Ile Lys Asp Tyr
```

```
                20                  25                  30

Tyr Met His Trp Val Arg Gln Arg Pro Glu Gln Gly Leu Glu Trp Met
        35                  40                  45

Gly Trp Ile Asp Pro Glu Asn Gly Asp Thr Glu Tyr Ala Gln Lys Phe
 50                  55                  60

Gln Gly Arg Val Thr Met Thr Thr Asp Thr Ser Thr Ser Thr Val Tyr
 65                  70                  75                  80

Met Glu Leu Ser Ser Leu Arg Ser Glu Asp Thr Ala Val Tyr Tyr Cys
                85                  90                  95

Asn Thr Arg Gly Leu Ser Thr Met Ile Thr Thr Arg Trp Phe Phe Asp
            100                 105                 110

Val Trp Gly Ala Gly Thr Leu Val Thr Val Ser Ser
        115                 120

<210> SEQ ID NO 15
<211> LENGTH: 110
<212> TYPE: PRT
<213> ORGANISM: Artificial Sequence
<220> FEATURE:
<223> OTHER INFORMATION: Variable light chain of the HuCOL-1SDR antibody

<400> SEQUENCE: 15

Asp Ile Val Leu Thr Gln Ser Pro Asp Ser Leu Ala Val Ser Leu Gly
 1               5                  10                  15

Glu Arg Ala Thr Ile Asn Cys Arg Ala Ser Gln Ser Val Ser Ala Ser
                20                  25                  30

Gly Tyr Ser Tyr Leu His Trp Tyr Gln Gln Lys Pro Gly Gln Pro Pro
            35                  40                  45

Lys Leu Leu Ile Tyr Leu Ala Ser Ser Leu Gln Ser Gly Val Pro Ala
 50                  55                  60

Arg Phe Ser Gly Ser Gly Ser Gly Thr Asp Phe Thr Leu Thr Ile Ser
 65                  70                  75                  80

Ser Val Gln Ala Glu Asp Val Ala Thr Tyr Tyr Cys Gln Gln Ser Arg
                85                  90                  95

Glu Leu Pro Thr Phe Gly Gly Gly Thr Lys Leu Glu Ile Lys
            100                 105                 110

<210> SEQ ID NO 16
<211> LENGTH: 110
<212> TYPE: PRT
<213> ORGANISM: Artificial Sequence
<220> FEATURE:
<223> OTHER INFORMATION: Variable heavy chain of the HuCOL-1SDR antibody

<400> SEQUENCE: 16

Asp Ile Val Leu Thr Gln Ser Pro Asp Ser Leu Ala Val Ser Leu Gly
 1               5                  10                  15

Glu Arg Ala Thr Ile Asn Cys Arg Ala Ser Gln Ser Val Ser Ala Ser
                20                  25                  30

Gly Tyr Ser Tyr Leu His Trp Tyr Gln Gln Lys Pro Gly Gln Pro Pro
            35                  40                  45

Lys Leu Leu Ile Tyr Leu Ala Ser Ser Leu Gln Ser Gly Val Pro Ala
 50                  55                  60

Arg Phe Ser Gly Ser Gly Ser Gly Thr Asp Phe Thr Leu Thr Ile Ser
 65                  70                  75                  80

Ser Val Gln Ala Glu Asp Val Ala Thr Tyr Tyr Cys Gln Gln Ser Arg
                85                  90                  95
```

```
Glu Leu Pro Thr Phe Gly Gly Gly Thr Lys Leu Glu Ile Lys
        100                 105                 110
```

<210> SEQ ID NO 17
<211> LENGTH: 4
<212> TYPE: PRT
<213> ORGANISM: Artificial Sequence
<220> FEATURE:
<223> OTHER INFORMATION: Peptide

<400> SEQUENCE: 17

Lys Asp Glu Leu
1

<210> SEQ ID NO 18
<211> LENGTH: 4
<212> TYPE: PRT
<213> ORGANISM: Artificial Sequence
<220> FEATURE:
<223> OTHER INFORMATION: Peptide

<400> SEQUENCE: 18

Arg Glu Asp Leu
1

<210> SEQ ID NO 19
<211> LENGTH: 21
<212> TYPE: DNA
<213> ORGANISM: Artificial Sequence
<220> FEATURE:
<223> OTHER INFORMATION: Variable heavy chain 3' primer

<400> SEQUENCE: 19
cagctgcacc tgggagtgca c                                        21

<210> SEQ ID NO 20
<211> LENGTH: 24
<212> TYPE: DNA
<213> ORGANISM: Artificial Sequence
<220> FEATURE:
<223> OTHER INFORMATION: Variable heavy chain 3' primer

<400> SEQUENCE: 20
ccccaggttt cttcacctca gcgc                                     24

<210> SEQ ID NO 21
<211> LENGTH: 25
<212> TYPE: DNA
<213> ORGANISM: Artificial Sequence
<220> FEATURE:
<223> OTHER INFORMATION: Variable heavy chain 3' primer

<400> SEQUENCE: 21
ccttgcagga caccttcacg gaagc                                    25

<210> SEQ ID NO 22
<211> LENGTH: 21
<212> TYPE: DNA
<213> ORGANISM: Artificial Sequence
<220> FEATURE:
<223> OTHER INFORMATION: Variable heavy chain 3' primer

<400> SEQUENCE: 22
tttaatgttg tatccagatg c                                        21

<210> SEQ ID NO 23

```
<211> LENGTH: 34
<212> TYPE: DNA
<213> ORGANISM: Artificial Sequence
<220> FEATURE:
<223> OTHER INFORMATION: Variable heavy chain 3' primer

<400> SEQUENCE: 23
aagcccttgt ccaggggcct gcctcaccca gtgc                              34

<210> SEQ ID NO 24
<211> LENGTH: 34
<212> TYPE: DNA
<213> ORGANISM: Artificial Sequence
<220> FEATURE:
<223> OTHER INFORMATION: Variable heavy chain 5' primer

<400> SEQUENCE: 24
cctggacaag ggcttgagtg gatgggatgg attg                              34

<210> SEQ ID NO 25
<211> LENGTH: 21
<212> TYPE: DNA
<213> ORGANISM: Artificial Sequence
<220> FEATURE:
<223> OTHER INFORMATION: Variable heavy chain 5' primer

<400> SEQUENCE: 25
ttccagggca gggccaccat g                                            21

<210> SEQ ID NO 26
<211> LENGTH: 21
<212> TYPE: DNA
<213> ORGANISM: Artificial Sequence
<220> FEATURE:
<223> OTHER INFORMATION: Variable heavy chain 5' primer

<400> SEQUENCE: 26
cagggcaggg tcaccatgac c                                            21

<210> SEQ ID NO 27
<211> LENGTH: 25
<212> TYPE: DNA
<213> ORGANISM: Artificial Sequence
<220> FEATURE:
<223> OTHER INFORMATION: Variable heavy chain 5' primer

<400> SEQUENCE: 27
cacgacggtc tacatggagc tgagc                                        25

<210> SEQ ID NO 28
<211> LENGTH: 25
<212> TYPE: DNA
<213> ORGANISM: Artificial Sequence
<220> FEATURE:
<223> OTHER INFORMATION: Variable heavy chain 5' primer

<400> SEQUENCE: 28
ctagaattcc accatggagt ggtcc                                        25

<210> SEQ ID NO 29
<211> LENGTH: 21
```

```
<212> TYPE: DNA
<213> ORGANISM: Artificial Sequence
<220> FEATURE:
<223> OTHER INFORMATION: Variable heavy chain 3' primer

<400> SEQUENCE: 29
tgggcccttg gtggaggctg a                                        21
```

FRAMEWORK RESIDUE SUBSTITUTED HUMANIZED COL-1 ANTIBODIES AND THEIR USE

PRIORITY CLAIM

This is the U.S. National Stage of International Application No. PCT/US2005/047431, filed Dec. 30, 2005, which was published in English under PCT Article 21(2), which in turn claims the benefit of U.S. Provisional Patent Application No. 60/640,672, filed Dec. 30, 2004, which is incorporated herein by reference.

FIELD

The present disclosure relates to humanized monoclonal antibodies that bind a tumor antigen. More specifically, the present disclosure relates to humanized monoclonal antibodies with amino acid substitutions in the heavy chain framework that retain binding affinity for carcinoembryonic antigen (CEA). The present disclosure also relates to humanized monoclonal antibodies with reduced immunogenicity.

BACKGROUND

Carcinoembryonic antigen (CEA) is a member of the immunoglobulin superfamily and is composed of seven domains linked to the cell membrane through a glycosylphosphatidylinositol anchor.

Anti-tumor monoclonal antibodies have much clinical potential as both therapeutic and diagnostic agents. For this reason, monoclonal antibodies raised against carcinoembryonic antigen (CEA) have been generated to detect various epitopes on CEA (Muraro et al., *Cancer Res.*, 45:5769-5780, 1985, herein incorporated by reference). These antibodies have been designated COL-1 through COL-15 (Muraro et al., *Cancer Res.*, 45:5769-5780, 1985; Ohuchi et al., *Cancer Res.* 47:3565-3571, 1987; Wilkinson et al., *Proc. Natl. Acad. Sci.* 98:10256, 2001) and have been instrumental in identifying the differential expression pattern of CEA in different tissues and in numerous carcinomas, such as gastrointestinal, colorectal, breast, ovarian, and lung carcinomas. Of these monoclonal antibodies, COL-1 is of clinical importance because it has both a high affinity for CEA and does not cross-react with other members of the immunoglobulin superfamily.

Despite the high binding affinity demonstrated by murine monoclonal antibodies, the administration of these antibodies to humans can be limited by their inherent immunogenicity and the development of a human anti-murine antibody (HAMA) response in these patients. The HAMA response can involve allergic reactions and an increased rate of clearance of the administered antibody from the serum. Many attempts have been made to design murine monoclonal antibodies that are less immunogenic to humans by "humanizing" the antibodies. Such attempts first involved the design of human-mouse chimeras, in which a murine antigen-binding variable region is coupled to a human constant domain. Other, more recent, strategies have resulted in the design of humanized antibodies with the retention of fewer murine residues. These strategies include the development of complementarity determining region (CDR)-grafted monoclonal antibodies and specificity-determining residue (SDR)-grafted monoclonal antibodies, where CDRs and/or SDRs are grafted onto the variable light ($V_L$) and/or variable heavy ($V_H$) framework (FR) of human monoclonal antibodies. Using these techniques the number of immunogenic murine residues retained in these antibodies is reduced. A few framework residues considered crucial for the maintenance of antigen binding are also grafted onto the human frameworks. These antibodies can still evoke an undesired anti-variable region response against the potentially immunogenic framework residues. Thus, there exists a need to develop a humanized COL-1 antibody with both high affinity and reduced immunogenicity for use in human subjects.

SUMMARY

The present disclosure relates to humanized COL-1 monoclonal antibodies that retain CEA binding affinity, compared to the HuCOL-1$_{AbrCDR}$ antibody. The disclosed humanized COL-1 antibodies have a variable heavy chain with an amino acid sequence as set forth in SEQ ID NO: 8 and a variable light chain, and include a substitution of a murine framework residue located at position 79 of SEQ ID NO: 8 with a residue at a corresponding Kabat position of the MO30 human antibody variable heavy chain. In one specific example, the disclosed humanized COL-1 antibodies have at least one additional heavy chain framework residue substitution. In other specific examples, the disclosed humanized COL-1 antibodies have at least five additional heavy chain framework residue substitutions. For example, the humanized COL-1 antibody can have additional framework substitutions at positions 20, 38, 48, 67, and 81 of SEQ ID NO: 8, in addition to the substitution at position 79. In another specific example, the disclosed humanized COL-1 antibodies have additional residue substitutions at positions 27 and 68 of SEQ ID NO: 8. In a further specific example, the disclosed humanized COL-1 antibodies have additional residue substitutions at positions 1, 12, 27, and 68 of SEQ ID NO: 8. Also disclosed herein are humanized COL-1 monoclonal antibodies that have reduced immunogenicity, compared to the HuCOL-1$_{AbrCDR}$ antibody.

Methods for the use of the disclosed humanized COL-1 monoclonal antibodies in the detection or treatment of a CEA-expressing tumor in a subject are described herein. Methods are also described for the treatment of a subject with the disclosed humanized COL-1 monoclonal antibodies in combination with an immunogenic agent. A kit including the antibodies disclosed herein is also described.

The foregoing and other features and advantages will become more apparent from the following detailed description of several embodiments, which proceeds with reference to the accompanying figures.

BRIEF DESCRIPTION OF THE FIGURES

FIGS. 1A and 1B are schematic representations of the humanization protocols for the murine COL-1 (mCOL-1) monoclonal antibody. FIG. 1A shows the amino acid sequences of the $V_L$ regions of mCOL-1 (SEQ ID NOL: 1), human antibody VJI'CL (SEQ ID NO: 2), HuCOL-1 derived from mCOL-1 and VJI'CL (SEQ ID NO: 3), and the HuCOL-1 variant HuCOL-1$_{AbrCDR}$ (SEQ ID NO: 4). FIG. 1B shows the amino acid sequences of the $V_H$ regions of mCOL-1 (SEQ ID NO: 5), human antibody MO30 (SEQ ID NO: 6), HuCOL-1 derived from mCOL-1 and MO30 (SEQ ID NO: 7), and the HuCOL-1 variant HuCOL-1$_{AbrCDR}$ (SEQ ID NO: 8). Dashes indicate residues that are identical in mCOL-1, human, and humanized antibodies. Asterisks mark frameworks residues that were previously thought to be essential for maintaining the combining site structure of mCOL-1. Murine frameworks residues in HuCOL-1 and HuCOL-1$_{AbrCDR}$ are shown in bold. Frameworks (FR1-FR4)

and CDRs (CDR1-CDR3) for the heavy and light chains are indicated. AbrCDR represents humanized COL-1 antibody HuCOL-1$_{AbrCDR}$.

FIGS. 2A and 2B are schematic representations of the humanization protocols for mCOL-1. FIG. 2A shows the amino acid sequences of the V$_L$ regions of human antibody VJI'CL (SEQ ID NO: 2), the HuCOL-1 variant HuCOL-1$_{AbrCDR}$ (SEQ ID NO: 4), and FRV4 (SEQ ID NO: 9), FRV7 (SEQ ID NO: 10), and FRV10 (SEQ ID NO: 11) antibodies derived from HuCOL-1$_{AbrCDR}$. FIG. 2B shows the amino acid sequences of the V$_H$ regions of human antibody MO30 (SEQ ID NO: 6), the HuCOL-1 variant HuCOL-1$_{AbrCDR}$ (SEQ ID NO: 8), and antibodies FRV4 (SEQ ID NO: 12), FRV7 (SEQ ID NO: 13), and FRV10 (SEQ ID NO: 14) derived from HuCOL-1$_{AbrCDR}$. Dashes indicate residues that are identical in mCOL-1, human and humanized antibodies. Asterisks mark frameworks residues that were previously thought to be essential for maintaining the combining site structure of mCOL-1. Murine frameworks residues in the humanized antibodies are shown in bold. Frameworks (FR1-FR4) and CDRs (CDR1-CDR3) for the heavy and light chains are indicated. AbrCDR represents humanized COL-1 antibody HuCOL-1$_{AbrCDR}$.

Figure 3A:
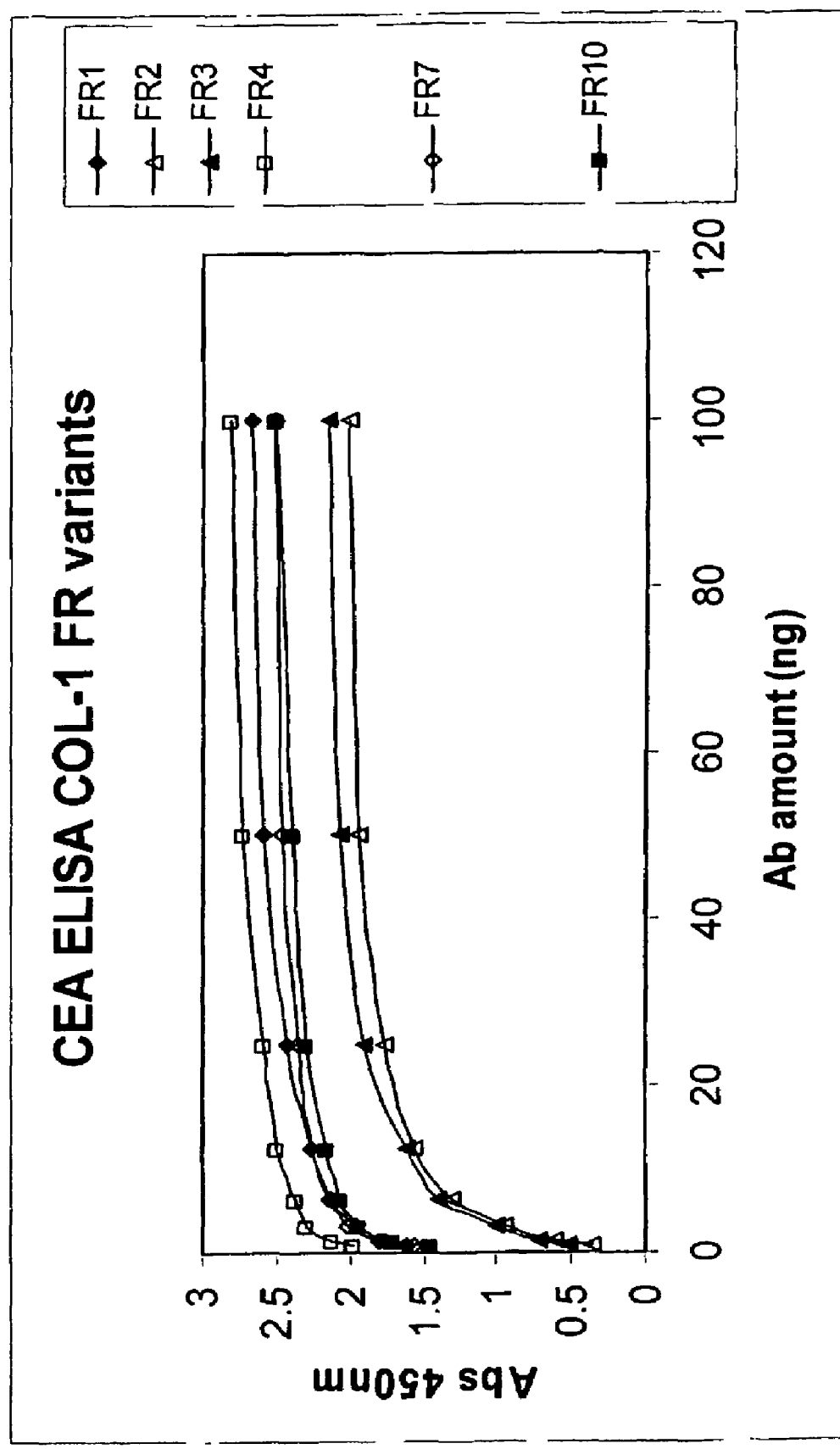
Figure 3B:
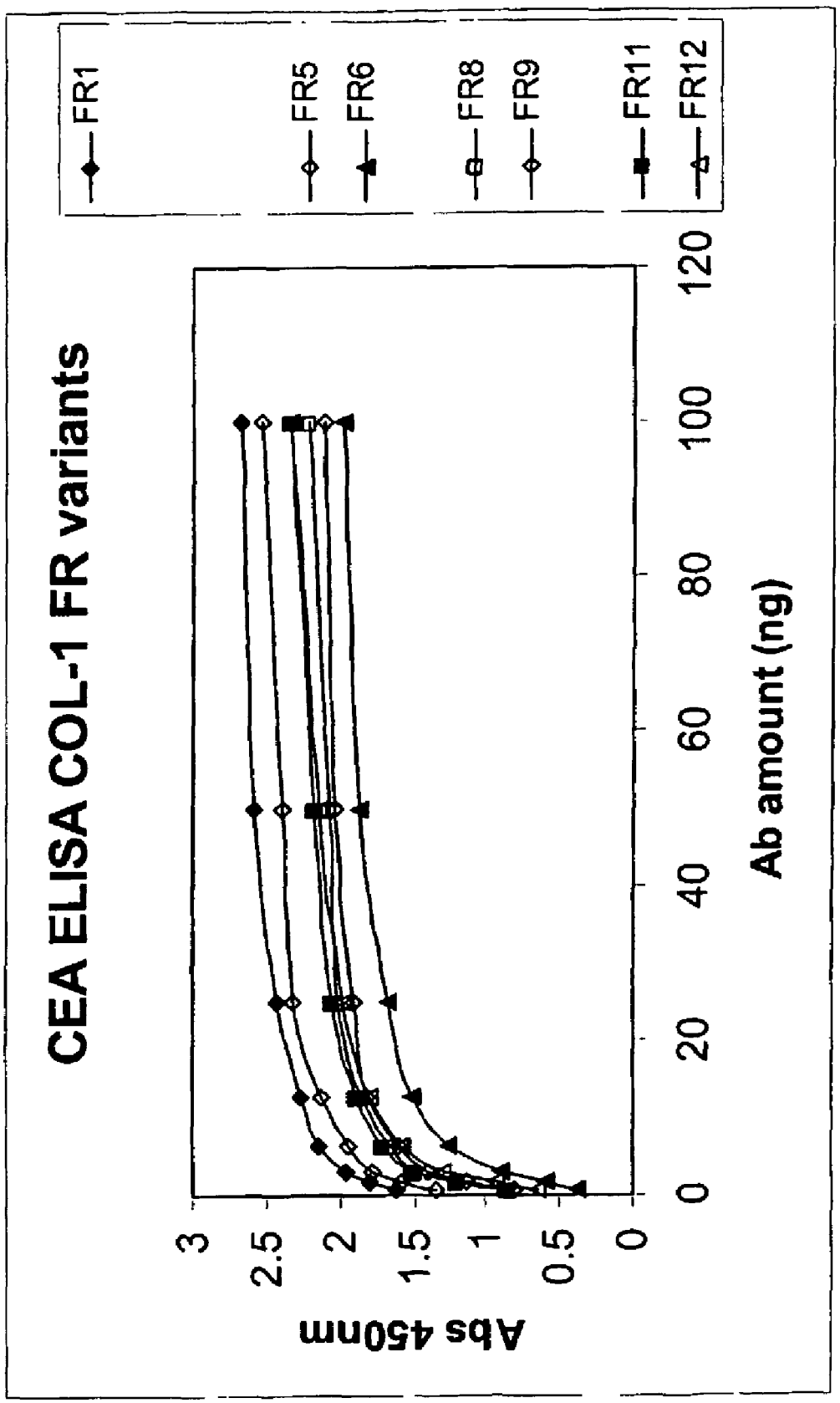

FIGS. 3A and 3B are a series of graphs of an enzyme linked immunoassay (ELISA) measuring the immunoreactivity of HuCOL-1$_{AbrCDR}$-derived antibodies to CEA. FIG. 3A compares the immunoreactivity of FRV1 (HuCOL-1$_{AbrCDR}$), FRV2, FRV3, FRV4, FRV7, and FRV10. FIG. 3B compares the immunoreactivity of FRV1, FRV5, FRV6, FRV8, FRV9, FRV11, and FRV12.

Figure 4A:
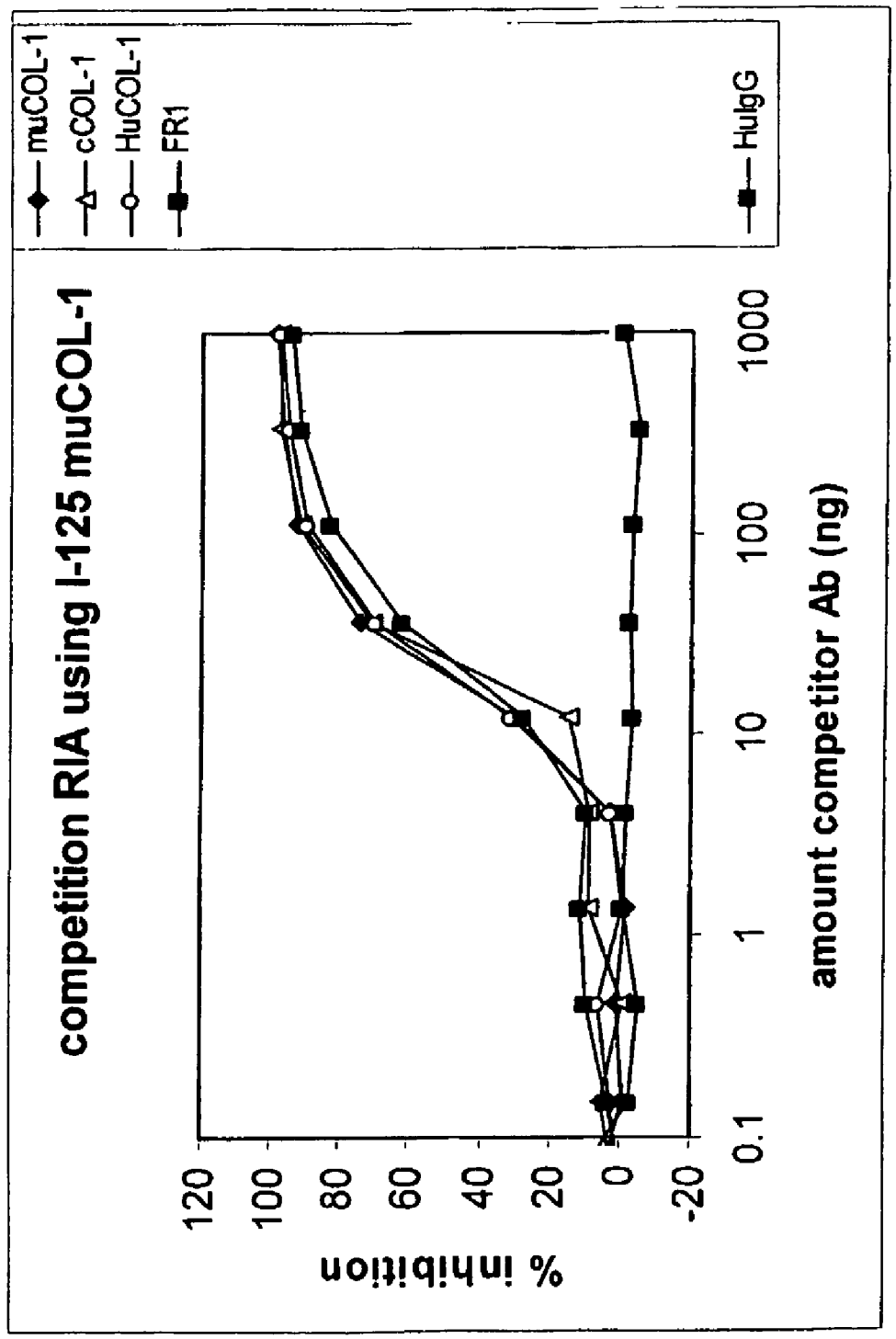
Figure 4B:
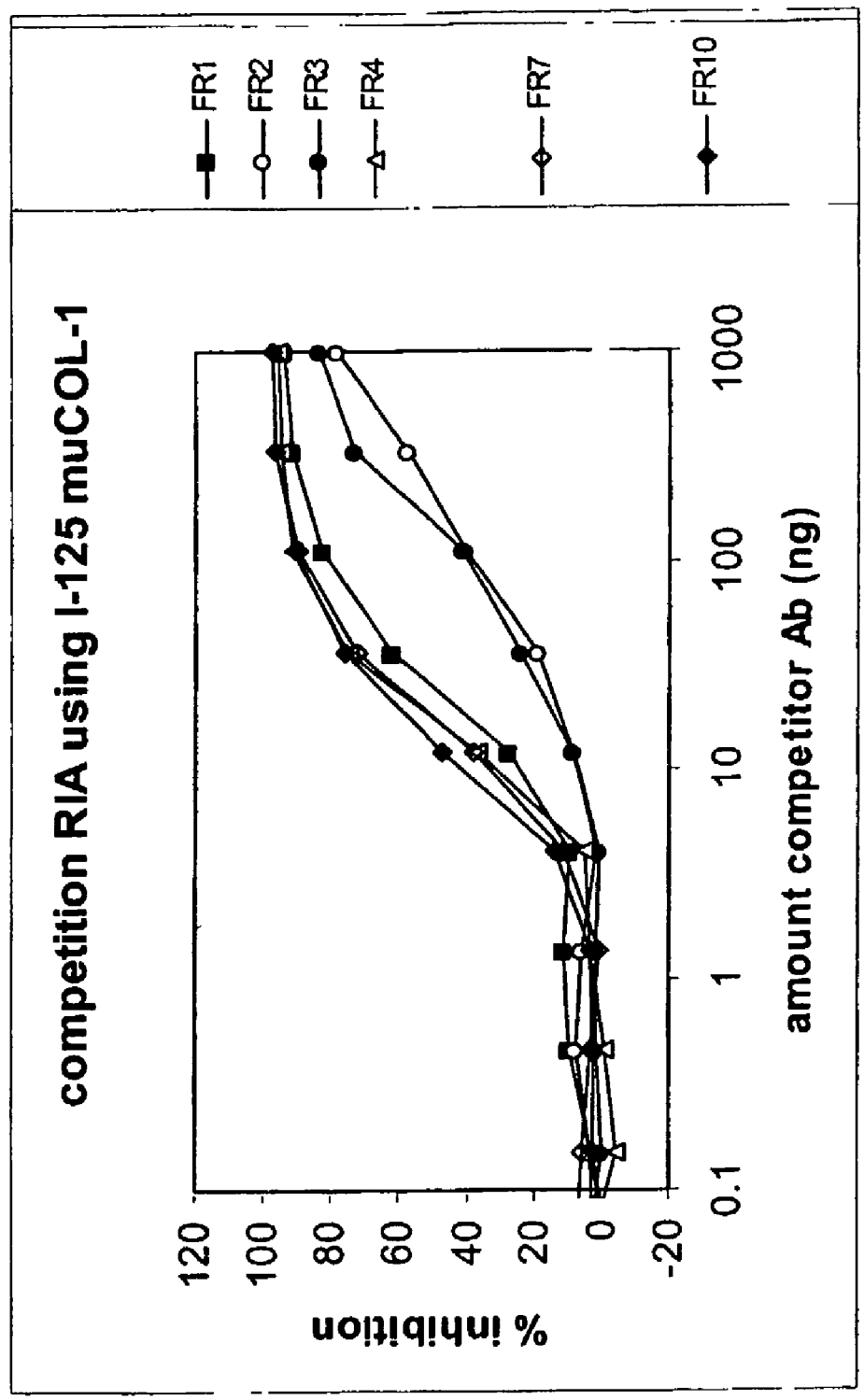
Figure 4C:
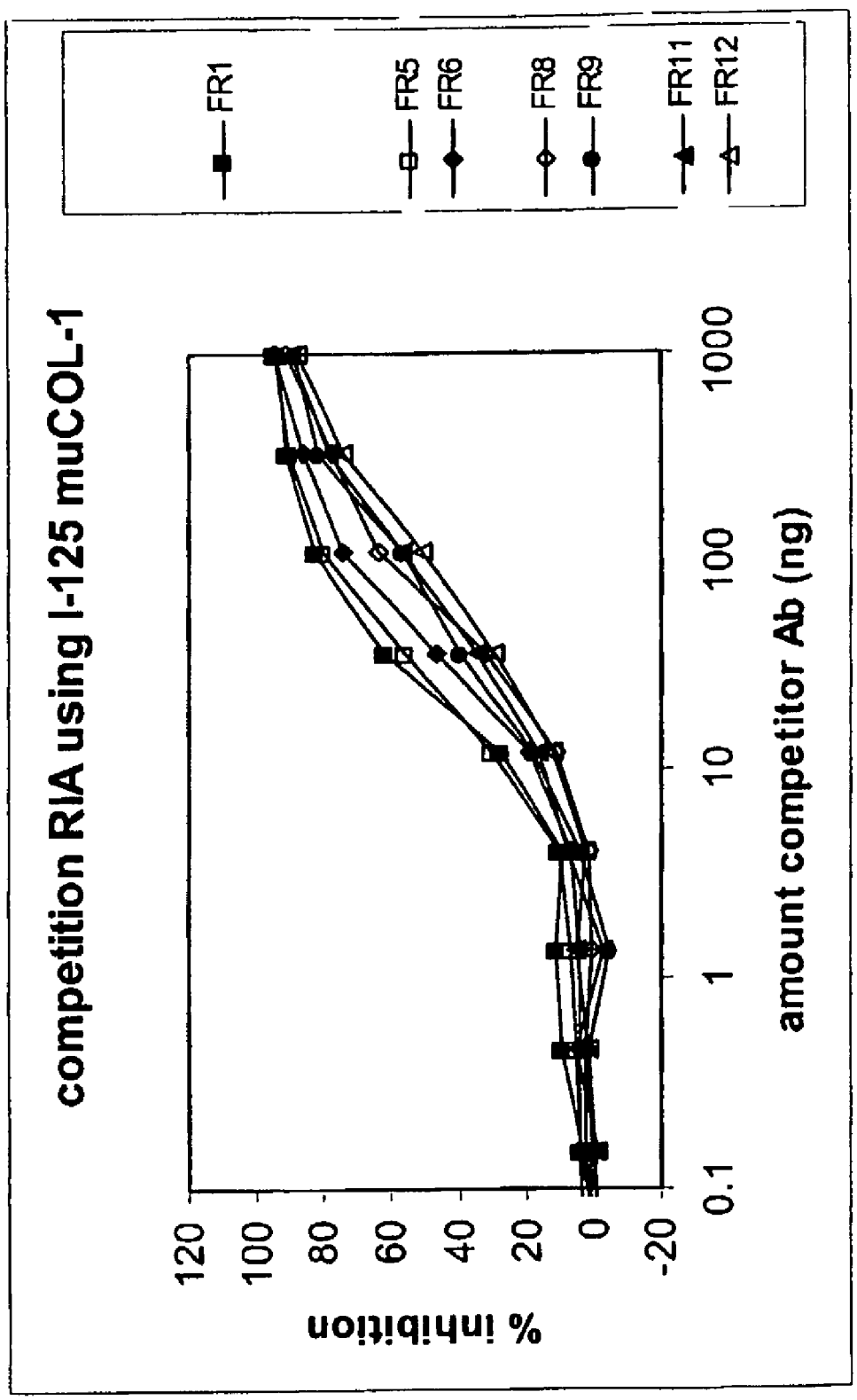

FIGS. 4A, 4B, and 4C are a series of graphs of a competition radioimmunoassay of HuCOL-1$_{AbrCDR}$ framework variants using $^{125}$I-mCOL-1. Serial dilutions of unlabeled antibodies were used to compete with the binding of $^{125}$ImCOL-1. The data was divided into three individual graphs to facilitate viewing. FIG. 4A compares the binding of unlabeled murine COL-1 (muCOL-1), chimeric COL-1 (cCOL-1), HuCOL-1, FRV1 (HuCOL-1$_{AbrCDR}$), and human IgG (HuIgG). FIG. 4B compares the binding of unlabeled murine HuCOL-1$_{AbrCDR}$, FRV2, FRV3, FRV4, FRV7, and FRV10. FIG. 4C compares the binding of unlabeled murine HuCOL-1$_{AbrCDR}$, FRV5, FRV6, FRV8, FRV9, FRV11, and FRV12.

Figure 5A:
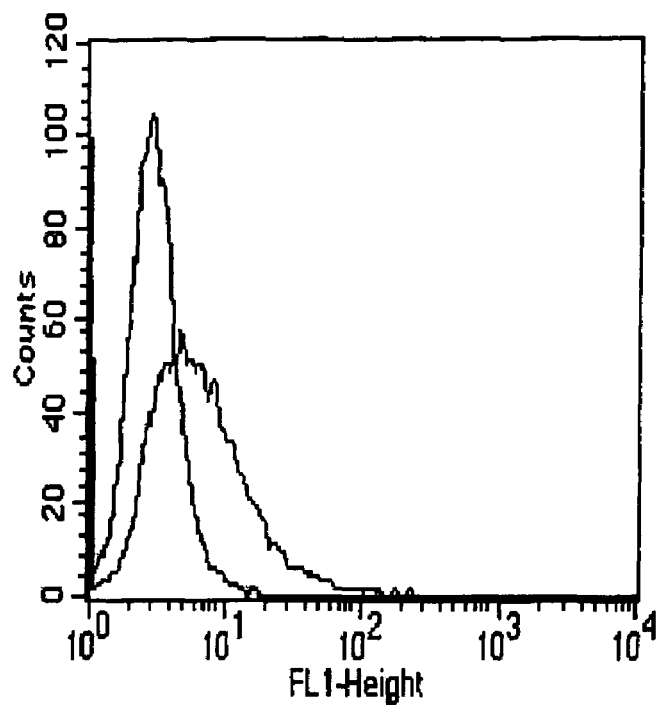
Figure 5B:
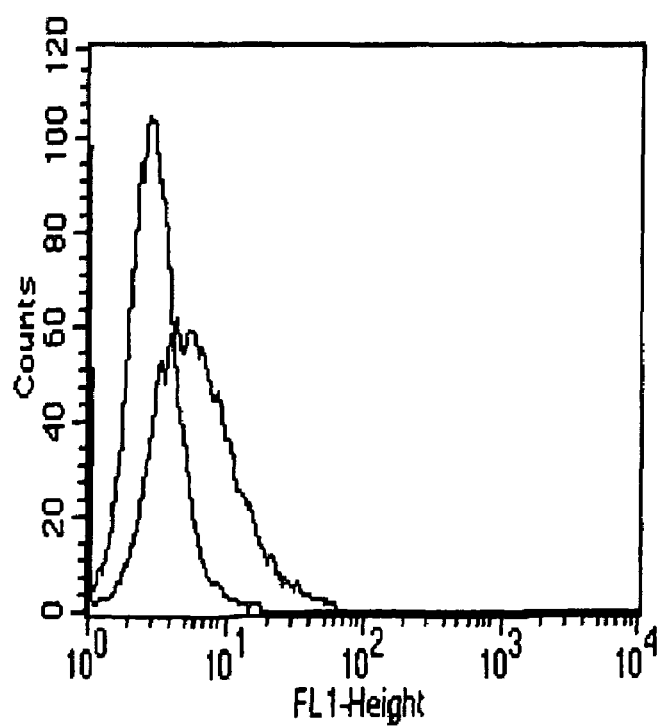
Figure 5C:
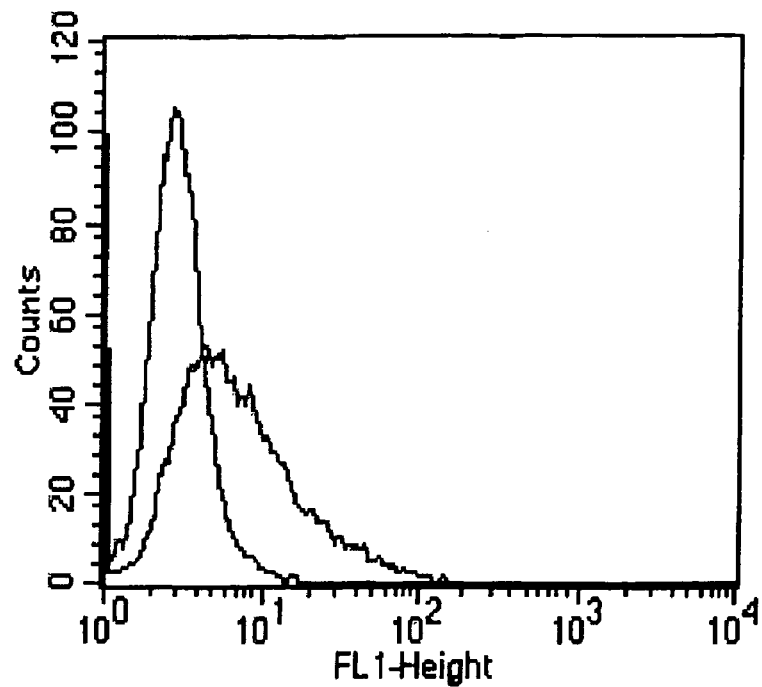
Figure 5D:
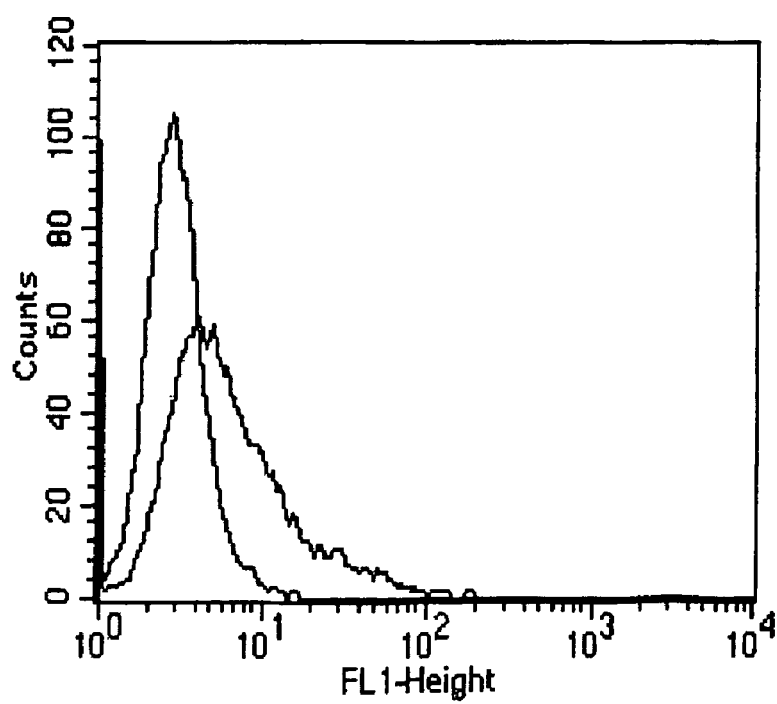

FIGS. 5A-5D are a series of binding profile graphs representing fluorescence activated cell sort (FACS). FIG. 5A represents an overlay between irrelevant antibody (human IgG) and HuCOL-1$_{AbrCDR}$, FIG. 5B represents an overlay between irrelevant antibody and FRV4, FIG. 5C represents an overlay between irrelevant antibody and FRV7, and FIG. 5D represents an overlay between irrelevant antibody and FRV10. Irrelevant antibody represent less 2% of the cell population. One microgram of each antibody was used.

Figure 6B:
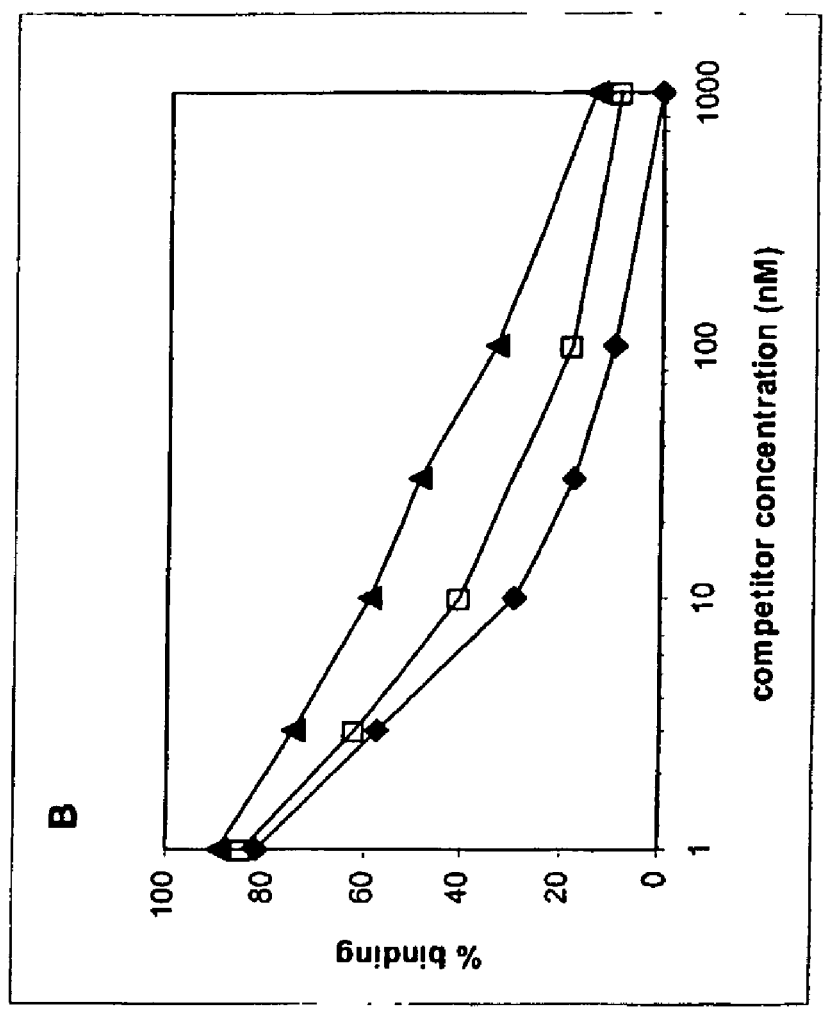

FIGS. 6A and 6B are graphs of sera reactivity, by SPR, of humanized COL-1 framework variants. Increasing concentrations of HuCOL-1 (♦), HuCOL-1$_{Abr}$ꚛ, and FRV10 (▲) antibodies were used to compete with the binding of anti-V region antibodies to COL-1 present in the sera of patients known as EM (FIG. 6A) and MB (FIG. 6B) to HuCOL-1 immobilized on a sensor chip. Percent binding was calculated from the sensorgrams and plotted as a function of competitor concentration.

FIGS. 7A and 7B are a series of graphs demonstrating the anti-tumor effect and survival of mice with combination therapy. CEA-Tg mice were injected with either MC32a (CEA+), MC38 (CEA−), or MC32 DN1Fas (defective Fas) tumor cells subcutaneously. Mice were treated with vaccine alone, with Y-90-labeled mCOL-1 antibody alone, or a combination of vaccine and mCOL-1 antibody. The TRICOM vaccine regimen consisted of a prime and boost strategy using vaccinia and fowlpox recombinants expressing CEA (rV-CEA/TRICOM and rF-CEA/TRICOM, respectively) and three costimulatory molecules (B7-1, ICAM-1, LFA-3). All of the vaccines were co-administered with rF-GM-CSF. Tumor volume (FIG. 7A) and survival (FIG. 7B) were monitored for 77 days.

SEQUENCE LISTING

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. In the accompanying sequence listing:

SEQ ID NO: 1 is the amino acid sequence of the variable light chain of the murine COL-1 monoclonal antibody.

SEQ ID NO: 2 is the amino acid sequence of the variable light chain of the human VJI'CL antibody.

SEQ ID NO: 3 is the amino acid sequence of the variable light chain of the HuCOL-1 antibody.

SEQ ID NO: 4 is the amino acid sequence of the variable light chain of the HuCOL-$1_{AbrCDR}$ antibody.

SEQ ID NO: 5 is the amino acid sequence of the variable heavy chain of the murine COL-1 monoclonal antibody.

SEQ ID NO: 6 is the amino acid sequence of the variable heavy chain of the human MO30 antibody.

SEQ ID NO: 7 is the amino acid sequence of the variable heavy chain of the HuCOL-1 antibody.

SEQ ID NO: 8 is the amino acid sequence of the variable heavy chain of the HuCOL-$1_{AbrCDR}$ antibody.

SEQ ID NO: 9 is the amino acid sequence of the variable light chain of FRV4.

SEQ ID NO: 10 is the amino acid sequence of the variable light chain of FRV7.

SEQ ID NO: 11 is the amino acid sequence of the variable light chain of FRV10.

SEQ ID NO: 12 is the amino acid sequence of the variable heavy chain of FRV4.

SEQ ID NO: 13 is the amino acid sequence of the variable heavy chain of FRV7.

SEQ ID NO: 14 is the amino acid sequence of the variable heavy chain of FRV10.

SEQ ID NO: 15 is the amino acid sequence of the variable light chain of the HuCOL-$1_{SDR}$ antibody.

SEQ ID NO: 16 is the amino acid sequence of the variable heavy chain of the HuCOL-$1_{SDR}$ antibody.

SEQ ID NOs: 17 and 18 are the amino acid sequence of a peptide.

SEQ ID NOs: 19-23 and 29 are the nucleic acid sequences of variable heavy chain 3' primers.

SEQ ID NOs: 24-28 are the nucleic acid sequences of variable heavy chain 5' primers.

DETAILED DESCRIPTION

I. Abbreviations

| | |
|---|---|
| Ab | antibody |
| Ag | antigen |
| BSM | bovine submaxillary mucin |
| C | constant |

-continued

| | |
|---|---|
| CEA | carcinoembryonic antigen |
| CH | constant heavy |
| CHO | Chinese hamster ovary |
| CL | constant light |
| CDR | complementarity determining region |
| ELISA | enzyme linked immunoassay |
| Fab | fragment antigen binding |
| F(ab')$_2$ | Fab with additional amino acids, including cysteines necessary for disulfide bonds |
| FACS | fluorescence activated cell sort |
| FR | framework region |
| Fv | fragment variable |
| H | heavy |
| HAMA | human antimurine antibody |
| HuIgG | human immunoglobulin G |
| IC$_{50}$ | half maximal inhibition of binding |
| Ig | immunoglobulin |
| IL | interleukin |
| Ka | relative affinity constant |
| L | light |
| mCOL-1 | murine COL-1 |
| PCR | polymerase chain reaction |
| PDB | protein data bank |
| RU | resonance unit |
| scFv | single chain Fv |
| SDR | specificity determining residue |
| SPR | surface plasmon resonance |
| TNF | tumor necrosis factor |
| V | variable |
| V$_H$ | variable heavy |
| V$_L$ | variable light |

II. Terms

Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of the invention, the following explanations of specific terms are provided:

Animal: Living multi-cellular vertebrate organisms, a category that includes, for example, mammals and birds. The term mammal includes both human and non-human mammals. Similarly, the term "subject" includes both human and veterinary subjects.

Antibody: Immunoglobulin (Ig) molecules and immunologically active portions of Ig molecules, for instance, molecules that contain an antigen binding site which specifically binds (immunoreacts with) an antigen.

A naturally occurring antibody (for example, IgG) includes four polypeptide chains, two heavy (H) chains and two light (L) chains interconnected by disulfide bonds. The two heavy chains are linked to each other by disulfide bonds and each heavy chain is linked to a light chain by a disulfide bond. There are two types of light chain, lambda (λ) and kappa (k). There are five main heavy chain classes (or isotypes) which determine the functional activity of an antibody molecule: IgM, IgD, IgG, IgA and IgE.

Each chain contains distinct sequence domains. The light chain includes two domains, a variable domain (V$_L$) and a constant domain (CL). The heavy chain includes four domains, a variable domain (V$_H$) and three constant domains (CH1, CH2 and CH3, collectively referred to as CH). The variable regions of both light (V$_L$) and heavy (V$_H$) chains determine binding recognition and specificity to the antigen. The constant region domains of the light (CL) and heavy (CH) chains confer important biological properties such as antibody chain association, secretion, transplacental mobility, complement binding, and binding to Fc receptors. The specificity of the antibody resides in the structural complementarity between the antibody combining site and the antigenic determinant. Antibody combining sites are made up of residues that are primarily from the hypervariable or complementarity determining regions (CDRs). However, it is believed that residues from nonhypervariable or framework regions (FR) influence the overall domain structure and hence the combining site.

It has been shown that the antigen-binding function of an antibody can be performed by fragments of a naturally occurring antibody. Thus, these antigen-binding fragments are also intended to be designated by the term "antibody." Examples of binding fragments encompassed within the term antibody include (i) an Fab fragment consisting of the V$_L$, V$_H$, CL and CH1 domains; (ii) an Fd fragment consisting of the V$_H$ and CH1 domains; (iii) an Fv fragment consisting of the V$_L$ and V$_H$ domains of a single arm of an antibody, (iv) a dAb fragment (Ward et al., *Nature* 341:544-546, 1989) which consists of a V$_H$ domain; and (v) an F(ab')$_2$ fragment, a bivalent fragment comprising two Fab fragments linked by a disulfide bridge at the hinge region. Furthermore, although the two domains of the Fv fragment are coded for by separate genes, a synthetic linker can be made that enables them to be made as a single protein chain (known as single chain Fv (scFv); (Bird et al., *Science* 242:423-426, 1988; and Huston et al., *Proc. Natl. Acad. Sci.* 85:5879-5883, 1988) by recombinant methods. Such single chain antibodies, as well as dsFv, a disulfide stabilized Fv (Bera et al., *J. Mol. Biol.* 281:475-483, 1998), and dimeric Fvs (diabodies), that are generated by pairing different polypeptide chains (Holliger et al., *Proc. Natl. Acad. Sci.* 90:6444-6448, 1993), are also included.

In one embodiment, antibody fragments for use in this disclosure are those which are capable of cross-linking their target antigen, for example, bivalent fragments such as F(ab')$_2$ fragments. Alternatively, an antibody fragment which does not itself cross-link its target antigen (for example, a Fab fragment) can be used in conjunction with a secondary antibody which serves to cross-link the antibody fragment, thereby cross-linking the target antigen. Antibodies can be fragmented using conventional techniques and the fragments screened for utility in the same manner as described for whole antibodies. An antibody is further intended to include humanized monoclonal molecules that specifically bind the target antigen.

"Specifically binds" refers to the ability of individual antibodies to specifically immunoreact with an antigen. This binding is a non-random binding reaction between an antibody molecule and the antigen. Binding specificity is typically determined from the reference point of the ability of the antibody to differentially bind the antigen of interest and an unrelated antigen, and therefore distinguish between two different antigens, particularly where the two antigens have unique epitopes. An antibody that specifically binds to a particular epitope is referred to as a "specific antibody." "Immunoreactivity" refers to a measure of the ability of an immunoglobulin to recognize and bind to a specific antigen.

In one embodiment the antigen is carcinoembryonic antigen (CEA). Monoclonal and humanized immunoglobulins are encompassed by the disclosure. In one example, a murine monoclonal antibody that recognizes the CEA antigen is COL-1. In other examples, a humanized COL-1 antibody is HuCOL-1 or HuCOL-1$_{AbrCDR}$. In yet other examples, a humanized COL-1 antibody includes a light chain derived from HuCOL-1$_{AbrCDR}$ and/or a heavy chain derived from HuCOL-1$_{AbrCDR}$. In several examples, humanized COL-1 antibodies are HuCOL-1FRV4 ("FRV4"), HuCOL-1FRV7 ("FRV7"), or HuCOL-1FRV10 ("FRV10"). The disclosure also includes synthetic and genetically engineered variants of these immunoglobulins.

Antigen: Any molecule that can bind specifically with an antibody. An antigen is also a substance that evokes immune response, including production of antibodies. Antigens are often foreign substances such as allergens, bacteria or viruses that invade the body. A specific, non-limiting example of an antigen is CEA.

Carcinoembryonic antigen (CEA): A member of the immunoglobulin superfamily that includes normal fecal antigen, non-specific cross-reacting antigen, meconium antigen, and biliary glycoprotein. CEA is composed of seven domains linked to the cell membrane through a glycosylphosphatidylinositol anchor and has a molecular weight of 180 kDa (GenBank Accession Number A36319, herein incorporated by reference). CEA is normally expressed in a variety of glandular epithelial tissues, where it appears to be localized to the apical surface of the cells, although it is also expressed in numerous carcinomas including gastrointestinal, colorectal, breast, ovarian and lung carcinomas (Robbins et al., *Int'l J. Cancer*, 53:892-897, 1993; Greiner et al., *J. Clin. Oncol.*, 10:735-746, 1992; Ohuchi et al., *Cancer Res.* 47:3565-5780, 1985; Muraro et al., *Cancer Res.*, 45:57695780, 1985). CEA is an especially well characterized human tumor antigen and is widely used for the diagnosis of human colon cancer. Monoclonal antibodies, designated COL-1 through COL-15, have been generated to detect various epitopes on CEA (Muraro et al., *Cancer Res.*, 45:5769-5780, 1985, herein incorporated by reference), and in using these antibodies the differential expression of CEA has been determined (Muraro et al., *Cancer Res.*, 45:5769-5780, 1985; Ohuchi et al., *Cancer Res.* 47:3565-3571, 1987; Wilkinson et al., *Proc. Natl. Acad. Sci.* 98:10256, 2001). Of these monoclonal antibodies, COL-1 is of clinical importance because it has a high affinity for CEA.

cDNA (complementary DNA): A piece of DNA lacking internal, non-coding segments (introns) and regulatory sequences that determine transcription. cDNA is synthesized in the laboratory by reverse transcription from messenger RNA extracted from cells.

CEA binding affinity: Affinity of an antibody for CEA. In one embodiment, CEA binding affinity is calculated by a modification of the Scatchard method described by Frankel et al. (*Mol. Immunol.*, 16:101-106, 1979). One of skill in the art can readily identify a statistical test that determines a statistically significant result, for example, the Student's t-test, the Wilcoxon two sample test, or the Median test. In one embodiment, a humanized COL-1 antibody, such as an antibody derived from HuCOL-1$_{AbrCDR}$ (for example, FRV4, FRV7, or FRV10) retains CEA binding affinity when CEA binding affinity is similar to or is increased as compared to a COL-1 antibody, for example mCOL-1, HuCOL-1, or HuCOL-1$_{AbrCDR}$. In another embodiment, a humanized COL-1 antibody retains CEA binding affinity when CEA binding affinity is at least about $2.0 \times 10^{-8}$ M. In other embodiments, the humanized COL-1 antibody retains CEA binding affinity when CEA binding affinity is at least about $2.5 \times 10^{-8}$, about $3.0 \times 10^{-8}$, about $3.5 \times 10^{-8}$, about $4.0 \times 10^{-8}$, about $4.5 \times 10^{-8}$, about $5.0 \times 10^{-8}$ M or greater.

In another embodiment, a CEA binding affinity is measured by an antigen/antibody dissociation rate of a humanized COL-1 antibody. A humanized COL-1 antibody, such as an antibody derived from HuCOL-1$_{AbrCDR}$ (for example, FRV4, FRV7, or FRV10) retains CEA binding affinity when the antigen/antibody dissociation rate is equal to or lower than the parent antibody. In yet another embodiment, a CEA binding affinity is measured by a competition radioimmunoassay. CEA binding affinity is retained when the amount of a humanized COL-1 antibody needed for 50% inhibition of the binding of $^{125}$I-labeled HuCOL-1 antibody to BSM is less than that required by the parent antibody. In another embodiment, a CEA binding affinity is measured by flow cytometry. CEA binding affinity is retained when the number of gated cells labeled with humanized COL-1 antibody is the same or greater than the number of gated cells labeled by the parent antibody.

Chimeric antibody: An antibody which includes sequences derived from two different antibodies, which typically are of different species. Most typically, chimeric antibodies include human and murine antibody domains, generally human constant regions and murine variable regions (including murine CDRs and/or murine SDRs).

Complementarity Determining Region (CDR): Amino acid sequences which together define the binding affinity and specificity of the natural Fv region of a native Ig binding site. The light and heavy chains of an Ig each have three CDRs, designated L-CDR1, L-CDR2, L-CDR3 and H-CDR1, H-CDR2, H-CDR3, respectively. The CDRs of the light chain are bounded by the residues at positions 24 and 34 (L-CDR1), 50 and 56 (L-CDR2), 89 and 97 (L-CDR3); the CDRs of the heavy chain are bounded by the residues at positions 31 and 35b (H-CDR1), 50 and 65 (H-CDR2), 95 and 102 (H-CDR3), using the numbering convention delineated by Kabat et al., (1991) *Sequences of Proteins of Immunological Interest*, 5$^{th}$ Edition, Department of Health and Human Services, Public Health Service, National Institutes of Health, Bethesda (NIH Publication No. 91-3242).

Cytotoxin: An agent that is toxic for cells. Examples of cytotoxins include radioactive isotopes, chemotherapeutic drugs, bacterial toxins, viral toxins, and proteins contained in venom (for example, insect, reptile, or amphibian venom). A cytokine, such as interleukin-2 or interferon, can also be a cytotoxin.

Diagnostically effective amount: A quantity of a specific substance sufficient to achieve a desired effect in a subject or tissue being diagnosed. For instance, this can be the amount necessary to detect the presence of a tumor or a tumor cell. In one embodiment, a diagnostically effective amount is the amount necessary to detect a tumor expressing CEA. When administered to a subject, a dosage will generally be used that will achieve target tissue concentrations (for example, in tumors) that has been shown to achieve a desired in vitro effect.

DNA: Deoxyribonucleic acid. DNA is a long chain polymer which constitutes the genetic material of most living organisms (some viruses have genes composed of ribonucleic acid (RNA)). The repeating units in DNA polymers are four different nucleotides, each of which contains one of the four bases, adenine, guanine, cytosine and thymine bound to a deoxyribose sugar to which a phosphate group is attached. Triplets of nucleotides (referred to as codons) code for each amino acid in a polypeptide. The term codon is also used for the corresponding (and complementary) sequence of three nucleotides in the mRNA that is transcribed from the DNA.

Effector Molecule: Therapeutic, diagnostic, or detection moieties linked to an antibody, such as HuCOL-1, HuCOL-1$_{AbrCDR}$, or antibodies derived from HuCOL-1$_{AbrCDR}$ (for example, FRV4, FRV7, or FRV10), using any number of means known to those of skill in the art. Both covalent and noncovalent linkage means may be used. The procedure for linking an effector molecule to an antibody varies according to the chemical structure of the effector. Polypeptides typically contain a variety of functional groups; for example, carboxylic acid (COOH), free amino (—NH$_2$) or sulfhydryl (—SH) groups, which are available for reaction with a suitable functional group on an antibody to result in the linkage of the effector molecule. Alternatively, the antibody is derivatized to expose or link additional reactive functional groups. The derivatization may involve linkage of any of a number of linker molecules, such as those available from Pierce Chemical Company, Rockford, Ill. The linker can be any molecule used to join the antibody to the effector molecule. The linker is capable of forming covalent bonds to both the antibody and to the effector molecule. Suitable linkers are well known to those of skill in the art and include, but are not limited to, straight or branched-chain carbon linkers, heterocyclic carbon linkers, or peptide linkers. Where the antibody and the effector molecule are polypeptides, the linkers may be joined to the constituent amino acids through their side groups (for example, through a disulfide linkage to cysteine) or to the alpha carbon amino and carboxyl groups of the terminal amino acids.

An "immunoconjugate" is a covalent linkage of an effector molecule, such as a toxin, a chemical compound, or a detectable label, to an antibody. Specific, non-limiting examples of toxins include, but are not limited to, abrin, ricin, *Pseudomonas* exotoxin (such as PE35, PE37, PE38, and PE40), diphtheria toxin, anthrax toxin, botulinum toxin, or modified toxins thereof. For example, *Pseudomonas* exotoxin and diphtheria toxin are highly toxic compounds that typically bring about death through liver toxicity. *Pseudomonas* exotoxin and diphtheria toxin, however, can be modified into a form for use as an immunotoxin by removing the native targeting component of the toxin (for example, domain Ia of *Pseudomonas* exotoxin and the B chain of diphtheria toxin) and replacing it with a different targeting moiety, such as an antibody. Other toxic agents, that directly or indirectly inhibit cell growth or kill cells, include chemotherapeutic drugs, cytokines, for example interleukin (IL)-2, IL-4, IL-10, tumor necrosis factor-alpha, or interferon-gamma, radioactive isotopes, viral toxins, or proteins contained within, for example, insect, reptile, or amphibian venom. Specific, non-limiting examples of detectable labels include, but are not limited to, radioactive isotopes, enzyme substrates, co-factors, ligands, chemiluminescent agents, fluorescent agents, haptens, or enzymes.

In one embodiment, an antibody is joined to an effector molecule. In another embodiment, an antibody joined to an effector molecule is further joined to a lipid or other molecule to a protein or peptide to increase its half-life in the antibody. The linkage can be, for example, either by chemical or recombinant means. In one embodiment, the linkage is chemical, wherein a reaction between the antibody moiety and the effector molecule has produced a covalent bond formed between the two molecules to form one molecule. A peptide linker (short peptide sequence) can optionally be included between the antibody and the effector molecule.

In some circumstances, it is desirable to free the effector molecule from the antibody when the immunoconjugate has reached its target site. Therefore, in these circumstances, immunoconjugates will comprise linkages that are cleavable in the vicinity of the target site. Cleavage of the linker to release the effector molecule from the antibody may be prompted by enzymatic activity or conditions to which the immunoconjugate is subjected either inside the target cell or in the vicinity of the target site. When the target site is a tumor, a linker which is cleavable under conditions present at the tumor site (for example, when exposed to tumor-associated enzymes or acidic pH) may be used.

In view of the large number of methods that have been reported for linking a variety of radiodiagnostic compounds, radiotherapeutic compounds, label (for example, enzymes or fluorescent molecules) drugs, toxins, and other agents to antibodies one skilled in the art will be able to determine a suitable method for linking a given agent to an antibody.

Encode: A polynucleotide is said to "encode" a polypeptide if, in its native state or when manipulated by methods well known to those skilled in the art, it can be transcribed and/or translated to produce the mRNA for and/or the polypeptide or a fragment thereof. The anti-sense strand is the complement of such a nucleic acid, and the encoding sequence can be deduced therefrom.

Epitope: A site on an antigen recognized by an antibody, as determined by the specificity of the antibody amino acid sequence. Epitopes are also called antigenic determinants.

Framework Region: Amino acid sequences interposed between CDRs.

Antibody framework region includes variable light and variable heavy framework regions. The framework regions serve to hold the CDRs in an appropriate orientation for antigen binding. The light and heavy chains of an Ig each have four framework regions, designated FR1, FR2, FR3 and FR4 for both the light and heavy chains. The numbering of the residues in the light chain and heavy chain framework regions follows the numbering convention delineated by Kabat et al. (1991, supra).

Human anti-murine antibody (HAMA) response: An immune response in a human subject against a murine antibody, or an antibody including murine components (for example, CDRs, SDRs, or framework residues) that has been administered to the subject. Repeated antibody administration may lead to an increased rate of clearance of the antibody from the patient's serum and may also elicit allergic reactions in the subject.

Humanized antibody: A human antibody genetically engineered to include mouse hypervariable regions, CDRs and/or SDRs. In one embodiment, the DNA encoding hypervariable loops of mouse monoclonal antibodies or variable regions selected in phage display libraries is inserted into the framework regions of human Ig genes. Antibodies can be "customized" to have a desired binding affinity or to be minimally immunogenic in the humans treated with them.

Humanized COL-1 antibodies: COL-1 antibodies humanized by grafting mCOL-1 (murine COL-1) residues (for example, CDRs, SDRs, or framework residues) onto the frameworks of the relevant human antibodies. mCOL-1 CDRs include synthetic amino acid sequences that are identical in sequence to the native mCOL-1 CDRs or that include one or more amino acid substitutions. COL-1 can be humanized by grafting only a subset of the COL-1 CDR residues, for example a partial or "abbreviated" CDR, as in HuCOL-1$_{AbrCDR}$ (see below), or only those residues that are important for antigen binding (ligand contact residues or SDRs), onto the variable light and variable heavy framework regions of human antibody sequences. Examples of human antibody sequences include VJI'CL or MO30.

In one embodiment of a humanized COL-1 antibody, COL-1 CDR residues that are not involved in antigen binding (non-ligand contact residues or non-SDRs) are substituted with the corresponding residues of a human antibody. In another embodiment of a humanized COL-1 antibody, COL-1 framework residues are substituted with the corresponding residues of a human antibody framework. A limited number of murine non-ligand contact residues or framework residues are included in a humanized COL-1 antibody. In one embodiment, no murine resides are included in the framework region. In other embodiments, at most about one, two, three, four, five, six, seven, eight, nine, ten, eleven, twelve, thirteen, fourteen, fifteen, sixteen. or twenty murine amino acids are included in the human framework.

In other embodiments of a humanized COL-1 antibody, one or more murine CDRs, one or more murine SDRs, one or more murine non-ligand contact residues, one or more murine framework residues, or any combination thereof, are substituted with the corresponding amino acid(s) from a human antibody sequence.

A specific humanized COL-1 monoclonal antibody, termed HuCOL-1, has been deposited with ATCC as PTA-4661, in accordance with the Budapest treaty. HuCOL-1was generated by grafting all six (three heavy chain and three light chain) monoclonal antibody COL-1 hypervariable regions (CDRs) onto the variable light ($V_L$) and variable heavy ($V_H$) frameworks of the human antibodies VJI'CL and MO30, respectively, while retaining murine framework residues that may be required for the integrity of the antigen combining site structure (FIG. 1, SEQ ID NOs: 3 and 7). Another specific humanized COL-1 antibody, HuCOL-1$_{AbrCDR}$ (also referred to as HuCOL-1$^{24,25,27}$L/$^{61}$H), has been deposited with ATCC as PTA-4644. ATCC Accesssion number PTA-4644 was deposited in the American Type Culture Collection (10801 University Boulevard, Manassas, Va. 20110-2209) on Sep. 5, 2002. HuCOL-1$_{AbrCDR}$ was generated by grafting partial or "abbreviated" CDRs onto the $V_L$ and $V_H$ frameworks of VJI'CL and MO30, respectively (FIG. 1, SEQ ID NOs: 4 and 8). HuCOL-1$_{AbrCDR}$, and HuCOL-1 are described in De Pascalis et al. (*J Immunol*, 169:3076-3084, 2002) and International Patent Application No. PCT/US03/27976, both of which are incorporated herein by reference. These documents also disclose the amino acid sequences of mCOL-1, MO30 and VJI'CL. Yet another specific humanized COL-1 antibody, HuCOL-1$_{SDR}$, was formed by identifying the most homologous human germline sequences for each murine CDR and framework region, and grafting essential murine SDRs and framework residues onto the human sequences. The variable light chain of HuCOL-1$_{SDR}$ is encoded by SEQ ID NO: 15 and the variable heavy chain of HuCOL-1$_{SDR}$ is encoded by SEQ ID NO: 16. For the purposes of this disclosure, HuCOL-1 $_{AbrCDR}$ is referred to as the parental antibody.

The humanized COL-1 antibodies disclosed herein include humanized COL-1 antibodies, such as HuCOL-1, HuCOL-1$_{SDR}$, or HuCOL-1$_{AbrCDR}$, having additional amino acid substitutions. Examples of such humanized COL-1 monoclonal antibodies include antibodies derived from HuCOL-1$_{AbrCDR}$, such as FRV4, FRV7, or FRV10.

Idiotype: The property of a group of antibodies or T cell receptors defined by their sharing a particular idiotope (an antigenic determinant on the variable region); for instance, antibodies that share a particular idiotope belong to the same idiotype. "Idiotype" may be used to describe the collection of idiotopes expressed by an Ig molecule. An "anti-idiotype" antibody may be prepared to a monoclonal antibody by methods known to those of skill in the art and may be used to prepare pharmaceutical compositions.

Immune cell: Any cell involved in a host defense mechanism. These can include, for example, T cells, B cells, natural killer cells, neutrophils, mast cells, macrophages, antigen-presenting cells, basophils, eosinophils, and neutrophils.

Immune response: A response of a cell of the immune system, such as a neutrophil, a B cell, or a T cell, to a stimulus. In one embodiment, the response is specific for a particular antigen (an "antigen-specific response"). In another embodiment, the response is against an antibody, such as a HAMA response, including an anti-variable region response.

Immunogenic agent: An agent that has a stimulatory effect on at least one component of the immune response, thereby causing or enhancing an immune response. In some embodiments, the immune response provides protective immunity, in that it enables the subject to prevent the establishment of a tumor, suppresses further growth of an existing tumor, or reduce the size of an existing tumor, for instance. Without wishing to be bound by a particular theory, it is believed that an immunogenic response may arise from the generation of neutralizing antibodies, T-helper, or cytotoxic cells of the immune system, or all of the above. In some instances, an immunogenic agent is referred to as a vaccine.

In some embodiments, an "effective amount" or "immune-stimulatory amount" of an immunogenic agent, or a composition including an immunogenic agent, is an amount which, when administered to a subject, is sufficient to engender a detectable immune response. Such a response may comprise, for instance, generation of an antibody specific to one or more of the epitopes provided by the immunogenic agent, for example CEA. Alternatively, the response may comprise a T-helper or CTL-based response to one or more of the epitopes provided by the immunogenic agent, for example CEA. All three of these responses may originate from naïve or memory cells. In other embodiments, a "protective effective amount" of an immunogenic agent, or a composition including an immunogenic agent, is an amount which, when administered to a subject, is sufficient to confer protective immunity upon the subject. In further embodiments, a "therapeutic effective amount" of an immunogenic agent, or a composition including an immunogenic agent, is an amount which, when administered to a subject, is sufficient to confer therapeutic immunity upon the subject.

Immunogenicity: A measure of the ability of a targeting protein or therapeutic moiety, such as an antibody, to elicit an immune response (humoral or cellular) when administered to a subject. An antibody that generates a reduced, for example low, immune response when administered to a subject, such as a human subject, is "minimally immunogenic."

In one embodiment, immunogenicity is measured by a competitive binding assay. A competitive binding assay measures the ability of a humanized COL-1 antibody, such as an antibody derived from HuCOL-1$_{AbrCDR}$ (for example FRV4, FRV7, or FRV10) to prevent a parental antibody from binding to COL-1 anti-idiotypic antibodies in a patient's serum. For example, if a humanized COL-1 antibody competes with an equal molar amount of the parental antibody (for instance, elicits greater than about 50% inhibition of parental antibody binding to anti-idiotypic antibodies in a patient's serum) then the humanized COL-1 antibody is immunogenic. In another example, if a humanized COL-1 antibody competes poorly with an equal molar or less amount of the parental antibody (for instance, elicits about 50% or less inhibition of parental antibody binding to anti-idiotypic antibodies in a patient's serum) then the humanized COL-1 antibody, such as FRV4, FRV7, or FRV10, is minimally immunogenic. In another embodiment, if a five-fold or greater molar concentration of a humanized COL-1 antibody is required to achieve about 50% inhibition of binding of the parental antibody to its cognate anti-idiotypic antibodies present in a subject's sera, then the humanized antibody is minimally immunogenic.

In one example, a humanized antibody, such as, but not limited to, FRV4, FRV7, or FRV10, has minimal immunogenicity (compared to mCOL-1, HuCOL-1, and/or HuCOL-1$_{AbrCDR}$). In one example reduced or minimal immunogenicity, as compared to a parental antibody, is an $IC_{50}$ value at least about a 2-fold, 5-fold, 10-fold, 20-fold, 25-fold, 30-fold, or 35-fold higher than that of a parental antibody. However, other assays can be used to measure immunogenicity.

Isolated: An biological component (such as a nucleic acid, peptide or protein) that has been substantially separated, produced apart from, or purified away from other biological components in the cell of the organism in which the component naturally occurs, for instance, other chromosomal and extrachromosomal DNA and RNA, and proteins. Nucleic acids, peptides and proteins that have been "isolated" thus include nucleic acids and proteins purified by standard purification methods. The term also embraces nucleic acids, peptides and proteins prepared by recombinant expression in a host cell as well as chemically synthesized nucleic acids.

An isolated, or substantially purified, biological component as used herein refers to a biological component that is substantially free of other components, such as proteins, lipids, carbohydrates or other materials with which it is naturally associated. In one embodiment, the biological component is at least 50%, for example at least 80% free of other components or materials with which it is naturally associated. In another embodiment, the biological component is at least 90% free of other components or materials with which it is naturally associated. In yet another embodiment, the biological component is at least 95% free of other components or materials with which it is naturally associated.

Kabat position: A position of a residue in an amino acid sequence that follows the numbering convention delineated by Kabat et al. (*Sequences of Proteins of Immunological Interest*, 5<sup>th</sup> Edition, Department of Health and Human Services, Public Health Service, National Institutes of Health, Bethesda, NIH Publication No. 91-3242, 1991).

Label: A detectable compound or composition that is conjugated directly or indirectly to another molecule to facilitate detection of that molecule. Specific, non-limiting examples of labels include fluorescent tags, chemiluminescent tags, haptens, enzymatic linkages, and radioactive isotopes.

Ligand contact residue or Specificity Determining Residue (SDR): A residue within a CDR that is involved in contact with a ligand or antigen. A ligand contact residue is also known as a specificity determining residue (SDR). A non-ligand contact residue is a residue in a CDR that does not contact a ligand.

Lymphocytes: A type of white blood cell that is involved in the immune defenses of the body. There are two main types of lymphocytes: B cells and T cells.

Mammal: This term includes both human and non-human mammals. Similarly, the term "subject" includes both human and veterinary subjects.

Monoclonal antibody: An antibody produced by a single clone of B-lymphocytes. Monoclonal antibodies are produced by methods known to those of skill in the art, for instance by making hybrid antibody-forming cells from a fusion of myeloma cells with immune spleen cells.

Nucleic acid: A deoxyribonucleotide or ribonucleotide polymer in either single or double stranded form, and unless otherwise limited, encompasses known analogues of natural nucleotides that hybridize to nucleic acids in a manner similar to naturally occurring nucleotides.

Oligonucleotide: A linear single-stranded polynucleotide sequence of up to about 200 nucleotide bases in length, for example a polymer of deoxyribonucleotides or ribonucleotides which is at least 6 nucleotides, for example at least 15, 50, 100 or even 200 nucleotides long.

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein coding regions, in the same reading frame.

Pharmaceutical agent: A chemical compound or composition capable of inducing a desired therapeutic or prophylactic effect when properly administered to a subject or a cell. "Incubating" includes a sufficient amount of time for a drug to interact with a cell. "Contacting" includes incubating a drug in solid or in liquid form with a cell.

A "therapeutically effective amount" is a quantity of a specific substance sufficient to achieve a desired effect in a subject being treated. For instance, this can be the amount necessary to inhibit or suppress growth of a tumor or to decrease a sign or symptom of the tumor in the subject without eliciting a HAMA response. In one embodiment, a therapeutically effective amount is the amount necessary to eliminate a tumor without eliciting a HAMA response. When administered to a subject, a dosage can be used that will achieve target tissue concentrations (for example, in tumors) that has been shown to achieve a desired in vitro effect.

Pharmaceutically acceptable carriers: The pharmaceutically acceptable carriers useful in this disclosure are conventional. *Remington's Pharmaceutical Sciences*, by E. W. Martin, Mack Publishing Co., Easton, Pa., 15<sup>th</sup> Edition (1975), describes compositions and formulations suitable for pharmaceutical delivery of humanized COL-1 monoclonal antibodies disclosed herein.

In general, the nature of the carrier will depend on the particular mode of administration employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (for example, powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Polynucleotide: A single-stranded linear nucleotide sequence, including sequences of greater than 100 nucleotide bases in length.

Polypeptide: A polymer in which the monomers are amino acid residues that are joined together through amide bonds. When the amino acids are alpha-amino acids, either the L-optical isomer or the D-optical isomer can be used, the L-isomers being preferred in nature. The term polypeptide or protein as used herein encompasses any amino acid sequence and includes, but may not be limited to, modified sequences such as glycoproteins. The term polypeptide is specifically intended to cover naturally occurring proteins, as well as those that are recombinantly or synthetically produced.

Conservative amino acid substitution tables providing functionally similar amino acids are well known to one of ordinary skill in the art. The following six groups are examples of amino acids that are considered to be conservative substitutions for one another:

1) Alanine (A), Serine (S), Threonine (T);
2) Aspartic acid (D), Glutamic acid (E);
3) Asparagine (N), Glutamine (Q);

4) Arginine (R), Lysine (K);
5) Isoleucine (I), Leucine (L), Methionine (M), Valine (V); and
6) Phenylalanine (F), Tyrosine (Y), Tryptophan (W).

A non-conservative amino acid substitution can result from changes in: (a) the structure of the amino acid backbone in the area of the substitution; (b) the charge or hydrophobicity of the amino acid; or (c) the bulk of an amino acid side chain. Substitutions generally expected to produce the greatest changes in protein properties are those in which: (a) a hydrophilic residue is substituted for (or by) a hydrophobic residue; (b) a proline is substituted for (or by) any other residue; (c) a residue having a bulky side chain, for example, phenylalanine, is substituted for (or by) one not having a side chain, for example, glycine; or (d) a residue having an electropositive side chain, for example, lysyl, arginyl, or histadyl, is substituted for (or by) an electronegative residue, for example, glutamyl or aspartyl.

Preventing or treating a disease: Preventing a disease refers to inhibiting completely or in part the development or progression of a disease, for example in a person who is known to have a predisposition to a disease, such as a CEA-expressing tumor, for example a colorectal, breast, ovarian, or prostate cancer. An example of a person with a known predisposition is someone with a history of cancer in the family, or who has been exposed to factors that predispose the subject to the development of a tumor. Treating a disease refers to a therapeutic intervention that inhibits, or suppresses the growth of a tumor, eliminates a tumor, ameliorates at least one sign or symptom of a disease or pathological condition, or interferes with a pathophysiological process, after the disease or pathological condition has begun to develop.

Protein: A biological molecule encoded by a gene and comprised of amino acids.

Recombinant: A recombinant nucleic acid is one that has a sequence that is not naturally occurring or was made artificially. Artificial combination is often accomplished by chemical synthesis or, more commonly, by the artificial manipulation of isolated segments of nucleic acids, for example, by genetic engineering techniques. Similarly, a recombinant protein is one encoded by a recombinant nucleic acid molecule.

Sequence identity: The similarity between two nucleic acid sequences, or two amino acid sequences, is expressed in terms of the similarity between the sequences, otherwise referred to as sequence identity. Sequence identity is frequently measured in terms of percentage identity (or similarity or homology); the higher the percentage, the more similar the two sequences are. One amino acid sequence can be, for example, 80%, 90%, 95%, 98%, or 99% identical to a second amino acid sequence, such as a native amino acid sequence. One nucleic acid sequence can be, for example, 80%, 90%, 95%, 98%, or 99% identical to a second nucleic acid sequence, such as a native nucleic acid sequence. Programs and algorithms for determining percentage identity can be found at the NCBI website.

Methods of alignment of sequences for comparison are well known in the art. Various programs and alignment algorithms are described in: Smith & Waterman *Adv. Appl. Math.* 2: 482, 1981; Needleman & Wunsch *J. Mol. Biol.* 48: 443, 1970; Pearson & Lipman *Proc. Natl. Acad. Sci. USA* 85: 2444, 1988; Higgins & Sharp *Gene,* 73: 237-244, 1988; Higgins & Sharp *CABIOS* 5: 151-153, 1989; Corpet et al. *Nuc. Acids Res.* 16, 10881-90, 1988; Huang et al. *Computer Appls. in the Biosciences* 8, 155-65, 1992; and Pearson et al. *Meth. Mol. Bio.* 24, 307-31, 1994. Altschul et al. (*J. Mol. Biol.* 215:403-410, 1990), presents a detailed consideration of sequence alignment methods and homology calculations.

The NCBI Basic Local Alignment Search Tool (BLAST) (Altschul et al. *J. Mol. Biol.* 215:403-410, 1990) is available from several sources, including the National Center for Biotechnology Information (NCBI, Bethesda, Md.) and on the Internet, for use in connection with the sequence analysis programs blastp, blastn, blastx, tblastn and tblastx. By way of example, for comparisons of amino acid sequences of greater than about 30 amino acids, the Blast 2 sequences function is employed using the default BLOSUM62 matrix set to default parameters, (gap existence cost of 11, and a per residue gap cost of 1). When aligning short peptides (fewer than around 30 amino acids), the alignment is performed using the Blast 2 sequences function, employing the PAM30 matrix set to default parameters (open gap 9, extension gap 1 penalties).

An alternative indication that two nucleic acid molecules are closely related is that the two molecules hybridize to each other under stringent conditions. Stringent conditions are sequence-dependent and are different under different environmental parameters. Generally, stringent conditions are selected to be about 5° C. to 20° C. lower than the thermal melting point ($T_m$) for the specific sequence at a defined ionic strength and pH. The $T_m$ is the temperature (under defined ionic strength and pH) at which 50% of the target sequence remains hybridized to a perfectly matched probe or complementary strand.

In nucleic acid hybridization reactions, the conditions used to achieve a particular level of stringency will vary depending on the nature of the nucleic acids being hybridized. For example, the length, degree of complementarity, nucleotide sequence composition (for example, GC v. AT content), and nucleic acid type (for example, RNA versus DNA) of the hybridizing regions of the nucleic acids can be considered in selecting hybridization conditions. An additional consideration is whether one of the nucleic acids is immobilized, for example, on a filter.

A specific, non-limiting example of progressively higher stringency conditions is as follows: 2×SSC/0.1% SDS at about room temperature (hybridization conditions); 0.2×SSC/0.1% SDS at about room temperature (low stringency conditions); 0.2×SSC/0.1% SDS at about 42° C. (moderate stringency conditions); and 0.1×SSC at about 68° C. (high stringency conditions). One of skill in the art can readily determine variations on these conditions (for example, *Molecular Cloning: A Laboratory Manual,* 2nd ed., vol. 1-3, ed. Sambrook et al., Cold Spring Harbor Laboratory Press, Cold Spring Harbor, N.Y., 2001). Washing can be carried out using only one of these conditions, for example, high stringency conditions, or each of the conditions can be used, for example, for 10-15 minutes each, in the order listed above, repeating any or all of the steps listed. However, as mentioned above, optimal conditions will vary, depending on the particular hybridization reaction involved, and can be determined empirically.

Nucleic acid sequences that do not show a high degree of sequence identity may nevertheless encode similar amino acid sequences, due to the degeneracy of the genetic code. It is understood that changes in nucleic acid sequence can be made using this degeneracy to produce multiple nucleic acid molecules that all encode substantially the same protein.

Subject: Living multi-cellular vertebrate organisms, a category that includes both human and non-human mammals.

Tumor: A neoplasm that may be either malignant or non-malignant. Tumors of the same tissue type are primary tumors originating in a particular organ (such as colon, breast, prostate, bladder or lung). Tumors of the same tissue type may be divided into tumor of different sub-types (a classic example being bronchogenic carcinomas (lung tumors) which can be an adenocarcinoma, small cell, squamous cell, or large cell tumor). Breast cancers can be divided histologically into scirrhous, infiltrative, papillary, ductal, medullary and lobular. In one embodiment, cells in a tumor express CEA.

Variable region (also variable domain or V domain): The regions of both the light chain and the heavy chain of an Ig that contain antigen-binding sites. The regions are composed of polypeptide chains containing four relatively invariant "framework regions" (FRs) and three highly variant "hypervariable regions" (HVs). Because the HVs constitute the binding site for antigen(s) and determine specificity by forming a surface complementarity to the antigen, they are more commonly termed the "complementarity-determining regions," or CDRs, and are denoted CDR1, CDR2, and CDR3. Because both of the CDRs from the heavy and light chain domains contribute to the antigen-binding site, it is the three-dimensional configuration of the heavy and the light chains that determines the final antigen specificity.

Within the heavy and light chain, the framework regions surround the CDRs. Proceeding from the N-terminus of a heavy or light chain, the order of regions is: FR1-CDR1-FR2-CDR2-FR3-CDR3-FR4. As used herein, the term "variable region" is intended to encompass a complete set of four framework regions and three complementarity-determining regions. Thus, a sequence encoding a "variable region" would provide the sequence of a complete set of four framework regions and three complementarity-determining regions.

Unless otherwise explained, all technical and scientific terms used herein have the same meaning as commonly understood by one of ordinary skill in the art to which this invention belongs. The singular terms "a," "an," and "the" include plural referents unless context clearly indicates otherwise. Similarly, the word "or" is intended to include "and" unless the context clearly indicates otherwise. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including explanations of terms, will control. In addition, the materials, methods, and examples are illustrative only and not intended to be limiting.

Minimally Immunogenic Humanized COL-1 Antibodies

Murine monoclonal antibody COL-1, which specifically recognizes carcinoembryonic antigen (CEA), is potentially an important clinical reagent for the diagnosis and treatment of CEA-positive carcinomas. However, patients receiving murine COL-1 generate human anti-murine antibody (HAMA) responses, preventing repeated administration of the antibody for effective treatment. To minimize the HAMA response, the number of murine residues in the antibody must be minimized. However, this must be accomplished without compromising CEA binding affinity.

The humanized COL-1 antibodies disclosed herein bind CEA and are minimally immunogenic. In one embodiment, the humanized COL-1 antibody is formed by grafting at least one murine COL-1 CDR onto a human variable light ($V_L$) and/or human variable heavy ($V_H$) chain framework and includes some murine COL-1 framework residues. In another embodiment, the humanized COL-1 antibody is formed by grafting at least one murine COL-1 abbreviated CDR onto a human $V_L$ and/or $V_H$ chain framework and includes some murine COL-1 framework residues. In yet another embodiment, the humanized COL-1 antibody is formed by grafting at least one murine COL-1 SDR onto human $V_L$ and/or $V_H$ chain frameworks and includes some murine COL-1 framework residues.

Early generations of humanized COL-1 antibodies, for example HuCOL-1, HuCOL-1$_{AbrCDR}$, or HuCOL-1$_{SDR}$, included some framework residues that were specifically murine and previously thought to be essential for the integrity of the antigen binding site. For example, the specifically murine light chain framework residues in these humanized antibodies are included at residue 4 of FR1 (residues 1-23 of SEQ ID NO: 1), residues 4, 22, and 29 of FR3 (residues 61-92 of SEQ ID NO: 1), and residue 7 of FR4 (residues 101-110 of SEQ ID NO: 1). Murine heavy chain framework residues are included at residues 1, 12, 20, 27, 28, 29, and 30 of FR1 (residues 1-30 of SEQ ID NO: 5), residues 3 and 13 of FR2 (residues 36-49 of SEQ ID NO: 5), residues 1, 2, 6, 13, 15, 31 and 32 of FR3 (residues 67-98 of SEQ ID NO: 5), and residue 3 of FR4 (residues 114-124 of SEQ ID NO: 5). Thus, in one embodiment, the humanized COL-1 antibodies disclosed herein are derived from a previously generated humanized COL-1 antibody, for example HuCOL-1, HuCOL-1$_{AbrCDR}$, or HuCOL-1$_{SDR}$, by substituting one or more murine residues in the framework regions with residues from corresponding positions of a homologous human antibody sequence according to the numbering convention delineated by Kabat et al. (supra; also known as a Kabat position). In one example, at least one of the murine $V_L$ framework residues is substituted with a residue at the corresponding position in the VJI'CL human antibody light chain sequence (SEQ ID NO: 2). In another example, at least one of the murine $V_H$ framework residues is substituted with a residue at the corresponding position in the MO30 human antibody heavy chain sequence (SEQ ID NO: 6). In specific, non-limiting examples, at least one murine framework residue in the light chain is substituted with a residue at the corresponding position in the human VJI'CL sequence and/or at least one murine framework residue in the heavy chain is substituted with a residue at the corresponding position in the human MO30 sequence (see FIG. 2).

HuCOL-1$_{AbrCDR}$ includes five murine-specific framework residues in the variable light chain and 17 murine-specific framework residues in the variable heavy chain (FIGS. 1 and 2, SEQ ID NOs: 4 and 8). In one embodiment, one or more murine residues of the heavy chain of HuCOL-1$_{AbrCDR}$ (SEQ ID NO: 8) are substituted with the corresponding residue of the amino acid sequence as set forth in SEQ ID NO: 6. In one specific non-limiting example, the antibody is termed HuCOL-1$_{AbrCDR}$ framework variant 4 (FRV4) and includes a valine at residue 20 (Kabat position 20), an arginine at residue 38 (Kabat position 38), a methionine at residue 48 (Kabat position 48), an arginine at residue 67 (Kabat position 66), a valine at residue 79 (Kabat position 78), and a methionine at residue 81 (Kabat position 80) in SEQ ID NO: 12 (see Table I and FIG. 2). In another specific example, the antibody is termed HuCOL-1$_{AbrCDR}$ framework variant 7 (FRV7) and further includes a tyrosine at residue 27 (Kabat position 27) and a valine at residue 68 (Kabat position 67) in SEQ ID NO: 13 (Table I and FIG. 2). In a further specific example, the antibody is termed HuCOL-1$_{AbrCDR}$ framework variant 10 (FRV10) and additionally includes a glutamine at residue 1 (Kabat position 1) and a lysine at residue 12 (Kabat position 12) in SEQ ID NO: 14 (Table I and FIG. 2).

TABLE I

Framework positions substituted in the HuCOL-1$_{AbrCDR}$-derived antibodies

| Variant | Framework Position Substituted[a] Light Chain | Heavy Chain |
|---|---|---|
| HuCOL-1$_{AbrCDR}$ | None | None |
| FRV2 | L4M[b], V78L, L104V | None |
| FRV3 | L4M, A60D, V78L, T85V, L104V | None |
| FRV4 | None | M20V, K38R, I48M, K66R, A78V, L80M |
| FRV5 | L4M, V78L, L104V | M20V, K38R, I48M, K66R, A78V, L80M |
| FRV6 | L4M, A60D, V78L, T85V, L104V | M20V, K38R, I48M, K66R, A78V, L80M |
| FR7 | None | M20V, F27Y, K38R, I48M, K66R, A67V, A78V, L80M |
| FRV8 | L4M, V78L, L104V | M20V, F27Y, K38R, I48M, K66R, A67V, A78V, L80M |
| FRV9 | L4M, A60D, V78L, T85V, L104V | M20V, F27Y, K38R, I48M, K66R, A67V, A78V, L80M |
| FRV10 | None | E1Q, V12K, M20V, F27Y, K38R, I48M, K66R, A67V, A78V, L80M |
| FRV11 | L4M, V78L, L104V | E1Q, V12K, M20V, F27Y, K38R, I48M, K66R, A67V, A78V, L80M |
| FRV12 | L4M, A60D, V78L, T85V, L104V | E1Q, V12K, M20V, F27Y, K38R, I48M, K66R, A67V, A78V, L80M |

[a]Numbering convention of Kabat et al. (Sequence of Proteins of Immunological Interests, 5$^{th}$ ed., p. NIH Publication No. 91-3242, U.S. Department of Health and Human Services, National Institutes of Health, Bethesda, MD, 1991)
[b]The first letter indicates the original amino acid, the number indicates the Kabat position in the light or heavy chain, and the second letter indicates the substitution. The amino acids are represented by single letter code.

In one embodiment, the humanized COL-1 antibody has a CH2 domain deletion. (Slavin-Chiorini et al., *Int. J. Cancer*, 53:97-103, 1993; Slavin-Chiorini et al., *Cancer Research*, 55:5957s-5967s, 1995; Slavin-Chiorini et al., *Cancer Biother. Radiopharm.*, 12:305-316, 1997, incorporated herein by reference). The generation and characterization of CH2 domain deleted antibodies is described in Mueller et al., *Proc. Natl. Acad. Sci. USA.*, 87:5702-5705, 1990. In one specific example, the CH2 deletion is located between residue 242 of the antibody hinge and residue 361 of CH3. In one specific embodiment, a humanized COL-1 antibody with a CH2 domain deletion is cleared more quickly from the plasma compared to the corresponding humanized COL-1 antibody which includes the CH2 domain. In another specific embodiment, a humanized COL-1 antibody with a CH2 domain deletion has reduced immunogenicity compared to the humanized COL-1 antibody which includes the CH2 domain.

The humanized COL-1 antibodies disclosed herein, such as FRV4, FRV7, and FRV10, contain a reduced murine content, and consequently, reduced immunogenicity, when compared to mCOL-1, HuCOL-1, and HuCOL-1$_{AbrCDR}$. Nonetheless, the humanized COL-1 antibodies of the invention have a CEA binding affinity that is similar to or is increased as compared to mCOL-1, HuCOL-1, and/or HuCOL-1$_{AbrCDR}$. Thus, the humanized COL-1 antibodies disclosed herein retain CEA binding affinity, as compared to mCOL-1, HuCOL-1, and/or HuCOL-1$_{AbrCDR}$. In one embodiment, the humanized COL-1 antibody retains CEA binding affinity and has an affinity for CEA that is at least about $2.0 \times 10^{-8}$ M. In other embodiments, the humanized COL-1 antibody retains CEA binding affinity and has an affinity for CEA that is at least about $2.5 \times 10^{-8}$, about $3.0 \times 10^{-8}$, about $3.5 \times 10^{-8}$, about $4.0 \times 10^{-8}$, $4.5 \times 10^{-8}$, or about $5.0 \times 10^{-8}$ M or greater. In one embodiment, the humanized COL-1 antibody retains CEA binding affinity if it has a lower antigen/antibody dissociation rate compared to that of mCOL-1, HuCOL-1, and/or HuCOL-1$_{AbrCDR}$. In another embodiment, the humanized COL-1 antibody retains CEA binding affinity if less antibody is required for a 50% inhibition of the binding of $^{125}$I-labeled mCOL-1 to CEA compared to mCOL-1, HuCOL-1, and/or HuCOL-1$_{AbrCDR}$. In yet another embodiment, the humanized COL-1 antibody retains CEA binding affinity when the number of cells labeled with humanized COL-1 antibody is greater than the number of cells labeled by mCOL-1, HuCOL-1, and/or HuCOL-1$_{AbrCDR}$, as measured by flow cytometry.

Immunogenicity of humanized COL-1 antibodies can be measured in a competitive binding assay as the ability of a humanized COL-1 antibody, such as FRV4, FRV7, or FRV10, to prevent mCOL-1, HuCOL-1, or HuCOL-1$_{AbrCDR}$ from binding to anti-idiotypic antibodies in a human subject's serum. In one embodiment, the humanized COL-1 antibody is minimally immunogenic in a subject. In one embodiment, at least about two-fold higher molar concentration of the humanized COL-1 antibody, than that of mCOL-1, HuCOL-1, and/or HuCOL-1$_{AbrCDR}$, is required to elicit 50% inhibition of mCOL-1, HuCOL-1, and/or HuCOL-1$_{AbrCDR}$ binding to its cognate anti-idiotypic antibodies in a subject's sera. In other embodiments, at least about three-fold, at least about four-fold, at least about five-fold, at least about six-fold, at least about ten-fold, at least about twenty-fold, at least about twenty-five-fold, at least about thirty-fold, at least about fifty-fold, or at least about one hundred-fold higher molar concentration of the humanized COL-1 antibody, than that of mCOL-1, HuCOL-1, and/or HuCOL-$1_{AbrCDR}$, is required to elicit 50% inhibition of mCOL-1, HuCOL-1, and/or HuCOL-$1_{AbrCDR}$ binding to its cognate anti-idiotypic antibodies in a subject's sera.

Effector Molecule-Linked Humanized COL-1 Antibodies

Effector molecules, for example, therapeutic, diagnostic, or detection moieties, can be linked to a humanized COL-1 antibody that specifically binds CEA, using any number of means known to those of skill in the art. Thus, a humanized COL-1 antibody with an amino acid substitution can have any one of a number of different types of effector molecules linked to it. In addition, the antibody can be linked to an effector molecule by a covalent or non-covalent means. In one embodiment, the antibody is linked to a detectable label. In some embodiments, the antibody is linked to a radioactive isotope, an enzyme substrate, a chemotherapeutic drug, a co-factor, a ligand, a chemiluminescent agent, a fluorescent agent, a hapten, or an enzyme. In other embodiments, the antibody is linked to a cytokine. Specific, non-limiting examples of cytokines are IL-2, IL-4, IL-10, TNF-alpha and IFN-gamma. In yet other embodiments, the antibody is linked to a cytotoxin, such as a bacterially-expressed toxin, a virally-expressed toxin, or a venom protein, to yield immunotoxins. Specific, non-limiting examples of cytotoxins include ricin, abrin, *Pseudomonas* exotoxin (PE), diphtheria toxin and subunits thereof, as well as botulinum toxins A through F. These toxins are readily available from commercial sources (for example, Sigma Chemical Company, St. Louis, Mo.).

Diphtheria toxin is isolated from *Corynebacterium diphtheriae*. Ricin is the lectin RCA60 from *Ricinus communis* (Castor bean). The term also references toxic variants thereof. For example, see, U.S. Pat. No. 5,079,163 and U.S. Pat. No. 4,689,401. *Ricinus communis* agglutinin (RCA) occurs in two forms designated $RCA_{60}$ and $RCA_{120}$ according to their molecular weights of approximately 65 and 120 kDa respectively (Nicholson & Blaustein, *J. Biochim. Biophys. Acta* 266:543, 1972). The A chain is responsible for inactivating protein synthesis and killing cells. The B chain binds ricin to cell-surface galactose residues and facilitates transport of the A chain into the cytosol (Olsnes et al., *Nature* 249:627-631, 1974 and U.S. Pat. No. 3,060,165).

Abrin includes toxic lectins from *Abrus precatorius*. The toxic principles, abrin a, b, c, and d, have a molecular weight of from about 63 and 67 kDa and are composed of two disulfide-linked polypeptide chains A and B. The A chain inhibits protein synthesis; the B-chain (abrin-b) binds to D-galactose residues (see, Funatsu, et al., *Agr. Biol. Chem.* 52:1095, 1988; and Olsnes, *Methods Enzymol.* 50:330-335, 1978).

In several embodiments, the toxin is *Pseudomonas* exotoxin (PE). The term "*Pseudomonas* exotoxin" as used herein refers to a full-length native (naturally occurring) PE or a PE that has been modified. Such modifications may include, but are not limited to, elimination of domain Ia, various amino acid deletions in domains Ib, II and III, single amino acid substitutions and the addition of one or more sequences at the carboxyl terminus such as KDEL (SEQ ID NO: 17) and REDL (SEQ ID NO: 18) (see Siegall et al., *J. Biol. Chem.* 264: 14256-14261, 1989, incorporated by reference herein). In a preferred embodiment, the cytotoxic fragment of PE retains at least 50%, preferably 75%, more preferably at least 90%, and most preferably 95% of the cytotoxicity of native PE. In a most preferred embodiment, the cytotoxic fragment is more toxic than native PE.

Native *Pseudomonas* exotoxin A is an extremely active monomeric protein (molecular weight 66 kD), secreted by *Pseudomonas aeruginosa*, which inhibits protein synthesis in eukaryotic cells. The native PE sequence is provided as SEQ ID NO: 1 of U.S. Pat. No. 5,602,095, incorporated herein by reference. The method of action is inactivation of the ADP-ribosylation of elongation factor 2 (EF-2). The exotoxin contains three structural domains that act in concert to cause cytotoxicity. Domain Ia (amino acids 1-252) mediates cell binding. Domain II (amino acids 253-364) is responsible for translocation into the cytosol and domain III (amino acids 400-613) mediates ADP ribosylation of elongation factor 2. The function of domain Ib (amino acids 365-399) remains undefined, although a large part of it, amino acids 365-380, can be deleted without loss of cytotoxicity (see Siegall et al., supra).

PE employed includes the native sequence, cytotoxic fragments of the native sequence, and conservatively modified variants of native PE and its cytotoxic fragments. Cytotoxic fragments of PE include those which are cytotoxic with or without subsequent proteolytic or other processing in the target cell (for example, as a protein or pre-protein). Cytotoxic fragments of PE include PE40, PE38, PE37, and PE35. PE40 is a truncated derivative of PE as previously described in the art (see Pai et al., *Proc. Nat'l Acad. Sci. USA* 88:3358-62, 1991 and Kondo et al., *J. Biol. Chem.* 263:9470-9475, 1988). PE35 is a 35 kD carboxyl-terminal fragment of PE composed of a methionine at position 280 followed by amino acids 281-364 and 381-613 of native PE. PE37, another truncated derivative of PE, is described in U.S. Pat. No. 5,821, 238. PE38 is a truncated PE pro-protein composed of amino acids 253-364 and 381-613 which is activated to its cytotoxic form upon processing within a cell (see U.S. Pat. No. 5,608, 039, incorporated herein by reference). In a particularly preferred embodiment, PE38 is the toxic moiety of the immunotoxin, however, other cytotoxic fragments, such as PE35, PE37, and PE40, are contemplated and are disclosed in U.S. Pat. No. 5,602,095; U.S. Pat. No. 5,821,238; and U.S. Pat. No. 4,892,827, each of which is incorporated herein by reference.

Polynucleotides Encoding Humanized COL-1 Antibodies

Polynucleotides encoding the $V_L$ and/or the $V_H$ of minimally immunogenic humanized antibodies that bind CEA, such as FRV4, FRV7, and FRV10, are also provided. These polynucleotides include DNA, cDNA and RNA sequences which encode the humanized antibody. It is understood that all polynucleotides encoding these antibodies are also included herein, as long as they encode a polypeptide with the recognized activity, such as binding to CEA. The polynucleotides of this disclosure include sequences that are degenerate as a result of the genetic code. There are 20 natural amino acids, most of which are specified by more than one codon. Therefore, all degenerate nucleotide sequences are included as long as the amino acid sequence of the antibody encoded by the nucleotide sequence is functionally unchanged.

Primers, such as polymerase chain reaction (PCR) primers can readily be prepared that hybridize to a specific $V_H$ or $V_L$, or a component thereof. In one embodiment, the primers include at least ten, at least 15, 16, 17, 18, 19, or 20 consecutive nucleotides of a nucleic acid encoding the $V_H$ or $V_L$ of interest. Also included are fragments of the above-described nucleic acid sequences that are at least 15 bases in length, which is sufficient to permit the fragment to selectively hybridize to DNA that encodes the antibody of interest under physiological conditions. The term "selectively hybridize" refers to hybridization under moderately or highly stringent conditions, which excludes non-related nucleotide sequences.

A nucleic acid encoding a $V_L$ and/or $V_H$ of a humanized COL-1 antibody that specifically binds CEA, such as FRV4, FRV7, and FRV10, can be cloned or amplified by in vitro methods, such as the polymerase chain reaction (PCR), the ligase chain reaction (LCR), the transcription-based amplification system (TAS), the self-sustained sequence replication system (3SR) and the Qβ replicase amplification system (Qβ). For example, a polynucleotide encoding the protein can be isolated by PCR of cDNA using primers based on the DNA sequence of the molecule. A wide variety of cloning and in vitro amplification methodologies are well known to persons skilled in the art. PCR methods are described in, for example, U.S. Pat. No. 4,683,195; Mullis et al., *Cold Spring Harbor Symp. Quant. Biol.* 51:263, 1987; and Erlich, ed., *PCR Technology*, (Stockton Press, NY, 1989). Polynucleotides also can be isolated by screening genomic or cDNA libraries with probes selected from the sequences of the desired polynucleotide under stringent hybridization conditions.

The polynucleotides include a recombinant DNA which is incorporated into a vector; into an autonomously replicating plasmid or virus; or into the genomic DNA of a prokaryote or eukaryote, or which exists as a separate molecule (for example, a cDNA) independent of other sequences. The nucleotides of the invention can be ribonucleotides, deoxyribonucleotides, or modified forms of either nucleotide. The term includes single and double forms of DNA.

DNA sequences encoding a $V_L$ and/or $V_H$ of a humanized COL-1 antibody that specifically binds CEA, such as FRV4, FRV7, and FRV10, can be expressed in vitro by DNA transfer into a suitable host cell. The cell may be prokaryotic or eukaryotic. The term also includes any progeny of the subject host cell. It is understood that all progeny may not be identical to the parental cell since there may be mutations that occur during replication. Methods of stable transfer, meaning that the foreign DNA is continuously maintained in the host, are known in the art.

A polynucleotide sequence encoding a $V_L$ and/or $V_H$ of a humanized COL-1 antibody that specifically binds CEA, such as FRV4, FRV7, and FRV10, can be operatively linked to expression control sequences. An expression control sequence operatively linked to a coding sequence is ligated such that expression of the coding sequence is achieved under conditions compatible with the expression control sequences. The expression control sequences include, but are not limited to, appropriate promoters, enhancers, transcription terminators, a start codon (for instance, ATG) in front of a protein-encoding gene, splicing signal for introns, maintenance of the correct reading frame of that gene to permit proper translation of mRNA, and stop codons. Thus, an scFv can be produced.

The polynucleotide sequences encoding a $V_L$ and/or $V_H$ of a humanized COL-1 antibody that specifically binds CEA, such as FRV4, FRV7, and FRV10, can be inserted into an expression vector including, but not limited to, a plasmid, virus or other vehicle that can be manipulated to allow insertion or incorporation of sequences and can be expressed in either prokaryotes or eukaryotes. Hosts can include microbial, yeast, insect and mammalian organisms. Methods of expressing DNA sequences having eukaryotic or viral sequences in prokaryotes are well known in the art. Biologically functional viral and plasmid DNA vectors capable of expression and replication in a host are known in the art.

Transformation of a host cell with recombinant DNA may be carried out by conventional techniques as are well known to those skilled in the art. Where the host is prokaryotic, such as *E. coli*, competent cells which are capable of DNA uptake can be prepared from cells harvested after exponential growth phase and subsequently treated by the $CaCl_2$ method using procedures well known in the art. Alternatively, $MgCl_2$ or RbCl can be used. Transformation can also be performed after forming a protoplast of the host cell if desired, or by electroporation.

When the host is a eukaryote, such methods of transfection of DNA as calcium phosphate coprecipitation, conventional mechanical procedures such as microinjection, electroporation, insertion of a plasmid encased in liposomes, or virus vectors may be used. Eukaryotic cells can also be cotransformed with the polynucleotide sequence of interest, and a second foreign DNA molecule encoding a selectable phenotype, such as the herpes simplex thymidine kinase gene.

Another method is to use a eukaryotic viral vector, such as simian virus 40 (SV40) or bovine papilloma virus, to transiently infect or transform eukaryotic cells and express the protein (see for example, *Eukaryotic Viral Vectors*, Cold Spring Harbor Laboratory, Gluzman ed., 1982).

Isolation and purification of recombinantly-expressed polypeptides may be carried out by conventional means including preparative chromatography and immunological separations.

Immunological Compositions, Pharmaceutical Compositions, and Therapeutic Methods Agents that affect tumors (for example, agents that inhibit or suppress the growth of CEA-expressing tumors, such as FRV4, FRV7, or FRV10) or an immunogenic agent, such as a vaccine, can be administered directly to the subject for inhibiting further growth of an existing tumor or suppressing tumor growth. The agents may be provided alone or in combination to the subject as immunological or pharmaceutical compositions. In addition, the agents may be provided to the subject simultaneously or sequentially, in any order.

Immunological Compositions

Immunological compositions, including vaccines, are useful for enhancing an immune response for inhibiting further growth of an existing tumor or suppressing tumor growth. One or more of the immunogenic agents are formulated and packaged, alone or in combination with adjuvants or other antigens, using methods and materials known to those skilled in the vaccine art. An immunological response of a subject to such an immunological composition may be used therapeutically, and in certain embodiments provides antibody immunity and/or cellular immunity such as that produced by T lymphocytes.

A variety of adjuvants known to one of ordinary skill in the art may be administered in conjunction with the immunogenic agents in the provided immunological composition. Such adjuvants include but are not limited to the following: polymers, co-polymers such as polyoxyethylene-polyoxypropylene copolymers, including block co-polymers; polymer P1005; Freund's complete adjuvant (for animals); Freund's incomplete adjuvant; sorbitan monooleate; squalene; CRL-8300 adjuvant; alum; QS 21, muramyl dipeptide; CpG oligonucleotide motifs and combinations of CpG oligonucleotide motifs; trehalose; bacterial extracts, including mycobacterial extracts; detoxified endotoxins; membrane lipids; or combinations thereof.

The compositions provided herein, including those for use as immunostimulatory agents, may be administered through different routes, such as oral, including buccal and sublingual, rectal, parenteral, aerosol, nasal, intramuscular, subcutaneous, intradermal, and topical. They may be administered in different forms, including but not limited to solutions, emulsions and suspensions, microspheres, particles, microparticles, nanoparticles, and liposomes.

The volume of administration will vary depending on the route of administration. By way of example, intramuscular injections may range from about 0.1 ml to 1.0 ml. Those of ordinary skill in the art will know appropriate volumes for different routes of administration.

The amount of immunogenic agent in each immunological composition dose is selected as an amount that induces an immunoprotective response without significant, adverse side effects. Such amount will vary depending upon which specific immunogen is employed and how it is presented. Doses for human administration of a pharmaceutical composition or a vaccine may be from about 0.01 mg/kg to 10 mg/kg, for instance approximately 1 mg/kg. Based on this range, equivalent dosages for heavier (or lighter) body weights can be determined. The dose may be adjusted to suit the individual to whom the composition is administered, and may vary with age, weight, and metabolism of the individual, as well as the health of the subject. Such determinations are left to the attending physician or another familiar with the subject and/or the specific situation. The immunological composition may additionally contain stabilizers or physiologically acceptable preservatives, such as thimerosal (ethyl(2-mercaptobenzoate-S)mercury sodium salt) (Sigma Chemical Company, St. Louis, Mo.). Following an initial vaccination, subjects may receive one or several booster immunizations, adequately spaced. Booster injections may range from 1 µg to 1 mg, with other embodiments having a range of approximately 10 µg to 750 µg, and still others a range of about 50 µg to 500 µg. Periodic boosters at intervals of 1-5 years, for instance three years, may be desirable to maintain the desired levels of protective immunity.

In a particular embodiment, an immunological composition is packaged in a single dosage for immunization by parenteral (for instance, intramuscular, intradermal or subcutaneous) administration or nasopharyngeal (for instance, intranasal) administration. In certain embodiments, the immunological composition is injected intramuscularly into the deltoid muscle. The immunological composition may be combined with a pharmaceutically acceptable carrier to facilitate administration. The carrier is, for instance, water, or a buffered saline, with or without a preservative. The immunological composition may be lyophilized for resuspension at the time of administration or in solution.

The carrier to which the immunogenic agents may be conjugated may also be a polymeric delayed release system. Synthetic polymers are particularly useful in the formulation of a vaccine to effect the controlled release of antigens.

Microencapsulation of the immunogenic agents will also give a controlled release. A number of factors contribute to the selection of a particular polymer for microencapsulation. The reproducibility of polymer synthesis and the microencapsulation process, the cost of the microencapsulation materials and process, the toxicological profile, the requirements for variable release kinetics and the physicochemical compatibility of the polymer and the antigens are all factors that must be considered. Examples of useful polymers are polycarbonates, polyesters, polyurethanes, polyorthoesters polyamides, poly(d,l-lactide-co-glycolide) (PLGA) and other biodegradable polymers.

The compositions provided herein, including those formulated to serve as immunological compositions, may be stored at temperatures of from about −100° C. to 4° C. They may also be stored in a lyophilized state at different temperatures, including higher temperatures such as room temperature. The preparation may be sterilized through conventional means known to one of ordinary skill in the art. Such means include, but are not limited to filtration, radiation and heat. The preparations also may be combined with bacteriostatic agents, such as thimerosal, to inhibit bacterial growth.

Pharmaceutical Compositions

Pharmaceutical compositions are disclosed herein that include a humanized COL-1 antibody, such as FRV4, FRV7, or FRV10, that can be formulated with an appropriate solid or liquid carrier, depending upon the particular mode of administration chosen. In addition, a humanized COL-1 antibody linked to an effector molecule (for instance, a toxin, a chemotherapeutic drug, or a detectable label) can be prepared in pharmaceutical compositions.

The pharmaceutically acceptable carriers and excipients useful in this disclosure are conventional. For instance, parenteral formulations usually comprise injectable fluids that are pharmaceutically and physiologically acceptable fluid vehicles such as water, physiological saline, other balanced salt solutions, aqueous dextrose, glycerol or the like. Excipients that can be included are, for instance, other proteins, such as human serum albumin or plasma preparations. If desired, the pharmaceutical composition to be administered can also contain minor amounts of non-toxic auxiliary substances, such as wetting or emulsifying agents, preservatives, and pH buffering agents and the like, for example sodium acetate or sorbitan monolaurate.

The dosage form of the pharmaceutical composition will be determined by the mode of administration chosen. For instance, in addition to injectable fluids, topical, inhalation, oral and suppository formulations can be employed. Topical preparations can include eye drops, ointments, sprays and the like. Inhalation preparations can be liquid (for example, solutions or suspensions) and include mists, sprays and the like. Oral formulations can be liquid (for example, syrups, solutions or suspensions), or solid (for example, powders, pills, tablets, or capsules). Suppository preparations can also be solid, gel, or in a suspension form. For solid compositions, conventional non-toxic solid carriers can include pharmaceutical grades of mannitol, lactose, starch, or magnesium stearate. Actual methods of preparing such dosage forms are known, or will be apparent, to those skilled in the art.

The pharmaceutical compositions that include a humanized COL-1 antibody, such as FRV4, FRV7, or FRV10, can be formulated in unit dosage form, suitable for individual administration of precise dosages. In addition, the pharmaceutical compositions may be administered as an immunoprophylactic in a single dose schedule or as an immunotherapy in a multiple dose schedule. A multiple dose schedule is one in which a primary course of treatment may be with more than one separate dose, for instance one to ten doses, followed by other doses given at subsequent time intervals as needed to maintain or reinforce the action of the compositions. Treatment can involve daily or multi-daily doses of compound(s) over a period of a few days to months, or even years. Thus, the dosage regime will also, at least in part, be determined based on the particular needs of the subject to be treated and will be dependent upon the judgment of the administering practitioner. In one specific, non-limiting example, a unit dosage can be about 0.1 to about 10 mg per subject per day. Dosages from about 0.1 up to about 100 mg per subject per day may be used, particularly if the agent is administered to a secluded site and not into the circulatory or lymph system, such as into a body cavity, into a lumen of an organ, or directly into a tumor. The amount of active compound(s) administered will be dependent on the subject being treated, the severity of the affliction, and the manner of administration, and is best left to the judgment of the prescribing clinician. Within these bounds, the formulation to be administered will contain a quantity of the active component(s) in amounts effective to achieve the desired effect in the subject being treated.

The compounds of this disclosure can be administered to humans on whose tissues they are effective in various manners such as topically, orally, intravenously, intramuscularly, intraperitoneally, intranasally, intradermally, intrathecally, subcutaneously, via inhalation or via suppository. The particular mode of administration and the dosage regimen will be selected by the attending clinician, taking into account the particulars of the case (for example, the subject, the disease, the disease state involved, and whether the treatment is prophylactic).

Controlled release parenteral formulations of a humanized COL-1 monoclonal antibody can be made as implants, oily injections, or as particulate systems. For a broad overview of protein delivery systems (see Banga, A. J., *Therapeutic Peptides and Proteins: Formulation, Processing, and Delivery Systems*, Technomic Publishing Company, Inc., Lancaster, Pa., 1995). Particulate systems include microspheres, microparticles, microcapsules, nanocapsules, nanospheres, and nanoparticles. Microcapsules contain the therapeutic protein as a central core. In microspheres the therapeutic is dispersed throughout the particle. Particles, microspheres, and microcapsules smaller than about 1 µm are generally referred to as nanoparticles, nanospheres, and nanocapsules, respectively. Capillaries have a diameter of approximately 5 µm so that only nanoparticles are administered intravenously. Microparticles are typically around 100 µm in diameter and are administered subcutaneously or intramuscularly (see Kreuter, J., *Colloidal Drug Delivery Systems*, J. Kreuter, ed., Marcel Dekker, Inc., New York, N.Y., pp. 219-342, 1994; Tice & Tabibi, *Treatise on Controlled Drug Delivery*, A. Kydonieus, ed., Marcel Dekker, Inc. New York, N.Y., pp. 315-339, 1992).

Polymers can be used for ion-controlled release. Various degradable and nondegradable polymeric matrices for use in controlled drug delivery are known in the art (Langer, R., *Accounts Chem. Res.* 26:537, 1993). For example, the block copolymer, polaxamer 407 exists as a viscous yet mobile liquid at low temperatures but forms a semisolid gel at body temperature. It has shown to be an effective vehicle for formulation and sustained delivery of recombinant IL-2 and urease (Johnston et al., *Pharm. Res.* 9:425, 1992; and Pec et al., *J. Parent. Sci. Tech.* 44:58, 1990). Alternatively, hydroxyapatite has been used as a microcarrier for controlled release of proteins (Ijntema et al., *Int. J. Pharm.* 112:215, 1994). In yet another aspect, liposomes are used for controlled release as well as drug targeting of the lipid-capsulated drug (Betageri et al., *Liposome Drug Delivery Systems*, Technomic Publishing Co., Inc., Lancaster, Pa., 1993). Numerous additional systems for controlled delivery of therapeutic proteins are known (for example, U.S. Pat. Nos. 5,055,303; 5,188,837; 4,235,871; 4,501,728; 4,837,028; 4,957,735 and 5,019,369; 5,055,303; 5,514,670; 5,413,797; 5,268,164; 5,004,697; 4,902,505; 5,506,206, 5,271,961; 5,254,342 and 5,534,496).

Site-specific administration of the disclosed compounds can be used, for instance by applying the humanized COL-1 antibody to a pre-cancerous region, a region of tissue from which a tumor has been removed, or a region suspected of being prone to tumor development. In some embodiments, sustained intra-tumoral (or near-tumoral) release of the pharmaceutical preparation that includes a therapeutically effective amount of humanized COL-1 antibody may be beneficial.

The present disclosure also includes therapeutic uses of humanized COL-1 monoclonal antibodies, such as FRV4, FRV7, or FRV10, that are non-covalently or covalently linked to effector molecules (see above). In one specific embodiment, the humanized COL-1 monoclonal antibody is covalently linked to an effector molecule that is toxic to a tumor or cell expressing CEA. In one specific, non-limiting example, the effector molecule is a cytotoxin. In other specific, non-limiting examples, the effector molecule is a detectable label, a radioactive isotope, a chemotherapeutic drug, a bacterially-expressed toxin, a virally-expressed toxin, a venom protein, or a cytokine. Humanized COL-1 antibodies linked to effector molecules can be prepared in pharmaceutical compositions.

Combined Compositions

A pharmaceutical composition, described above, can be combined with an immunological composition, described above, in order to administer a combination of agents in a single dose. It is contemplated that the present disclosure also includes combinations of a humanized COL-1 monoclonal antibody, such as FRV4, FRV7, or FRV10, with one or more other agents useful in the treatment of tumors. For example, the compounds of this disclosure can be administered in combination with effective doses of immunostimulants, anti-cancer agents, anti-inflammatory agents, anti-infectives, and/or vaccines. The term "administration in combination" or "co-administration" refers to both concurrent and sequential administration of the active agents. A subject that has a tumor, or is predisposed to the development of a tumor, will be a candidate for treatment using the therapeutic methods disclosed herein.

An immunological composition including an immunogenic agent can be combined with a pharmaceutical composition including a humanized COL-1 antibody, such as FRV4, FRV7, or FRV10. As discussed above, the dose of the composition, the route of administration, and the frequency and the rate of administration will vary. Examples and guidelines for dosing are described above; yet more will be known to those of ordinary skill in the art.

Therapeutic Methods

Methods are disclosed herein for treating a subject with a tumor that expresses CEA by administering a therapeutically effective amount of the disclosed humanized COL-1 antibodies to the subject. Agents that affect tumors (for example, agents that inhibit or suppress the growth of CEA-expressing tumors, such as FRV4, FRV7, or FRV10) or an immunogenic agent, such as a vaccine, can be administered directly to the subject for inhibiting further growth of an existing tumor, enhancing tumor regression, inhibiting tumor recurrence, or inhibiting tumor metastasis.

In one embodiment, a therapeutically effective amount of a humanized COL-1 antibody, such as FRV4, FRV7, or FRV10, is the amount of humanized COL-1 antibody necessary to inhibit further growth of a tumor, such as a CEA-expressing tumor, or prevent or suppress the growth of a CEA-expressing tumor, without eliciting a HAMA response in the patient receiving the treatment. In other embodiments, a therapeutically effective amount of humanized COL-1 antibody is the amount of humanized COL-1 antibody necessary to eliminate or reduce the size of a CEA-expressing tumor, without eliciting a HAMA response. Specific, non-limiting examples of CEA-expressing tumors are adenocarcinoma, colorectal, gastric, pancreatic, breast, lung, and ovarian tumors. In yet another embodiment, a therapeutically effective amount of a humanized COL-1 antibody is an amount of humanized COL-1 antibody that is effective at reducing a sign or a symptom of the tumor and induces a minimal HAMA response. In a further embodiment, a therapeutically effective amount of a humanized COL-1 antibody is an amount of humanized COL-1 antibody that an anti-tumor (for example, tumors expressing CEA) activity.

A therapeutically effective amount of a humanized COL-1 monoclonal antibody, such as FRV4, FRV7, or FRV10, is an amount that can be used that will achieve target tissue or cell concentrations (for example, in tumors or tumor cells) that has been shown to achieve a desired effect in vitro. A therapeutically effective amount of a humanized COL-1 monoclonal antibody can be administered in a single dose, or in several doses, for example daily, during a course of treatment. In one embodiment, treatment continues until a therapeutic result is achieved. However, the effective amount of humanized COL-1 antibody will be dependent on the subject being treated, the severity and type of the affliction, and the manner of administration of the therapeutic(s).

Humanized COL-1 monoclonal antibodies covalently linked to an effector molecule have a variety of uses. For example, a humanized COL-1 antibody, such as FRV4, FRV7, or FRV10, can be linked to a radioactive isotope and used in immunotherapy to treat a tumor, for example a tumor expressing CEA. A humanized COL-1 antibody covalently linked to a radioactive isotope is of use to localize a tumor in radioimmunoguided surgery, such that the tumor can be surgically removed. In one embodiment, about 10 mCi of a radiolabeled humanized COL-1 monoclonal antibody is administered to a subject. In other embodiments, about 15 mCi, about 20 mCi, about 50 mCi, about 75 mCi or about 100 mCi of a radiolabeled humanized COL-1 monoclonal antibody is administered to a subject. In other embodiments, about 100 µCi to about 100 mCi of a radiolabled humanized COL-1 monoclonal antibody is administered to a subject.

Methods are disclosed herein of enhancing an anti-tumor immunity in a subject by administering a combination of agents, wherein the combination of agents produces an enhanced anti-tumor response, for example inhibiting further growth of an existing tumor or suppressing tumor growth. The disclosed method of administering two or more agents to a subject is more effective than the administration of each agent individually. The agents may be provided alone or in combination to the subject as immunological or pharmaceutical compositions. In addition, the agents may be provided to the subject simultaneously or sequentially, in any order.

In order to enhance an immune response in a subject, one or more of immunogenic agents is combined with a pharmaceutically acceptable carrier or vehicle for administration as an immunostimulatory composition or a vaccine (to human or animal subjects). In one embodiment, the combination includes an immunogenic agent that exhibits an immunogenic response and further inhibits tumor growth. In some embodiments, more than one immunogenic agent may be combined with a pharmaceutically acceptable carrier or vehicle to form a single preparation. In the combination therapy methods, the immunostimulatory composition may be provided to the subject simultaneously with or sequentially with (either before or after) the administration of a humanized COL-1 antibody, for example FRV4, FRV7, or FRV10.

In one specific, non-limiting embodiment, the administration of an immunogenic agent, for example vaccinia and fowlpox recombinants expressing CEA and three costimulatory molecules (B7-1, ICAM-1, LFA-3), enhances the effect of a humanized COL-1 antibody (such as FRV4, FRV7, or FRV10) on inhibiting or suppressing tumor growth.

Diagnostic Methods and Kits

A method is provided herein for the in vivo or in vitro detection of CEA-expressing tumors or cells. An in vivo detection method can localize any tumor or cell that expresses CEA in a subject. In one embodiment, a humanized COL-1 antibody, such as FRV4, FRV7, or FRV10, is administered to the subject for a sufficient amount of time for the antibody to localize to the tumor or cell in the subject and to form an immune complex with CEA. The immune complex is then detected. In one specific, non-limiting example detection of an immune complex is performed by immunoscintography. Other specific, non-limiting examples of immune complex detection include radiolocalization, radioimaging, or fluorescence imaging.

In one example, the antibody is directly linked to an effector molecule that is a detectable label. Specific, non-limiting examples of detectable labels include a radioactive isotope, an enzyme substrate, a co-factor, a ligand, a chemiluminescent agent, a fluorescent agent, a hapten, or an enzyme.

In another example, a humanized COL-1 antibody and a secondary antibody are administered to the subject for a sufficient amount of time for the humanized COL-1 antibody to form an immune complex with CEA on a tumor or cell, and for the secondary antibody to form an immune complex with the humanized COL-1 antibody.

In one embodiment, the humanized COL-1 antibody is complexed with the secondary antibody prior to their administration to the subject. In one specific, non-limiting embodiment, the secondary antibody is linked to a detectable label. In one embodiment, the immune complex, which includes CEA, the humanized COL-1 antibody, and the secondary antibody linked to a detectable label, is detected as described above.

A method of detecting tumors in a subject includes the administration of a humanized COL-1 antibody, such as FRV4, FRV7, or FRV10, complexed to an effector molecule, such as a radioactive isotope. After a sufficient amount of time has elapsed to allow for the administered radiolabeled antibody to localize to the tumor, the tumor is detected. In one specific, non-limiting example, a radiolabeled immune complex is detected using a hand held gamma detection probe. Primary tumors, metastasized tumors, or cells expressing CEA can be detected.

For example, a humanized COL-1 antibody complexed to an effector molecule, such as a radioactive isotope, is administered to a subject prior to surgery or treatment. In one specific embodiment, the detection step is performed prior to surgery to localize the tumor. In another embodiment, the detection step is performed during surgery, for example to detect the location of the tumor prior to removing it, as in radioimmunoguided surgery. A humanized COL-1 antibody complexed to an effector molecule, such as a radioactive isotope, can also be administered to a subject following surgery or treatment, to determine the effectiveness of the treatment, such as to ensure the complete removal of the tumor, or to detect a recurrence of the tumor.

In vitro detection methods are provided herein. These methods can be used to screen any biological sample to assess for the presence of a tumor or cell that expresses CEA. A biological sample can be obtained from a mammal, such as a human, suspected of having a tumor expressing CEA. In one embodiment the subject has a colorectal tumor. In other embodiments, the subject has a gastric tumor, a pancreatic tumor, a breast tumor, a lung tumor, an adenocarcinoma, or an ovarian tumor. Other biological samples that can be detected by the in vitro detection method include samples of cultured cells that express CEA.

Such samples include, but are not limited to, tissue from biopsies, autopsies, and pathology specimens. Biological samples also include sections of tissues, such as frozen sections taken for histological purposes. Biological samples further include body fluids, such as blood, serum, saliva, or urine.

A kit is provided herein for detecting a CEA-expressing tumor or cell. Kits for detecting a CEA-expressing tumor or cell will typically include a humanized COL-1 antibody that specifically binds CEA, such as FRV4, FRV7, or FRV10. An antibody fragment, such as an Fv fragment can be included in the kit. The antibody can also be provided as an immunoconjugate. Thus, in several examples, the antibody is conjugated to a detectable label, such as a radioactive isotope, an enzyme substrate, a co-factor, a ligand, a fluorescent agent, a hapten, an enzyme, or a chemiluminescent agent.

The kit can further include instructional materials disclosing means of use of an antibody that specifically binds CEA, such as FRV4, FRV7, or FRV10, or a fragment thereof. The instructional materials can be written, in an electronic form (for example, computer diskette or compact disk) or may be visual (for example, video files). The kits can also include additional components to facilitate the particular application for which the kit is designed. Thus, for example, the kit can additionally contain a means of detecting a label (for example, enzyme substrates for enzymatic labels, filter sets to detect fluorescent labels, appropriate secondary labels such as a secondary antibody, or the like). In one example, the kit contains a secondary antibody that is conjugated to a detectable label. Kits can additionally include buffers and other reagents, such as an antigen (for example, purified CEA) routinely used for the practice of a particular method, or of use in the preparation of a suitable control. Such kits and appropriate contents are well known to those of skill in the art.

The invention is illustrated by the following non-limiting Examples.

EXAMPLES

Example 1

Methods Used to Generate Antibodies Derived from HuCOL-1$_{AbrCDR}$

In the experiments disclosed herein, the dispensability of some of the murine framework residues that were deemed crucial and consequently retained in HuCOL-1$_{AbrCDR}$ has been tested. Several new antibodies derived from HuCOL-1$_{AbrCDR}$ were generated by using site-specific mutagenesis to replace some of the murine framework residues with their counterparts in the human templates. The HuCOL-1$_{AbrCDR}$-derived antibodies were tested for their (a) antigen-binding activity and (b) reactivity to sera from patients who had earlier been administered mCOL-1 in a clinical trial. One such antibody, FRV10, contains only 7 murine residues in its V$_H$ framework versus 17 murine residues present in the V$_H$ framework of the parental HuCOL-1$_{AbrCDR}$ (see FIG. 2). Compared with HuCOL-1$_{AbrCDR}$, FRV10 shows a lower reactivity to the anti-V region antibodies present in the patients' sera, while its Ag-binding affinity is unexpectedly comparable to that of the parental HuCOL-1$_{AbrCDR}$ antibody. Framework variant FRV10 exhibits low sera reactivity and is therefore a more useful clinical reagent against human carcinomas than its predecessors. Thus, as disclosed herein, humanization of an antibody can be experimentally optimized, in terms of maintaining antigen binding and minimizing immunogenicity, by the judicious manipulation of framework residues.

The following methods were used in the experimental studies:

Synthetic Oligonucleotides:

Oligonucleotide primers listed below were used for site-specific mutagenesis of the V$_H$ domain of HuCOL-1$_{AbrCDR}$ to generate FRV10. They were supplied by Gene Probe Technologies (Gaithersburg, Md.). The mutagenic bases are underlined, the positions of the residue changes are parenthetically enclosed, and the sequences recognized by restriction endonucleases are in bold.

V$_H$ primers:

| | |
|---|---|
| SEQ ID NO: 19 3'V$_H$ (1) | 5'-CAGCTGCACCTGGGAGTGCAC-3' |
| SEQ ID NO: 20 3'V$_H$ (12) | 5'-CCCCAGGTTTCTTCACCTCAGCGC-3' |
| SEQ ID NO: 21 3'V$_H$ (20) | 5'-CCTTGCAGGACACCTTCACGGAAGC-3' |
| SEQ ID NO: 22 3'VH (27) | 5'-TTTAATGTTGTATCCAGATGC-3' |
| SEQ ID NO: 23 3'V$_H$ (38) | 5'AAGCCCTTGTCCAGGGGCCTGCCTCACCCAGTGC-3' |
| SEQ ID NO: 24 5'V$_H$ (48) | 5'-CCTGGACAAGGGCTTGAGTGGATGGGATGGATTG-3' |
| SEQ ID NO: 25 5'V$_H$ (66) | 5'-TTCCAGGGCAGGGCCACCATG-3' |
| SEQ ID NO: 26 5'V$_H$ (67) | 5'-CAGGGCAGGGTCACCATGACC-3' |
| SEQ ID NO: 27 5'V$_H$ (78, 80) | 5'-CACGACGGTCTACATGGAGCTGAGC-3' |

The sequences of the end primers that were used for DNA amplification of the desired V$_H$ genes were as follows:

5'V$_H$:
5'-CTAGAATTCCACCATGGAGTGGTCC-3'  (SEQ ID NO: 28)

3'V$_H$
5'-TGGGCCCTTGGTGGAGGCTGA-3'  (SEQ ID NO: 29)

The 5' V$_H$ end primer carries an EcoRI restriction endonuclease site whereas the 3' V$_H$ end primer carries a unique ApaI site located 17 bp downstream from the start of the human CH1 domain.

DNA Mutagenesis and Sequencing:

All PCR amplifications were carried out as described previously (Gonzales et al., *Mol. Immunol.*, 40:337-49, 2003). Essentially, the desired changes were incorporated in the V$_H$ gene by multiple steps of PCR-induced mutagenesis using the primers described above and the V$_H$ gene of HuCOL-1$_{ABR}$ as the initial template.

Expression Vector and Generation of Expression Constructs:

The synthesized V$_H$ gene was sequenced (Gonzales et al., 2003), then inserted into a pre-existing construct in-frame with the human CH gene. The gene encoding the heavy chain of FRV10 was liberated from this construct through the unique EcoRI/NotI site and subcloned into the pIZ/V5-His insect cell expression vector (Invitrogen). This pIZ/V5-His derived expression construct was then co-transfected with a pBN/V5-His (Invitrogen) derived expression construct containing the gene encoding the light chain of HuCOL-1$_{AbrCDR}$ into Sf9 insect cells. The pIZ/V5-His vector carries the zeocin resistance gene whereas pIB/V5-His carries the blasticidin resistance gene. Transfectomas secreting the desired antibody were grown in serum-free insect cell medium, Sf-900 II SFM. The antibody was purified using protein A-agarose column chromatography (Gonzales, et al., 2003; De Pascalis et al., *Clin Cancer Res.*, 9:5521-31, 2003). Details of the transfection procedure and production of recombinant antibody from Sf9 insect cells have been described by De Pascalis et al. (2003).

Mammalian cell culture and production of recombinant antibodies: To develop transfectants expressing HuCOL-$1_{AbrCDR}$ and HuCOL-$1_{AbrCDR}$ antibodies with framework-substitutions, CHOdhfr⁻ cells were transfected with the pDC-Mdhfr derived expression construct using liposome-mediated DNA transfer (Lipofectamine Plus, Invitrogen) according to the guidelines of the manufacturer. Following transfection, cells were incubated at 37° C. in DMEM/F12 medium overnight, and were then trypsinized and seeded in 96-well plates at $2 \times 10^4$ cells per well in selection medium (alpha MEM, 10% dialyzed fetal bovine serum, 550 µg/ml G418). After 2 weeks of selection, the culture supernatants of the stable transfectants were monitored by ELISA assay and Western blotting.

Purification of recombinant antibodies: The highest antibody-producing clones were grown in CHO-SFM II serum-free medium (Invitrogen, Carlsbad, Calif.) supplemented with 550 µg/ml G418. Cell culture supernatants were collected and centrifuged at 2,000×g for 10 minutes to remove cellular debris. The supernatant was then loaded on a protein A agarose column (Invitrogen, Carlsbad, Calif.) equilibrated in 20 mM Tris-HCl buffer (pH 7.5). The bound protein was eluted from the column with 0.1 M glycine hydrochloride (pH 2.5) and the pH of the eluted material was immediately adjusted to 7.4 with 1.0 M Tris (pH 8.0). The protein was concentrated using Centricon 30 (Amicon, Beverly, Mass.) and buffer-exchanged in PBS (pH 7.4). The protein concentration was determined using a Bio-Rad protein assay kit (Bio-Rad Laboratories, Hercules, Calif.) based on the method developed by Bradford (Bradford, *Anal Biochem* 72:248-254, 1976). The purity of the antibody preparation was evaluated using the Agilent 2100 Bioanalyzer system (Agilent Technologies, Waldronn, Germany), under reducing and non-reducing conditions, using the Protein 200 LabChip kit (Agilent Technologies).

ELISA: Enzyme linked immunoassay (ELISA) was carried out by coating 96-well polyvinyl microtiter plates with Fcγ-fragment-specific goat anti-human IgG (100 ng/well) (Jackson ImmunoResearch Laboratories, West Grove, Calif.) or with CEA (100 ng/well) (Research Diagnostic Inc., Flanders, N.J.) to test for the production of Ig by the transfected mammalian cells and to assess the antigen reactivity of the purified antibodies, respectively. To detect reactivity of the samples to the ELISA plates, the SureBlue™ detection reagent was used (KPL, Gaithersburg, Md.) according to the manufacturer's instructions. The details of the assay procedure have been reported previously (De Pascalis et al., *J Immunol.*, 169:3076-3084, 2002, Gonzales et al., *Mol. Immunol.*, 40:337-349, 2003).

Competition RIA: The relative antigen-binding affinity of HuCOL-1, HuCOL-$1_{AbrCDR}$ and HuCOL-$1_{AbrCDR}$ antibodies with framework-substitutions was determined using a competition RIA as described previously (De Pascalis et al., *J Immunol.*, 169:3076-3084, 2002). Twenty-five µl of serial dilutions of the antibodies to be tested, as well as mCOL-1, chimeric COL-1, and HuCOL-1 (positive controls) and HuIgG (negative control), prepared in 1% BSA in PBS, were added to microtiter plates containing 10 ng of BSM saturated with 5% BSA in PBS. $^{125}$I-labeled mCOL-1 (100,000 cpm in 25 μl) was then added to each well. After an overnight incubation at 4° C., the plates were washed and the bound radioactivity was counted in a γ-scintillation counter. The relative affinity constants were calculated by a modification of the Scatchard method (Frankel et al., *Mol. Immunol.,* 16:101-106, 1979).

Flow cytometric (FACS) analysis: To evaluate the ability of HuCOL-$1_{AbrCDR}$-derived antibodies to bind to cell-surface CEA, a previously described method (Nicolet et al., *Tumour Biol.,* 18:356-366, 1997) was used for FACS analysis. Jurkat cells ($1\times10^6$), expressing CEA, were resuspended in cold $Ca^{++}$ and $Mg^{++}$ free Dulbecco's PBS and incubated with the antibodies (HuCOL-1, HuCOL-$1_{AbrCDR}$, or HuCOL-$1_{AbrCDR}$ antibodies with framework-substitutions) for 30 minutes on ice. A human IgG was used as an isotype control. After one washing cycle, the cell suspension was stained with FITC-conjugated mouse anti-human antibody (PharMingen, San Diego, Calif.) for 30 minutes on ice. After a second washing cycle was performed, the samples were analyzed with a FACScan (Becton Dickinson, Mountain View, Calif.) using CellQuest for Macintosh. Data from the analysis of 10,000 cells were obtained.

Immunoadsorption of patient serum: Stored patients' sera, from a phase I clinical trial (Yu et al., *J. Clin. Oncol.,* 14:1798, 1996), which involved the administration of $^{131}$I-mCOL-1 to gastrointestinal carcinomas patients, were used to assess sera reactivity of the HuCOL-$1_{AbrCDR}$-derived antibodies. Several sera were tested for the presence of anti-V region antibodies to mCOL-1. The sera, however, contain circulating antigens and anti-murine Fc antibodies, which could interfere with the binding of the HuCOL-$1_{AbrCDR}$-derived antibodies to the anti-V region antibodies. To circumvent this problem, the circulating CEA and anti-murine Fc antibodies were removed by sequential pre-adsorption of the sera with a purified mCOL-4 that reacts with epitopes of CEA different from the one recognized by mCOL-1. mCOL-6 has the same isotype as that of mCOL-1. For pre-adsorption, serum samples were added to mCOL-6 coupled to Reacti-gel according to the method of Hearn et al. (Hearn et al., *J. Chromatogr.,* 185:463, 1979). The mixtures were incubated overnight at 4° C. with end-to-end rotation and centrifuged at 1000×g for 5 minutes. Pre-adsorption was repeated until the supernatants displayed no detectable anti-murine Fc activity. To detect anti-V region antibodies by Surface Plasmon Resonance (SPR), the pre-adsorbed serum was used as a mobile reactant. Proteins were immobilized on carboxymethylated dextran CM5 chips (Biacore, Piscataway, N.J.) by amine coupling using standard procedure (Johnsson et al., *Anal. Biochem.* 198:268, 1991; Schuck et al., Measuring protein interactions by optical biosensors. In *Current Protocols in Protein Science*, Vol. 2. J. E. Coligan, B. M. Dunn, H. L. Ploegh, D. W. Speicher, and P. T. Wingfield, eds. John Wiley & Sons, New York, N.Y., p. 20.2.1, 1999). HuCOL-1 was immobilized on the surface of flow cell 1, while the surface of flow cell 2 was coated with an unrelated protein, rabbit gamma globulin (Biorad, Hercules, Calif.).

Sera reactivity: The reactivity of COL-1 humanized antibodies to anti-V region antibodies was determined using a recently developed SPR-based competition assay (Gonzales et al., *J. Immunol. Methods,* 268:197-210, 2002). Competition experiments were performed at 25° C. using a CM5 sensor chip containing HuCOL-1 in flow cell 1, and rabbit gamma globulin (Biorad), as a reference, in flow cell 2. Typically, mCOL-1, HuCOL-1, HuCOL-$1_{AbrCDR}$, or HuCOL-$1_{AbrCDR}$-derived antibodies, were used at different concentrations, to compete with the antibody immobilized on the sensor chip for binding to serum anti-V region antibodies. Patient's serum with or without the competitor (mCOL-1, HuCOL-1, HuCOL-$1_{AbrCDR}$, or HuCOL-$1_{AbrCDR}$-derived antibodies) was applied across the sensor surface using a recently developed sample application technique (Abrantes et al., *Anal. Chem.,* 73:2828, 2001) at the unidirectional flow of 1 μl/min. The sample was centered across the sensor surfaces and an oscillatory flow was applied at a rate of 20 μl/minute. After measuring the binding for 1000 seconds, the unbound samples were removed from the surfaces by washing with running buffer using a flow rate of 100 μl/min, and the surfaces were regenerated with a 1 minute injection of 10 mM glycine (pH 2.0). The percent binding at each antibody concentration was calculated as follows:

% binding=[slope of the signal obtained with competitor (serum+mCOL-1, HuCOL-1, or HuCOL-1$_{AbrCDR}$)/slope of the signal obtained without competitor (serum only)]×100.

IC$_{50}$ for each antibody, the concentration required for 50% inhibition of the binding of the serum to either mCOL-1, HuCOL-1, or HuCOL-1$_{AbrCDR}$, was calculated.

Example 2

HuCOL-1$_{AbrCDR}$-Derived Antibodies

This example describes the HuCOL-1$_{AbrCDR}$-derived antibodies with framework residue substitutions. An examination of the V$_L$ sequences of mCOL-1 and the human antibody VJI'CL reveals that 75 out of the 90 framework residues are identical (De Pascalis et al., *J Immunol.*, 169:3076-3084, 2002). Of the 15 differences, 5 residues were deemed crucial and were grafted onto the human template, along with the abbreviated CDRs, in generating the humanized COL-1 antibody HuCOL-1$_{AbrCDR}$. The V$_H$ sequences of mCOL-1 and MO30 share 57 identities in 87 framework residues. Out of the 30 framework differences, 17 murine residues were included in HuCOL-1$_{AbrCDR}$. The murine framework residues included in the V domains of the HuCOL-1$_{AbrCDR}$ are at positions 4, 60, 78, 85, and 104 in V$_L$, and at positions 1, 12, 20, 27, 28, 29, 30, 38, 48, 66, 67, 71, 78, 80, 96, 97, and 105 in V$_H$ (Kabat positions; numbering convention of Kabat et al. (*Sequence of Proteins of Immunological Interests*, 5$^{th}$ ed., p. NIH Publication No. 91-3242, U.S. Department of Health and Human Services, National Institutes of Health, Bethesda, Md., 1991)).

Analysis of the known three-dimensional structures of antibody:antigen complexes available in the protein databank database (Abola et al., *Methods Enzymol* 277:556-571, 1997) reveals that the residues at the positions enumerated above are important in keeping the overall structure of the combining site, because they are either buried or implicated in the direct interaction with the antibody (Amit et al., *Science* 233:747-753, 1986; Colman et al., *Nature* 326:358-363, 1987; Fischmann et al., *J. Biol. Chem.*, 266:12915-12920, 1991; Padlan et al., *Proc. Natl. Acad. Sci. USA*, 86:5938-5942, 1989; Sheriff et al., *Proc. Natl. Acad. Sci. USA*, 84:8075-8079, 1987; Tulip et al., *J. Mol. Biol.*, 227:122-148, 1992), contact with CDRs (Chothia et al., *J. Mol. Biol.*, 196:901-917, 1987; Chothia et al., *Nature*, 342:877-883, 1989; Tramontano et al., *J. Mol. Biol.*, 215:175-182, 1990), or in the V$_L$/V$_H$ interaction (Padlan, *Mol. Immunol.*, 31:169-217, 1994). The crucial nature of these murine framework residues, however, has not been validated in the case of COL-1. It is likely that some of the framework residues deemed crucial to maintain antigen reactivity of other antibodies are not that essential for the antigen:antibody interaction of COL-1. Several HuCOL-1$_{AbrCDR}$-derived antibodies were designed to test the indispensability of some of the murine framework residues for the antigen-binding reactivity of COL-1 by replacing them with the corresponding residues in the human antibodies.

FRV2 was generated by replacing the murine V$_L$ framework residues at Kabat positions 4, 78, and 104 of HuCOL-1 AbrCDR with the corresponding residues of the human antibody VJI'CL. FRV3 contains two additional changes at Kabat positions 60 and 85, making all the framework residues in the V$_L$ of this antibody human. To generate FRV4, the V$_H$ framework residues at Kabat positions 20, 38, 48, 66, 78, and 80 of HuCOL-1$_{AbrCDR}$ were replaced with the corresponding residues of the human antibody MO30. In addition to all the substitutions present in FRV4, substitutions at Kabat positions 27 and 67 were also included in FRV7. FRV10 contains two additional changes at Kabat positions 1 and 12. In this V$_H$ antibody, only seven murine residues located at Kabat positions 28, 29, 30, 71, 96, 97, and 105 of mCOL-1 are included. The amino acid sequences of the V$_L$ and V$_H$ frameworks of HuCOL-1$_{AbrCDR}$ and the FRV4, FRV7, and FRV10 variants are shown in FIG. 2. Antibodies containing different combinations of the HuCOL-1$_{AbrCDR}$-derived V$_L$ and V$_H$ chains are listed in Table I (above).

Example 3

Expression of HuCOL-1$_{AbrCDR}$-Derived Antibodies in CHOdhfr⁻ Cells

The expression constructs of the genes encoding the H and L chains of HuCOL-1$_{AbrCDR}$ and HuCOL-1$_{AbrCDR}$-derived antibodies having framework-substitutions were introduced into CHOdhfr⁻ cells. The supernatants harvested from the G418 resistant transfectants were assayed for Ig production by ELISA and Western blot analysis as described above. Most of the transfectants, like those generated by the control constructs of HuCOL-1$_{AbrCDR}$, were found to be positive for Ig production. When the culture supernatants were assayed for their reactivity to CEA, most of the HuCOL-1$_{AbrCDR}$ derived antibodies, like those of HuCOL-1$_{AbrCDR}$ transfectomas, were positive. The highest producing clone of each construct was cultured under identical conditions, and the secreted antibodies were purified from the culture supernatants. The purity of the antibody preparations was verified by the Agilent 2100 Bioanalyzer system, using a Protein 200 LabChip. The profiles of all recombinant antibodies were identical under reducing and non-reducing conditions. Under reducing conditions all antibodies yielded two protein bands of approximately 24-27 kDa and 60 kDa. These molecular masses are in conformity with those of the Ig L and H chains, respectively.

Example 4

Relative CEA-binding of HuCOL-1$_{AbrCDR}$-Derived Antibodies from COL-1

An ELISA was carried out to obtain preliminary information about the CEA reactivity of the HuCOL-1$_{AbrCDR}$-derived antibodies, prior to performing competition radioimmunoassay (RIA) experiments. Results of the ELISA assay showed that all of the HuCOL-1$_{AbrCDR}$-derived antibodies were reactive with CEA, albeit to varying degrees (FIGS. 3A and 3B).

Competition RIA experiments were performed to determine the relative CEA-binding affinity of chimeric COL-1, HuCOL-1, HuCOL-1$_{AbrCDR}$, and the different HuCOL-1$_{AbrCDR}$-derived antibodies. Serial dilutions of unlabeled antibodies were used to compete with the binding of $^{125}$I-mCOL-1 (FIGS. 4A, 4B and 4C) to CEA. Only the variants with substitutions limited to the V$_H$ domain (FRV4, FRV7, and FRV10) were able to completely inhibit the binding of $^{125}$I-mCOL-1 to CEA. The competition profiles of FRV4, FRV7, and FRV10 were comparable to that of mCOL-1, chimeric COL-1, HuCOL-1, and HuCOL-1$_{AbrCDR}$. Surprisingly, while the competition profiles of HuCOL-1$_{AbrCDR}$ is shifted slightly to the right, as compared to HuCOL-1 (corresponding to 28.4 ng of antibody required for 50% inhibition of $^{125}$I-mCOL-1 binding to CEA), the competition profiles of FRV4, FRV7, and FRV10 are shifted slightly to the left, as compared to HuCOL-1 (corresponding to 14.7 ng of antibody required for 50% inhibition of $^{125}$I-mCOL-1 binding to CEA) (FIGS. 4A, 4B and 4C). The shift to the left of the competition profiles corresponds to an increase in the CEA-binding affinities of FRV4, FRV7, and FRV10, compared to HuCOL-1, calculated to be $2.51 \times 10^8$ M$^{-1}$, $3.07 \times 10^8$M$^{-1}$, and $3.04 \times 08$ M$^{-1}$, respectively (Table II).

TABLE II

Ka Competition radioimmunoassay

| Variant Designation | Ka (relative affinity constant) × 10$^8$ M$^{-1}$ | Fold Difference |
|---|---|---|
| mCOL-1 | 2.74 | 1.0 |
| cCOL-1 | 1.99 | 1.4 |
| HuCOL-1 | 2.78 | 1.0 |
| HuCOL-1$_{AbrCDR}$ | 2.30 | 1.2 |
| FRV2 | 0.29 | 9.5 |
| FRV3 | 0.32 | 8.6 |
| FRV4 | 2.51 | 1.1 |
| FRV5 | 1.01 | 2.7 |
| FRV6 | 1.00 | 2.8 |
| FRV7 | 3.07 | 0.9 |
| FRV8 | 0.77 | 3.6 |
| FRV9 | 0.61 | 4.5 |
| FRV10 | 3.04 | 0.9 |
| FRV11 | 0.61 | 4.5 |
| FRV12 | 0.49 | 5.6 |

The amount of antibody required for 50% inhibition of the binding of $^{125}$I mCOL-1 to CEA was 24.6, 28.4, 20.6, 21, and 14.7 ng for HuCOL-1, HuCOL-1$_{AbrCDR}$, FRV4, FRV7, and FRV10, respectively (Table III). These results, calculated from the linear parts of the graph shown in FIGS. 4A, 4B and 4C, are in conformity with the relative affinity constants (Ka) of $2.74 \times 10^8$, $1.99 \times 10^8$, and $2.78 \times 10^8$ for mCOL-1, chimeric COL-1, HuCOL-1, and HuCOL-1$_{AbrCDR}$, respectively (Table II).

TABLE III

Relative CEA-binding of HuCOL-1$_{AbrCDR}$-derived antibodies

| Variant Designation | Amount of Ab required for 50% Inhibition (ng) | Ka (relative affinity constant) × 10$^8$ M$^{-1}$ |
|---|---|---|
| HuCOL-1 | 24.6 | 2.78 |
| HuCOL-1$_{AbrCDR}$ | 28.4 | 2.32 |
| FRV4 | 20.6 | 2.51 |
| FRV7 | 21 | 3.07 |
| FRV10 | 14.7 | 3.04 |

Example 5

Binding of HuCOL-1$_{AbrCDR}$-Derived Antibodies to Cell Surface CEA

Flow cytometric analysis was used to measure the binding of HuCOL-1$_{AbrCDR}$-derived antibodies to the CEA expressed on the cell surface of the retrovirally transduced tumor cell line, MC38 (Robbins et al., *Cancer Res.*, 51:3657, 1991). No significant differences were found in the mean fluorescence intensity or in the percentage of cells that was reactive with HuCOL-1$_{AbrCDR}$ and its variants (FIGS. 5A-5D). The percentage of gated cells, calculated after exclusion of irrelevant binding, was between 33 and 38. The mean fluorescence intensities were between 18 and 20, when 1 μg of each antibody was used.

Example 6

Reactivity of HuCOL-1$_{AbrCDR}$-Derived Antibodies to Patients' Sera

A measure of the immunogenicity of a variant antibody is its in vitro reactivity to the sera of patients who were administered the mCOL-1 antibody in a clinical trial. To assess the potential immunogenicity of HuCOL-1, HuCOL-1 AbrCDR, and FRV10 in patients, the antibodies were characterized for their reactivity to sera from gastrointestinal carcinoma patients who were administered $^{131}$I-mCOL-1 in a phase I clinical trial (Yu et al., *J. Clin. Oncol.*, 14:1798, 1996). As described in Example 1, any circulating CEA and anti-murine Fc antibodies were removed from the sera by immunoadsorption with mCOL-6 and mCOL-4, two murine anti-CEA antibodies of IgG$_1$ and IgG$_{2a}$ isotypes, respectively. Specific binding profiles of immobilized HuCOL-1 to the sera of patients MB and EM showed that the pre-adsorbed sera contained antibodies against the variable regions of mCOL-1.

Sera reactivity of the humanized antibodies was determined by their ability to compete with HuCOL-1 immobilized on a sensor chip for binding to the mCOL-1 anti-V region antibodies present in the patients' sera.

Sensorgrams showing the inhibition by HuCOL-1, HuCOL-1$_{AbrCDR}$, and FRV10 of the binding of EM serum to the HuCOL-1 surface and the competition of all three antibodies with patient MB's serum were also generated. FIG. 6 shows the competition profiles generated by the three humanized antibodies when they were used to compete with the HuCOL-1 immobilized on the sensor chip for binding to the anti-V region antibodies to COL-1 present in the sera of patients EM (FIG. 6A) and MB (FIG. 6B). The competition profiles of the antibodies for both patients' sera follow the same pattern, with HuCOL-1 as the most reactive and FRV10 as the least reactive. The IC$_{50}$ values, the concentrations of the competitor antibody required for half-maximal inhibition of the binding of HuCOL-1 to the patient's serum, were calculated from the competition curves and are given in Table IV. A higher IC$_{50}$ value indicates a decreased reactivity to the serum, suggesting a potentially reduced immunogenicity of the antibodies in patients. Compared with those of HuCOL-1 for both patients' sera, the IC$_{50}$ values of HuCOL-1$_{AbrCDR}$ are 1.5-fold higher while those of FRV10 are approximately 5- to 6-fold higher.

TABLE IV

Reactivity of the humanized Abs with patients' sera[a]

| Competitor Antibody | Patient EB (nM) | Patient MB (nM) |
|---|---|---|
| HuCOL-1 | 1.9 | 4.9 |
| HuCOL-1$_{AbrCDR}$ | 2.9 | 6.9 |
| FRV10 | 9.7 | 28.5 |

[a]Competitor antibody concentrations required for the half-maximal inhibition of the binding of patients' sera to immobilized HuCOL-1 were calculated.

Example 7

Systemic Radioimmunotherapy Alone or In Combination with Vaccine Therapy in a Mouse Model The administration of a radiolabeled antibody to a mouse model was used to assess if the phenotype of tumor cells can be altered. CEA transgenic mice were implanted with either MC32a (CEA+) or MC38 (CEA−) tumor cells subcutaneously. Fifteen days later, mice were injected intravenously with different doses (0, 25, 50, 100, and 150 µCi) of Y-90 (Yttrium-90)-labeled mCOL-1 antibody. After 96 hours, mice were sacrificed and different organs are used for a biodistribution study. The results demonstrate that the MC32a tumors showed a statistically significant preferential radiation uptake, compared to MC38 tumors (most notably at 50 µCi and at 100 µCi of Y-90-labeled mCOL-1).

In addition, CEA transgenic (CEA-Tg) mice were implanted with MC32a (CEA+) or MC38 (CEA−) tumor cells subcutaneously. Fifteen days later, mice were injected intravenously with different doses (0, 50, 100, and 150 µCi) of Y-90 labeled mCOL-1 antibody. After 96 hours, tumor cells were isolated and stained for flow cytometric analysis. The data demonstrated that Y-90-labeled mCOL-1 antibody upregulates Fas on CEA positive, but not on CEA negative, tumor cells.

Figure 7A:
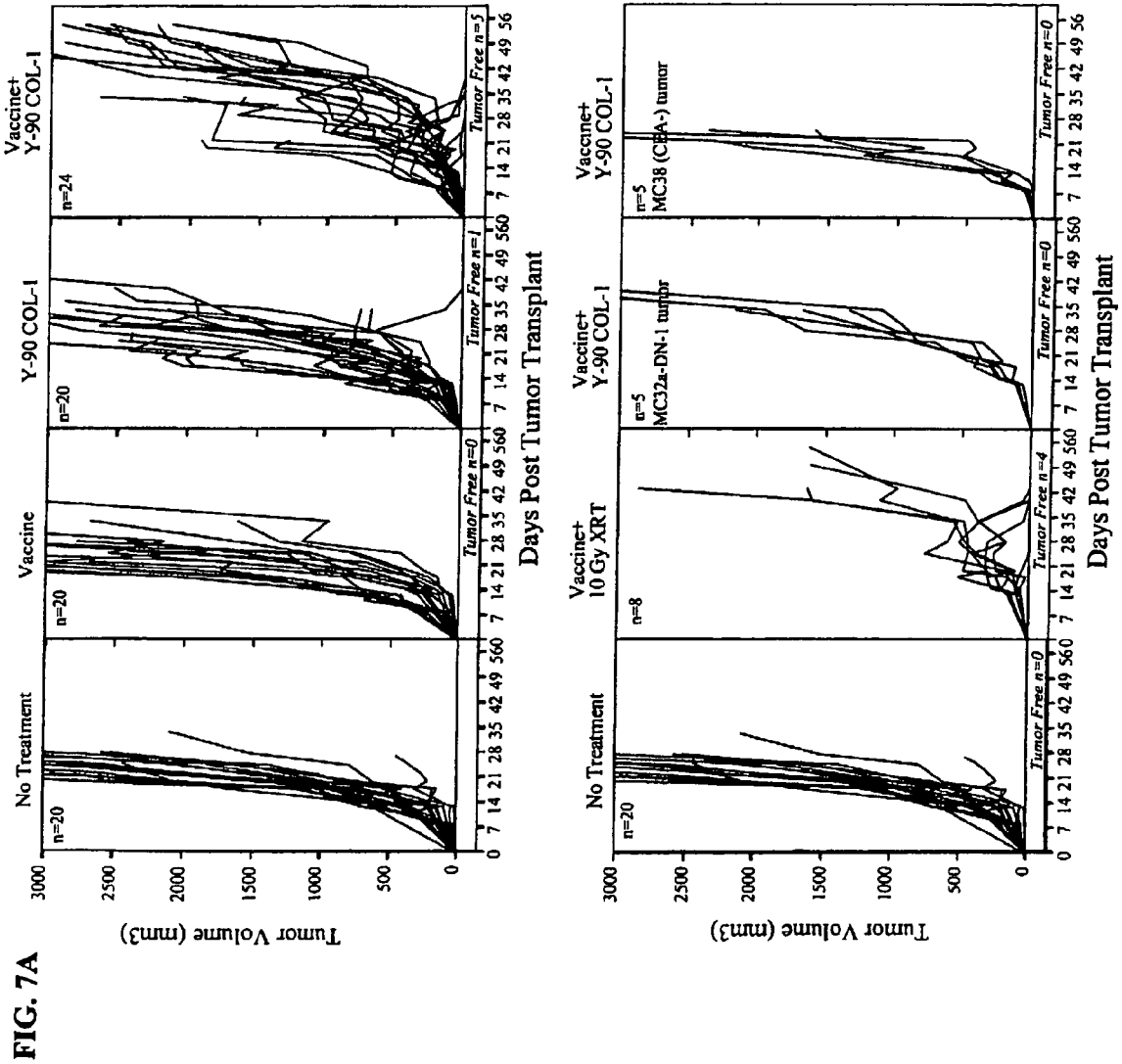
Figure 7B:
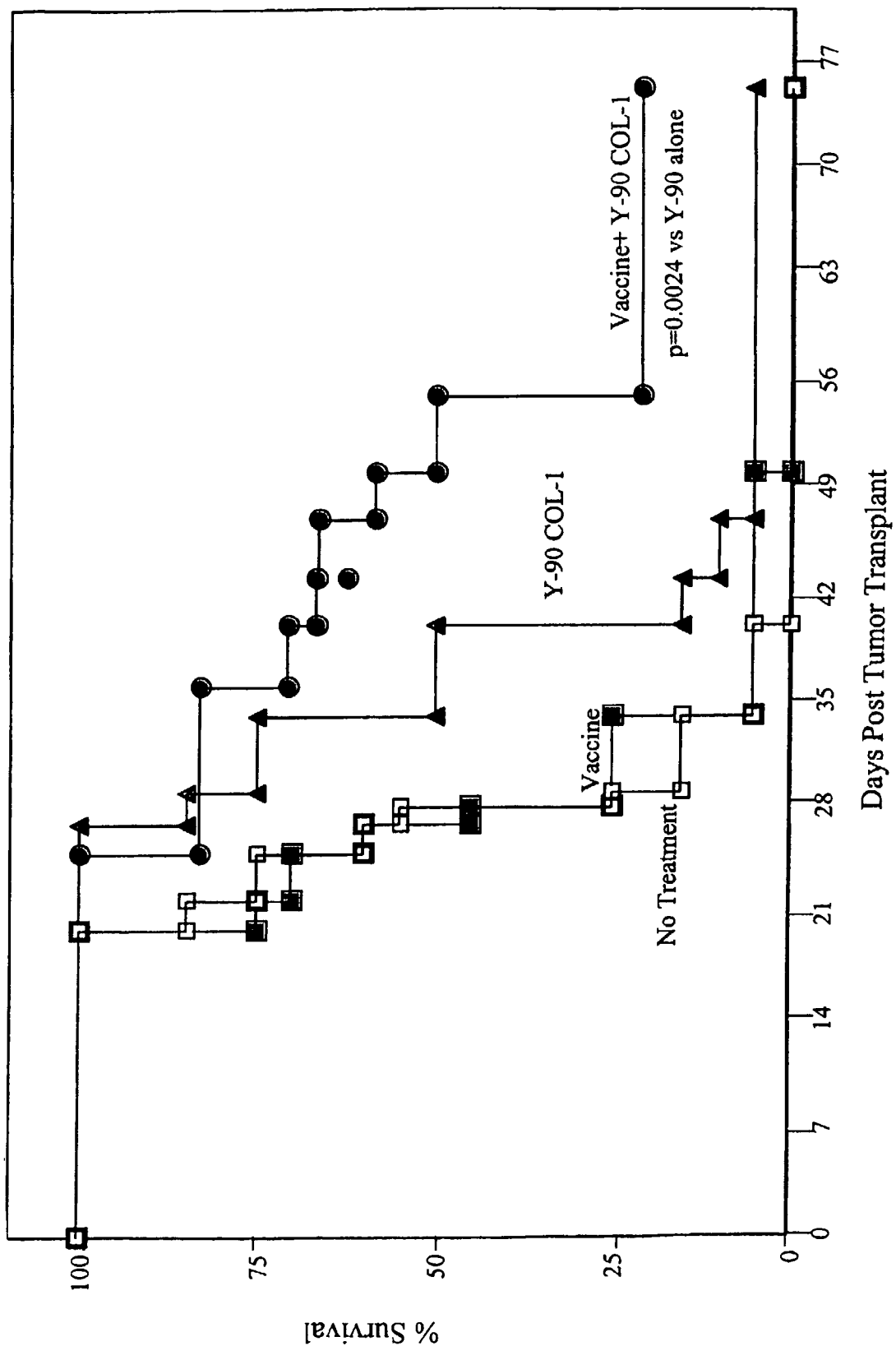

In separate experiments, CEA-Tg mice were injected with either MC32a (CEA+), MC38 (CEA−), or MC32 DN1Fas (defective Fas) tumor cells subcutaneously. Mice were treated with vaccine alone, with Y-90-labeled mCOL-1 antibody alone, or a combination of vaccine and mCOL-1 antibody. The TRICOM vaccine regimen consisted of a prime and boost strategy using vaccinia and fowlpox recombinants expressing CEA (rV-CEA/TRICOM and rF-CEA/TRICOM, respectively) and three costimulatory molecules (B7-1, ICAM-1, LFA-3). All of the vaccines were co-administered with rF-GM-CSF. Tumor volume and survival were monitored for 77 days. Tumor volume measurements indicated that mice receiving the combination of Y-90-labeled mCOL-1 antibody and vaccine had a smaller tumor volume over the course of the 77 days, compared to mice receiving the vaccine or antibody alone, and that the rate of increase in tumor volume was slower over this time period for the mice receiving the combination therapy, compared to the mice receiving the vaccine or antibody alone. In addition, more combination therapy-treated animals remained tumor free at the end of this period (n=5), compared to vaccine-treated (n=0) or antibody-treated (n=1) animals (FIG. 7A). Survival measurements demonstrated that, at 77 days, a greater percentage of mice receiving Y-90-labeled mCOL-1 antibody survived compared to mice receiving vaccine alone, but that an even greater percentage of mice receiving the combination therapy survived than either vaccine alone or Y-90-labeled mCOL-1 antibody alone treated mice. In addition, the data demonstrated that the combination therapy-treated mice survived for a longer period before dying, compared to the vaccine- or antibody-treated mice (FIG. 7B).

The characterization of infiltrating cells from tumors treated with the combination of vaccine therapy and radiolabeled antibody was subsequently investigated. CEA-Tg mice were implanted with MC32 (CEA+) tumor cells subcutaneously. Fifteen days later, mice were injected intravenously with 100 mCi of Y-90-labeled mCOL-1 antibody, or vaccine alone, or combination of both vaccine and Y-90-labeled antibody. After four weeks following tumor implant, tumor cells were isolated and the infiltrating T cells were stained for flow cytometric analysis. FACS analysis demonstrated that CD3+ CD8+ T cells isolated from the tumor mass were not dead. In addition, FACS analysis demonstrated that mice treated with Y-90-labeled mCOL-1 antibody in combination with vaccine have a significant increase in the percentage of tumor infiltrating CEA specific CD8+ T cells (43.9% and 43.6% of gated cells) compared to mice treated with vaccine alone (25.3% and 22.2% of gated cells).

In addition, cellular immune responses to multiple tumor antigens after combined therapy with vaccine and Y-90-labeled mCOL1 were assessed. Three CEA-Tg mice per group were given MC38-CEA+ tumors subcutaneously. Eight days later, mice were vaccinated with rV-CEA/TRICOM admixed with rF-GM-CSF. On day 14, mice received 100 µCi Y-90-mCOL-1. On days 15, 22, and 29 mice were boosted with rF-CEA/TRICOM admixed with rF-GM-CSF. Responses from pooled splenic T cells from cured mice were analyzed two months following the tumor transplant for CEA protein and p53 MHC-II-peptide-specific proliferation and CEA, p53, and GP70 peptide-specific IFN-γ production. Control mice were age-matched CEA-Tg mice. The results obtained are presented in Table V.

TABLE V

| | Antigen[a] | | | | | | | | |
|---|---|---|---|---|---|---|---|---|---|
| | CEA (µg/ml) | | | p53 (µg/ml) | | | Peptide[b] | | |
| Treatment | 25 | 12.5 | 6.25 | 5 | 2.5 | 1 | CEA | p53 | GP70 |
| Vaccine + radiolabeled antibody | 10 | 3.3 | 1.7 | 3.2 | 3.0 | 1.6 | 6280 | 3560 | 36410 |
| Control | 1.0 | 1.7 | 1.4 | 0.6 | 0.7 | 0.6 | 570 | 1880 | 23970 |

[a]For proliferation, each value represents the stimulation index of the mean CPM of triplicate samples versus media. Standard deviation never exceeded 10%.
[b]For peptide-specific IFN-γ production, concentrations of peptides CEA, p53, and GP70 were 10, 2, and 1 µg/ml, respectively. Each value represents IFN-γ (pg/ml/$10^6$ cells/24 hr).

Thus, mice cured of tumors demonstrated CD4+ and CD8+ T-cell responses not only for CEA, but also for other tumor-derived antigens (gp70 and p53) over-expressed in a tumor, indicating the presence of a consequential antigen cascade.

This Example demonstrates that one dose (100 µCi) of radiolabeled antibody in combination with vaccine therapy is capable of inhibiting eight day established tumors. Also, the combination therapy results in a statistically significant increase in survival, compared to vaccine or radiotherapy alone. Thus, targeted tumor radiation, in combination with vaccine, promotes an effective antitumor response.

Example 8

Humanized COL-1 Antibody Testing in Patients

Patients and Sample Collection

Patients with recurrent colorectal cancer are assessed to determine the maximum tolerated dose of intravenously administered [177]Lutetium or yttrium-90 radiolabeled FRV4, FRV7, or FRV10 antibody. Colorectal cancer patients are given a test dose of 0.1 mg (intravenous bolus) of FRV4, FRV7, or FRV10 and are observed for 30 minutes prior to administration of the radiolabeled antibody. The radiolabeled antibody is given as an intravenous infusion over the course of a one hour time interval. Blood samples are collected prior to and at the end of the infusion, as well as 0.5, 1 and 2 hours following the completion of the infusion. In addition, blood samples are collected daily over the subsequent 7 days. Patients return for a follow-up examination at 3, 6 or 8 weeks. Blood samples are again collected during these visits. Sera are separated and stored at −20° C.

Determination of Patient Humoral Response

The sera from the patients are evaluated for the presence of human anti-murine antibodies (HAMA) in response to radiolabeled FRV4, FRV7, or FRV10 using the SPR-based assay described in Example 6, above. The sera are pre-absorbed with an mCOL-4 monoclonal antibody that recognizes an epitope of CEA which is different from the epitope recognized by the humanized COL-1 monoclonal antibody. Pre-absorption using the COL-4 antibody removes circulating CEA and anti-murine Fc antibodies from the sera. To monitor the sera-reactivity of the anti-variable antibodies in the pre-absorbed sera, FRV4, FRV7, or FRV10 are coated on the surface of flow cell 1 and a reference protein (HuIgG2a, bovine serum albumin, or rabbit gamma globulin) is immobilized on the surface of flow cell 2. A small, known volume of a patient serum sample us applied to each flow cell using the recently developed sample application technique previously described (Abrantes et al., *Anal. Chem.* 73:2828, 2001). Sensograms to flow cell 1 and flow cell 2 are generated and the response difference between the two cells is plotted for each serum sample, thus providing a measure of the anti-variable region response against the humanized COL-1 antibodies in each particular serum sample. Results indicate that the patients' sera have a minimal anti-variable region response against the FRV4, FRV7, or FRV10 antibodies.

Example 9

Systemic Radioimmunotherapy in Conjunction with Vaccine as Antitumor Treatment

Patients with recurrent colorectal cancer are assessed to determine if the administration of radiolabeled antibody, alone or in combination with a vaccine, can inhibit or suppress tumor growth in a subject. In this example, the humanized COL-1 antibodies FRV4, FRV7, and FRV10 are radiolabeled with the Y-90 (Yttrium-90) radioisotope and the subjects are injected intravenously with different doses (for example, 0, 50, 100, and 150 µCi) of Y-90 labeled FRV4, FRV7, or FRV10, alone or in combination with a vaccine. The vaccine regimen consists of a prime and boost strategy using recombinant vectors expressing CEA and costimulatory molecules. All of the vaccines are co-administered with GM-CSF.

The data demonstrate that one dose of radiolabeled antibody in combination with vaccine therapy is capable of inhibiting the growth of established tumors. Also, the combination therapy results in a statistically significant increase in survival, compared to vaccine or radiotherapy alone. Thus, targeted tumor radiation, in combination with vaccine, promotes an effective antitumor response.

This disclosure provides variants of a humanized COL-1 antibody. The disclosure further provides methods of diagnosing and treating tumors using these variant antibodies. It will be apparent that the precise details of the methods described may be varied or modified without departing from the spirit of the described invention. We claim all such modifications and variations that fall within the scope and spirit of the claims below.

We claim:

1. A humanized COL-1 monoclonal antibody, comprising: a heavy chain comprising an amino acid sequence as set forth in SEQ ID NO: 8 and a light chain comprising the amino acid sequence of SEQ ID NO: 4, wherein a framework residue at position 79 of SEQ ID NO: 8 and at least five additional framework residues in SEQ ID NO: 8 are substituted with an amino acid from a corresponding position in the amino acid sequence set forth as SEQ ID NO: 6, and wherein the humanized COL-1 antibody retains binding affinity for carcinoembryonic antigen (CEA) and has reduced immunogenicity, as compared to HuCOL-1$_{AbrCDR}$, deposited as ATCC Accession No. PTA-4644.

2. The humanized antibody of claim 1, wherein the at least five additional framework residues comprises framework residues at positions 20, 38, 48, 67, and 81 of the amino acid sequence of SEQ ID NO: 8.

3. The humanized antibody of claim 2, further comprising a substitution of a framework residue at position 27 of SEQ ID NO: 8 with an amino acid from a corresponding position in the amino acid sequence set forth as SEQ ID NO: 6.

4. The humanized antibody of claim 2, further comprising a substitution of a framework residue at position 68 of SEQ ID NO: 8 with an amino acid from a corresponding position in the amino acid sequence set forth as SEQ ID NO: 6.

5. The humanized antibody of claim 2, further comprising a substitution of a framework residue at positions 27 and 68 of SEQ ID NO: 8 with an amino acid from a corresponding position in the amino acid sequence set forth as SEQ ID NO: 6.

6. The humanized antibody of claim 2, further comprising a substitution of a framework residue at position 1 of SEQ ID NO: 8 with an amino acid from a corresponding position in the amino acid sequence set forth as SEQ ID NO: 6.

7. The humanized antibody of claim 2, further comprising a substitution of a framework residue at position 12 of SEQ ID NO: 8 with an amino acid from a corresponding position in the amino acid sequence set forth as SEQ ID NO: 6.

8. The humanized antibody of claim 2, further comprising a substitution of a framework residue at positions 1 and 12 of SEQ ID NO: 8 with an amino acid from a corresponding position in the amino acid sequence set forth as SEQ ID NO: 6.

9. The humanized antibody of claim 2, further comprising a substitution of a framework residue at positions 1, 12, 27, and 68 of SEQ ID NO: 8 with an amino acid from a corresponding position in the amino acid sequence set forth as SEQ ID NO: 6.

10. The humanized antibody of claim 1, wherein the residue at position 79 of SEQ ID NO: 8 is substituted with a valine.

11. The humanized antibody of claim 2, wherein the residue at position 20 of SEQ ID NO: 8 is substituted with a valine.

12. The humanized antibody of claim 2, wherein the residue at position 38 of SEQ ID NO: 8 is substituted with an arginine.

13. The humanized antibody of claim 2, wherein the residue at position 48 of SEQ ID NO: 8 is substituted with a methionine.

14. The humanized antibody of claim 2 wherein the residue at position 67 of SEQ ID NO: 8 is substituted with an arginine.

15. The humanized antibody of claim 2, wherein the residue at position 81 of SEQ ID NO: 8 is substituted with a methionine.

16. The humanized antibody of claim 2, wherein the residue at position 20 is substituted with a valine, the residue at position 38 is substituted with an arginine, the residue at position 48 is substituted with a methionine, the residue at position 67 is substituted with an arginine, the residue at position 79 is substituted with a valine, and the residue at position 81 is substituted with a methionine.

17. The humanized antibody of claim 16, further comprising a substitution of a residue at position 27 of SEQ ID NO: 8 with a tyrosine and a substitution of a residue at position 68 of SEQ ID NO: 8 with a valine.

18. The humanized antibody of claim 17, further comprising a substitution of a residue at position 1 of SEQ ID NO: 8 with a glutamine and a substitution of a residue at position 12 of SEQ ID NO: 8 with a lysine.

19. The humanized antibody of claim 1, further comprising a detectable label.

20. The humanized antibody of claim 19, wherein the detectable label is a fluorescent or radioactive molecule.

21. A composition comprising a functional fragment of the humanized antibody of claim 1, wherein the functional fragment specifically binds CEA.

22. The composition of claim 21, wherein the fragment comprises an Fv, an Fab, or an F(ab')$_2$.

23. A composition comprising a functional fragment of a humanized antibody, wherein the humanized antibody comprises a light chain of the humanized antibody comprising an amino acid sequence as set forth in SEQ ID NO: 9 and a heavy chain of the humanized antibody comprising an amino acid sequence as set forth in SEQ ID NO: 12, and wherein the functional fragment specifically binds CEA.

24. A pharmaceutical composition comprising a therapeutically effective amount of the humanized antibody of claim 1 in a pharmaceutically acceptable carrier, wherein the humanized antibody inhibits tumor growth.

25. The pharmaceutical composition of claim 24, further comprising an immunogenic agent that exhibits an immunogenic response and further inhibits tumor growth.

26. A method for treating a subject with a tumor that expresses CEA, comprising administering a therapeutically effective amount of the humanized antibody of claim 2 to the subject, thereby treating the tumor.

27. A method for detecting a cell expressing CEA in a subject, comprising: contacting a sample from the subject with the humanized antibody of claim 1; and detecting the presence of a complex of the antibody with CEA, thereby detecting a cell expressing CEA.

28. The method of claim 27, wherein the subject has a tumor.

29. The method of claim 28, wherein the antibody is labeled.

30. The method of claim 27, wherein the humanized antibody comprises a light chain comprising an amino acid sequence as set forth in SEQ ID NO: 9 and a heavy chain comprising an amino acid sequence as set forth in SEQ ID NO: 12.

31. The method of claim 27, wherein the sample is a biopsy specimen, autopsy specimen, and pathology specimens, or a biological fluid.

32. A method for in vivo diagnosis of a CEA expressing tumor in a subject, comprising
  (a) administering to a mammal a diagnostically effective amount of the humanized antibody of claim 1;
  (b) allowing sufficient time for the humanized antibody to become specifically localized to at least one tumor cell; and
  (c) detecting the humanized antibody in vivo at a site where the humanized antibody has become localized, thereby diagnosing the tumor.

33. A kit comprising a container comprising the humanized antibody of claim 1.

34. A humanized COL-1 monoclonal antibody, comprising a heavy and a light chain variable region, wherein the light chain variable region comprises an amino acid sequence as set forth in SEQ ID NO: 9 and the heavy chain variable region comprises an amino acid sequence as set forth in SEQ ID NO: 12; and wherein the humanized antibody retains binding affinity for CEA, as compared to HuCOL-1$_{AbrCDR}$, deposited as ATCC Accession No. PTA-4644.

35. The antibody of claim 34, further comprising a detectable label.

36. The antibody of claim 35, wherein the detectable label is a fluorescent or a radioactive molecule.

37. The antibody of claim 34, wherein the antibody has reduced immunogenicity, as compared to HuCOL-1$_{AbrCDR}$, deposited as ATCC Accession No. PTA-4644.

38. A pharmaceutical composition comprising a therapeutically effective amount of the humanized antibody of claim 34 in a pharmaceutically acceptable carrier.

39. A kit comprising: a container comprising the humanized antibody of claim 34.

40. A method for treating a subject with a tumor that expresses CEA, comprising administering to the subject a therapeutically effective amount of a humanized antibody of claim 34, thereby treating the tumor.

41. The method of claim 40, further administering a therapeutically effective amount of an immunogenic agent.

42. A humanized COL-1 monoclonal antibody, comprising: a heavy chain comprising an amino acid sequence as set forth in SEQ ID NO: 8 and a light chain comprising the amino acid sequence of SEQ ID NO: 4, wherein a framework residue at position 79 of SEQ ID NO: 8 and at least framework residues at positions 20, 38, 48, 67, and 81 of the amino acid sequence SEQ ID NO: 8 are substituted with an amino acid from a corresponding position in the amino acid sequence set forth as SEQ ID NO: 6, and wherein the humanized COL-1 antibody retains binding affinity for carcinoembryonic antigen (CEA) and has reduced immunogenicity, as compared to HuCOL-1$_{AbrCDR}$, deposited as ATCC Accession No. PTA-4644.

43. A method for treating a subject with a tumor that expresses CEA, comprising administering a therapeutically effective amount of the humanized antibody of claim 1 to the subject, thereby treating the tumor.

44. The composition of claim 23, wherein the functional fragment of the humanized antibody comprises a detectable label.

45. The antibody of claim 44, wherein the detectable label is a fluorescent or a radioactive molecule.

46. A method for treating a subject with a tumor that expresses CEA, comprising administering a therapeutically effective amount of the composition of claim 23 to the subject, thereby treating the tumor.

47. A method for treating a subject with a tumor that expresses CEA, comprising administering a therapeutically effective amount of the humanized antibody of claim 42 to the subject, thereby treating the tumor.

* * * * *